(12) United States Patent
Burnett et al.

(10) Patent No.: US 9,610,459 B2
(45) Date of Patent: Apr. 4, 2017

(54) COOLING SYSTEMS AND METHODS FOR CONDUCTIVE COILS

(75) Inventors: Daniel Rogers Burnett, San Francisco, CA (US); Christopher Hermanson, Santa Cruz, CA (US); James H. Ahlman, Sunnyvale, CA (US); Bruno Strul, Portola Valley, CA (US)

(73) Assignee: EMKinetics, Inc., San Francisco, CA (US)

( * ) Notice: Subject to any disclaimer, the term of this patent is extended or adjusted under 35 U.S.C. 154(b) by 8 days.

(21) Appl. No.: 12/509,362

(22) Filed: Jul. 24, 2009

(65) Prior Publication Data
US 2011/0021863 A1  Jan. 27, 2011

(51) Int. Cl.
*A61N 2/02* (2006.01)
*A61N 2/00* (2006.01)

(52) U.S. Cl.
CPC ............... *A61N 2/02* (2013.01); *A61N 2/008* (2013.01)

(58) Field of Classification Search
CPC ... A61N 2/04; A61N 2/02; A61N 1/00; A61B 17/52
USPC ....................................... 600/9–15
See application file for complete search history.

(56) References Cited

U.S. PATENT DOCUMENTS

| | | |
|---|---|---|
| 2,893,392 A | 7/1959 | Wagner et al. |
| 3,034,507 A | 5/1962 | McConnell et al. |
| 3,817,254 A | 6/1974 | Maurer |
| 3,841,305 A * | 10/1974 | Hallgren .................. 600/13 |
| 4,233,965 A | 11/1980 | Fairbanks |
| 4,266,533 A | 5/1981 | Ryaby et al. |
| 4,428,366 A | 1/1984 | Findl et al. |
| 4,456,012 A | 6/1984 | Lattin |
| 4,548,208 A | 10/1985 | Niemi |
| 4,574,809 A | 3/1986 | Talish et al. |
| 4,784,737 A | 11/1988 | Ray et al. |

(Continued)

FOREIGN PATENT DOCUMENTS

| | | |
|---|---|---|
| GB | 0637560 | 5/1950 |
| GB | 2298370 | 9/1996 |

(Continued)

OTHER PUBLICATIONS

U.S. Appl. No. 12/509,304, filed Jul. 24, 2009 in the name of Burnett et al., non-final Office Action mailed Feb. 14, 2011.

(Continued)

*Primary Examiner* — Christine H Matthews
(74) *Attorney, Agent, or Firm* — Levine Bagade Han LLP

(57) ABSTRACT

An energy emitting apparatus for providing a medical therapy includes one or more energy generators, a logic controller connected to the one or more energy generators, and optionally one or more sensors that are connected to the logic controller for detecting muscle stimulation or electric conduction in a target nerve. The energy generators produce energy focused on the target nerve upon receiving a signal from the logic controller, and the energy can be varied by the logic controller according to an input provided by the one or more sensors. In certain embodiments, the energy emitting apparatus includes one or more conductive coils that produce a magnetic field focused on the target nerve upon receiving an electric current. In certain embodiments, a variety of cooling mechanisms or systems may be implemented for cooling the coil.

40 Claims, 31 Drawing Sheets

(56) References Cited

U.S. PATENT DOCUMENTS

| | | |
|---|---|---|
| 4,804,054 A | 2/1989 | Howson et al. |
| 4,837,049 A | 6/1989 | Byers et al. |
| 4,915,110 A | 4/1990 | Kitov |
| 4,926,878 A | 5/1990 | Snedeker |
| 4,940,453 A | 7/1990 | Cadwell |
| 4,994,015 A | 2/1991 | Cadwell |
| 5,000,178 A | 3/1991 | Griffith |
| 5,014,699 A | 5/1991 | Pollack et al. |
| 5,092,835 A | 3/1992 | Schurig et al. |
| 5,158,080 A | 10/1992 | Kallok |
| 5,181,902 A | 1/1993 | Erickson et al. |
| 5,309,909 A | 5/1994 | Gadsby et al. |
| 5,314,401 A | 5/1994 | Tepper |
| 5,314,453 A | 5/1994 | Jeutter |
| 5,401,233 A | 3/1995 | Erickson et al. |
| 5,449,378 A | 9/1995 | Schouenborg |
| 5,518,495 A | 5/1996 | Kolt |
| 5,562,707 A | 10/1996 | Prochazka et al. |
| 5,690,693 A | 11/1997 | Wang et al. |
| 5,715,837 A | 2/1998 | Chen |
| 5,725,471 A | 3/1998 | Davey et al. |
| 5,749,909 A | 5/1998 | Schroeppel et al. |
| 5,766,124 A | 6/1998 | Polson |
| 5,792,187 A | 8/1998 | Adams |
| 5,792,209 A | 8/1998 | Varner |
| 5,833,600 A | 11/1998 | Young |
| 5,857,957 A | 1/1999 | Lin |
| 5,978,712 A | 11/1999 | Suda et al. |
| 5,984,854 A | 11/1999 | Ishikawa et al. |
| 6,009,878 A | 1/2000 | Weijand et al. |
| 6,024,691 A | 2/2000 | Tepper et al. |
| 6,029,090 A | 2/2000 | Herbst |
| 6,032,677 A | 3/2000 | Blechman et al. |
| 6,066,084 A | 5/2000 | Edrich et al. |
| 6,086,525 A | 7/2000 | Davey et al. |
| 6,088,619 A | 7/2000 | Hein et al. |
| 6,123,658 A | 9/2000 | Schweighofer et al. |
| 6,143,035 A | 11/2000 | McDowell |
| 6,155,966 A | 12/2000 | Parker |
| 6,179,770 B1 | 1/2001 | Mould |
| 6,190,893 B1 | 2/2001 | Shastri et al. |
| 6,200,259 B1 | 3/2001 | March |
| 6,213,933 B1 | 4/2001 | Lin |
| 6,219,575 B1 | 4/2001 | Nemati |
| 6,256,533 B1 | 7/2001 | Yuzhakov et al. |
| 6,261,221 B1 | 7/2001 | Tepper et al. |
| 6,312,612 B1 | 11/2001 | Sherman et al. |
| 6,319,241 B1 | 11/2001 | King et al. |
| 6,334,856 B1 | 1/2002 | Allen et al. |
| 6,349,233 B1 | 2/2002 | Adams |
| 6,366,795 B1 | 4/2002 | Bremer et al. |
| 6,379,324 B1 | 4/2002 | Gartstein et al. |
| 6,440,096 B1 | 8/2002 | Lastovich et al. |
| 6,443,883 B1 | 9/2002 | Ostrow et al. |
| 6,451,240 B1 | 9/2002 | Sherman et al. |
| 6,471,903 B2 | 10/2002 | Sherman et al. |
| 6,473,652 B1 | 10/2002 | Sarwal et al. |
| 6,491,620 B1 | 12/2002 | Davey |
| 6,493,588 B1 | 12/2002 | Malaney et al. |
| 6,500,110 B1 | 12/2002 | Davey et al. |
| 6,503,231 B1 | 1/2003 | Prausnitz et al. |
| 6,511,463 B1 | 1/2003 | Wood et al. |
| 6,527,694 B1 | 3/2003 | Ishikawa et al. |
| 6,533,949 B1 | 3/2003 | Yeshurun et al. |
| 6,537,242 B1 | 3/2003 | Palmer |
| 6,553,263 B1 | 4/2003 | Meadows et al. |
| 6,558,361 B1 | 5/2003 | Yeshurun |
| 6,565,532 B1 | 5/2003 | Yuzhakov et al. |
| 6,582,393 B2 | 6/2003 | Sage, Jr. |
| 6,591,124 B2 | 7/2003 | Sherman et al. |
| 6,595,947 B1 | 7/2003 | Mikszta et al. |
| 6,603,987 B2 | 8/2003 | Whitson |
| 6,611,707 B1 | 8/2003 | Prausnitz et al. |
| 6,622,035 B1 | 9/2003 | Merilainen et al. |
| 6,623,457 B1 | 9/2003 | Rosenberg |
| 6,652,443 B1 | 11/2003 | Struppler et al. |
| 6,652,478 B1 | 11/2003 | Gartstein et al. |
| 6,654,636 B1 | 11/2003 | Dev et al. |
| 6,656,147 B1 | 12/2003 | Gertsek et al. |
| 6,663,556 B2 | 12/2003 | Barker |
| 6,663,820 B2 | 12/2003 | Arias et al. |
| 6,671,527 B2 | 12/2003 | Petersson et al. |
| 6,678,556 B1 | 1/2004 | Nolan et al. |
| 6,684,106 B2 | 1/2004 | Herbst |
| 6,689,100 B2 | 2/2004 | Connelly et al. |
| 6,690,959 B2 | 2/2004 | Thompson |
| 6,697,669 B2 | 2/2004 | Dev et al. |
| 6,701,185 B2 | 3/2004 | Burnett et al. |
| 6,735,474 B1 | 5/2004 | Loeb et al. |
| 6,743,211 B1 | 6/2004 | Prausnitz et al. |
| 6,767,341 B2 | 7/2004 | Cho |
| 6,770,022 B2 | 8/2004 | Mechlenburg et al. |
| 6,770,480 B1 | 8/2004 | Canham |
| 6,782,283 B2 | 8/2004 | Schmidt et al. |
| 6,790,372 B2 | 9/2004 | Roy et al. |
| 6,808,506 B2 | 10/2004 | Lastovich et al. |
| 6,835,184 B1 | 12/2004 | Sage et al. |
| 6,866,659 B2 | 3/2005 | Nemati |
| 6,881,203 B2 | 4/2005 | Delmore et al. |
| 6,899,838 B2 | 5/2005 | Lastovich |
| 6,908,453 B2 | 6/2005 | Fleming et al. |
| 6,926,660 B2 | 8/2005 | Miller |
| 6,931,277 B1 | 8/2005 | Yuzhakov et al. |
| 6,939,311 B2 | 9/2005 | Geiger |
| 6,941,171 B2 | 9/2005 | Mann et al. |
| 6,960,193 B2 | 11/2005 | Rosenberg |
| 6,962,772 B2 | 11/2005 | Liu et al. |
| 6,972,013 B1 | 12/2005 | Zhang et al. |
| 6,980,855 B2 | 12/2005 | Cho |
| 7,013,179 B2 | 3/2006 | Carter et al. |
| 7,027,478 B2 | 4/2006 | Ackley |
| 7,032,302 B1 | 4/2006 | Schmidt et al. |
| 7,045,069 B2 | 5/2006 | Ozeryansky |
| 7,047,070 B2 | 5/2006 | Wilkinson et al. |
| 7,048,723 B1 | 5/2006 | Frazier et al. |
| 7,079,355 B2 | 7/2006 | Hsiao et al. |
| 7,083,592 B2 | 8/2006 | Lastovich et al. |
| 7,104,947 B2 | 9/2006 | Riehl |
| 7,115,108 B2 | 10/2006 | Wilkinson et al. |
| 7,117,034 B2 | 10/2006 | Kronberg |
| 7,130,696 B2 | 10/2006 | Carter et al. |
| 7,132,054 B1 | 11/2006 | Kravitz et al. |
| 7,153,256 B2 | 12/2006 | Riehl et al. |
| 7,187,976 B2 | 3/2007 | Duncan et al. |
| 7,226,439 B2 | 6/2007 | Prausnitz et al. |
| 7,262,068 B2 | 8/2007 | Roy et al. |
| 7,273,474 B2 | 9/2007 | Chang et al. |
| 7,285,113 B2 | 10/2007 | Yeshurun |
| 7,315,758 B2 | 1/2008 | Kwiatkowski et al. |
| 7,316,665 B2 | 1/2008 | Laurent et al. |
| 7,320,664 B2 | 1/2008 | Riehl et al. |
| 7,332,197 B2 | 2/2008 | Wood et al. |
| 7,332,339 B2 | 2/2008 | Canham |
| 7,344,499 B1 | 3/2008 | Prausnitz et al. |
| 7,367,936 B2 | 5/2008 | Myers et al. |
| D571,920 S | 6/2008 | Juliana et al. |
| 7,396,326 B2 | 7/2008 | Ghiron et al. |
| 7,410,476 B2 | 8/2008 | Wilkinson et al. |
| 7,415,299 B2 | 8/2008 | Zimmermann et al. |
| 7,416,541 B2 | 8/2008 | Yuzhakov et al. |
| 7,429,333 B2 | 9/2008 | Chiou et al. |
| 7,473,244 B2 | 1/2009 | Frazier et al. |
| 7,481,337 B2 | 1/2009 | Luharuka et al. |
| 7,497,980 B2 | 3/2009 | Xu et al. |
| 7,500,911 B2 | 3/2009 | Johnson et al. |
| 7,520,848 B2 | 4/2009 | Schneider et al. |
| 7,522,061 B2 | 4/2009 | Rondoni et al. |
| 7,530,968 B2 | 5/2009 | Gonnelli |
| 7,536,226 B2 | 5/2009 | Williams et al. |
| 7,556,615 B2 | 7/2009 | Pettis et al. |
| 7,556,821 B2 | 7/2009 | Ameri et al. |
| 7,560,036 B2 | 7/2009 | Golubovic-Liakopoulos et al. |
| 7,570,992 B2 | 8/2009 | Nolan et al. |
| 7,572,405 B2 | 8/2009 | Sherman et al. |

(56) References Cited

U.S. PATENT DOCUMENTS

| | | |
|---|---|---|
| 7,574,256 B2 | 8/2009 | Carter |
| 7,578,954 B2 | 8/2009 | Gartstein et al. |
| 7,582,069 B2 | 9/2009 | Laurent et al. |
| 7,588,552 B2 | 9/2009 | Yeshurun et al. |
| 7,591,806 B2 | 9/2009 | Xu |
| 7,627,938 B2 | 12/2009 | Kim et al. |
| 7,647,112 B2 | 1/2010 | Tracey et al. |
| 7,648,484 B2 | 1/2010 | Yeshurun et al. |
| 7,651,946 B2 | 1/2010 | Wilke et al. |
| 7,658,728 B2 | 2/2010 | Yuzhakov |
| 7,941,201 B2 | 5/2011 | Chiou et al. |
| 8,430,805 B2 | 4/2013 | Burnett et al. |
| 8,435,166 B2 | 5/2013 | Burnett et al. |
| 2002/0028991 A1 | 3/2002 | Thompson |
| 2002/0082465 A1 | 6/2002 | Bashford et al. |
| 2002/0099323 A1 | 7/2002 | Dev et al. |
| 2002/0111777 A1 | 8/2002 | David |
| 2002/0133129 A1 | 9/2002 | Arias et al. |
| 2002/0183647 A1 | 12/2002 | Gozani et al. |
| 2002/0183804 A1 | 12/2002 | Malaney et al. |
| 2003/0028072 A1 | 2/2003 | Fischell et al. |
| 2003/0144625 A1 | 7/2003 | Sherman et al. |
| 2003/0158583 A1 | 8/2003 | Burnett et al. |
| 2003/0158585 A1 | 8/2003 | Burnett |
| 2003/0216729 A1 | 11/2003 | Marchitto et al. |
| 2003/0217754 A1 | 11/2003 | Thomas et al. |
| 2004/0010276 A1 | 1/2004 | Jacobs et al. |
| 2004/0054393 A1 | 3/2004 | Stemme et al. |
| 2004/0082875 A1 | 4/2004 | Donoghue et al. |
| 2004/0092860 A1 | 5/2004 | Dev et al. |
| 2004/0111139 A1 | 6/2004 | McCreery |
| 2004/0122787 A1 | 6/2004 | Avinash et al. |
| 2004/0127939 A1 | 7/2004 | Grey |
| 2004/0138517 A1 | 7/2004 | Osorio et al. |
| 2004/0146611 A1 | 7/2004 | Arias et al. |
| 2004/0147964 A1 | 7/2004 | Nolan et al. |
| 2004/0173220 A1 | 9/2004 | Harry et al. |
| 2004/0210254 A1 | 10/2004 | Burnett et al. |
| 2004/0210282 A1 | 10/2004 | Flock et al. |
| 2005/0021104 A1 | 1/2005 | Dilorenzo |
| 2005/0029223 A1 | 2/2005 | Yeshurun |
| 2005/0033380 A1 | 2/2005 | Tanner et al. |
| 2005/0099290 A1 | 5/2005 | Govari |
| 2005/0143783 A1 | 6/2005 | Boveja et al. |
| 2005/0143789 A1 | 6/2005 | Whitehurst et al. |
| 2005/0171576 A1 | 8/2005 | Williams et al. |
| 2005/0203602 A1 | 9/2005 | Wallace et al. |
| 2005/0277998 A1 | 12/2005 | Tracey et al. |
| 2005/0283202 A1 | 12/2005 | Gellman |
| 2006/0004244 A1 | 1/2006 | Phillips et al. |
| 2006/0016452 A1 | 1/2006 | Goetz et al. |
| 2006/0030845 A1 | 2/2006 | Leung et al. |
| 2006/0047316 A1 | 3/2006 | Fischell et al. |
| 2006/0049957 A1 | 3/2006 | Surgenor et al. |
| 2006/0052839 A1 | 3/2006 | Kim et al. |
| 2006/0084938 A1 | 4/2006 | Zhang et al. |
| 2006/0122454 A1 | 6/2006 | Riehl et al. |
| 2006/0122660 A1 | 6/2006 | Boveja et al. |
| 2006/0135844 A1 | 6/2006 | Alekseyenko |
| 2006/0161039 A1 | 7/2006 | Juliana et al. |
| 2006/0173261 A1 | 8/2006 | Kall et al. |
| 2006/0178576 A1* | 8/2006 | Weber ................. A61F 2/88 600/422 |
| 2006/0184211 A1 | 8/2006 | Gaunt et al. |
| 2006/0199159 A1 | 9/2006 | Ghiron et al. |
| 2006/0276702 A1 | 12/2006 | Mcginnis |
| 2007/0021712 A1 | 1/2007 | Bernard et al. |
| 2007/0021803 A1 | 1/2007 | Deem et al. |
| 2007/0027353 A1 | 2/2007 | Ghiron et al. |
| 2007/0027354 A1 | 2/2007 | Riehl et al. |
| 2007/0027355 A1 | 2/2007 | Riehl et al. |
| 2007/0142885 A1 | 6/2007 | Hantash et al. |
| 2007/0208212 A1 | 9/2007 | Dilorenzo |
| 2007/0250162 A1 | 10/2007 | Royalty |
| 2007/0265489 A1 | 11/2007 | Fowler et al. |
| 2007/0265675 A1 | 11/2007 | Lund et al. |
| 2007/0276318 A1 | 11/2007 | Henley |
| 2007/0282246 A1 | 12/2007 | Henley |
| 2008/0004484 A1 | 1/2008 | Wieraszko et al. |
| 2008/0033510 A1 | 2/2008 | Herregraven et al. |
| 2008/0058874 A1 | 3/2008 | Westlund et al. |
| 2008/0063866 A1 | 3/2008 | Allen et al. |
| 2008/0114199 A1 | 5/2008 | Riehl et al. |
| 2008/0177128 A1 | 7/2008 | Riehl et al. |
| 2008/0177347 A1 | 7/2008 | Tehrani et al. |
| 2008/0183070 A1 | 7/2008 | Unal et al. |
| 2008/0200748 A1 | 8/2008 | Testani et al. |
| 2008/0224808 A1 | 9/2008 | Ghiron et al. |
| 2008/0262287 A1 | 10/2008 | Dussau |
| 2008/0288035 A1 | 11/2008 | Gill et al. |
| 2008/0300655 A1 | 12/2008 | Cholette |
| 2008/0306325 A1 | 12/2008 | Burnett et al. |
| 2008/0312725 A1 | 12/2008 | Penner |
| 2009/0030337 A1 | 1/2009 | Gozani et al. |
| 2009/0054950 A1 | 2/2009 | Stephens |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076344 A1 | 3/2009 | Libbus et al. |
| 2009/0076345 A1 | 3/2009 | Manicka et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076410 A1 | 3/2009 | Libbus et al. |
| 2009/0076559 A1 | 3/2009 | Libbus et al. |
| 2009/0076565 A1 | 3/2009 | Surwit |
| 2009/0118777 A1 | 5/2009 | Iki et al. |
| 2009/0132018 A1 | 5/2009 | DiUbaldi et al. |
| 2009/0162570 A1 | 6/2009 | Swenberg et al. |
| 2009/0171236 A1 | 7/2009 | Davies |
| 2009/0227829 A1 | 9/2009 | Burnett et al. |
| 2009/0227831 A1 | 9/2009 | Burnett et al. |
| 2009/0234179 A1 | 9/2009 | Burnett et al. |
| 2009/0234410 A1 | 9/2009 | Libbus et al. |
| 2009/0264792 A1 | 10/2009 | Mazar |
| 2009/0292194 A1 | 11/2009 | Libbus et al. |
| 2010/0022864 A1 | 1/2010 | Cordero et al. |
| 2010/0049021 A1 | 2/2010 | Jina et al. |
| 2010/0056881 A1 | 3/2010 | Libbus et al. |
| 2010/0057149 A1 | 3/2010 | Fahey |
| 2010/0119482 A1 | 5/2010 | Yun et al. |
| 2010/0160712 A1 | 6/2010 | Burnett et al. |
| 2010/0161005 A1 | 6/2010 | Wahlgren et al. |
| 2010/0168501 A1 | 7/2010 | Burnett et al. |
| 2010/0204538 A1 | 8/2010 | Burnett et al. |
| 2010/0222629 A1 | 9/2010 | Burnett et al. |
| 2010/0222630 A1 | 9/2010 | Mangrum et al. |
| 2010/0318009 A1 | 12/2010 | Stanley |
| 2011/0264163 A1 | 10/2011 | Tracey et al. |
| 2011/0295100 A1 | 12/2011 | Hegde et al. |
| 2012/0059432 A1 | 3/2012 | Emborg et al. |
| 2012/0302821 A1 | 11/2012 | Burnett |
| 2013/0006322 A1 | 1/2013 | Tai |
| 2013/0072746 A1 | 3/2013 | Burnett et al. |
| 2013/0310909 A1 | 11/2013 | Simon et al. |
| 2014/0213842 A1 | 7/2014 | Simon et al. |
| 2016/0067515 A1 | 3/2016 | Burnett et al. |
| 2016/0067517 A1 | 3/2016 | Burnett |
| 2016/0074671 A1 | 3/2016 | Burnett et al. |

FOREIGN PATENT DOCUMENTS

| | | |
|---|---|---|
| GB | 2336544 | 10/1999 |
| JP | 2000-254239 | 9/2000 |
| WO | WO 03/070317 | 8/2003 |
| WO | WO 2006/061688 | 6/2006 |
| WO | WO 2008/032279 | 3/2008 |
| WO | WO 2008/042902 | 4/2008 |
| WO | WO 2008/115426 | 9/2008 |
| WO | WO 2010/047599 | 4/2010 |
| WO | WO 2011/011748 | 1/2011 |
| WO | WO 2011/011749 | 1/2011 |
| WO | WO 2011/053607 | 5/2011 |

(56) References Cited

FOREIGN PATENT DOCUMENTS

| WO | WO 2011/053661 | 5/2011 |
|---|---|---|
| WO | WO 2011/150332 | 12/2011 |
| WO | WO 2012/040243 | 3/2012 |

OTHER PUBLICATIONS

"Bioflex® RX754P, Single Coated Medical Pressure Sensitive Adhesive Tape," *Technical Data*, 2 pages, Dec. 2005.
3M Corporation, 3M™ XYZ/Isotropic Electrically Conductive Adhesive Transfer Tape 9707, *3M Electronics Markets Materials Division*, 60-5002-0350-4, 8 pages, 2004, 3M.
Aaron, Roy K. et al., "Therapeutic Effects of Electromagnetic Fields in the Stimulation of Connective Tissue Repair," *Journal of Cellular Biography*, 52(1):42-6, May 1993, Wiley-Liss, Inc.
AmGel Technologies, "AG603 Sensing Gel, Sensing Gel Designed for ECG Applications," AG603-3/10, 1 page, 2010.
AmGel Technologies, "AG702 Stimulating Gel, Stimulating Gel Designed for carbon film," AG702-02/06, 1 page, 2006.
AmGel Technologies, "AG902-184/229 Grounding Gel, Grounding Gel Designed for Electrosurgical Pads," AG902 Series, 1 page, 2010.
AmGel Technologies, "Release Films," 1 Page, Jul. 25, 2006, Revision 1.
Australian Patent Application No. 2007303223 filed Oct. 2, 2007 in the name of EMKinetics, Inc., Office Action mailed Sep. 7, 2010.
Balmaseda, Marion T. Jr., et al., "Burns in Functional Electric Stimulation: Two Case Reports," *Archives of Physical Medicine and Rehabilitation*, vol. 38., pp. 452-453, Jul. 1987.
Biowave Corporation, "510(k) Summary for the Biowave Deepwave Neuromodulation Pain Therapy Device," 6 pages, Appendix B, Dec. 13, 2005.
Biowave Corporation, "510(k) Summary for the Biowave Deepwave Neuromodulation Pain Therapy Device," 7 pages, Appendix E, Aug. 15, 2006.
Biowave Corporation, "Percutaneous Neuromodulation Pain Therapy System," *deepwave*, RevB/080926, 2008.
BlueCross BlueShield of Kansas City, "Percutaneous Electrical Nerve Stimulation (PENS) and Percutaneous Neuromodulation Therapy (PNT)," 7 pages, 1988.
Bodhale, D.W. et al., "Design, fabrication and analysis of silicon microneedies for transdermal drug delivery applications," *Proceedings of the 3rd International Conference on the Development of BME in Vietnam*, pp. 84-88, Jan. 11-14, 2010.
Cabodevila, G. et al., "An overview on drug delivery using microneedles", *Institute FEMTO-ST, Dept LPMO*, 24 pages, Oct. 2005, Workshop Micro Dosing Systems.
Choi, S. et al., "Microneedle Electrode Array for Electroporation of Skin for Gene Therapy," 2 pages, 2005, Controlled Release Society 32nd Annual Meeting and Exposition Transactions.
Curley, S. et al., "Radiofrequency Ablation of Unresectable Primary and Metastatic Hepatic Malignancies," *Annals of Surgery*, vol. 230(1):1-8, 1999 Lippincott Williams & Wilkins, Inc.
CystoMedix, Inc., "Percutaneous Tibial Nerve Stimulation via Urgent® PC Neuromodulation System—An Emerging Technology for managing Overactive Bladder," *Business Briefing: Global Surgery*, 6 pages, 2004.
Fallon Community Health Plan, "Spinal Cord Stimulation," 4 pages, 2006.
Grundfest H. et al., "Stainless Steel Micro-Needle Electrodes Made by Electrolytic Pointing," *Review of Scientific Instruments*, vol. 21(4):2 pages, 1950, American Institute of Physics.
Harvinder S. Gill et al., "Effect of microneedle design on pain in human subjects," *NIH Public Access Author Manuscript*, 24(7): 585-594, Sep. 2008, Clinical Journal of Pain.
Huber, D.E. et al., "Popliteal Vein Compression Under General Anaesthesia," *European Journal of Vascular and Endovascular Surgery*, vol. 37, pp. 464-469, 2009, Elsevier Ltd.

International Patent Application No. PCT/US2007/080196 in the name of EMKinetics, Inc. filed Oct. 2, 2007, International Search Report and Written Opinion mailed Apr. 24, 2008.
International Patent Application No. PCT/US2010/043142 in the name of EMKinetics, Inc. filed Jul. 23, 2010, International Search Report and Written Opinion mailed Sep. 24, 2010.
International Patent Application No. PCT/US2010/043143 in the name of EMKinetics, Inc. filed Jul. 23, 2010, International Search Report and Written Opinion mailed Sep. 15, 2010.
International Patent Application No. PCT/US2010/054167 in the name of EMKinetics, Inc. filed Oct. 26, 2010, International Search Report and Written Opinion mailed Dec. 23, 2010.
International Patent Application No. PCT/US2010/054353 in the name of EMKinetics, Inc. filed Oct. 27, 2010, International Search Report and Written Opinion mailed Dec. 28, 2010.
Jacobson, Jerry I. et al., "Low-Amplitude, Extremely Low Frequency Magnetic Fields for the Treatment of Osteoarthritic Knees: A Double-Blind Clinical Study," *Electromagnetic Fields and Human Health. Fundamental and Applied Research*, pp. 363-364, Sep. 17-24, 2002, Proceedings of the Third International Conference.
Jasper, H. et al., "Unipolar Electromyograms of Normal and Denervated Human Muscle," pp. 231-244, Oct. 12, 1948, Department of Neurology and Neurosurgery, McGill University, and Montreal Neurological Institute.
Kurtzke, John F., "Epidemiology of Spinal Cord Injury," *IV Panamerican Congress of Neurology*, 18(2-3): 157-90, 93, 1975.
Lin et al., "Magnetic Stimulation of the Bladder in Dogs," AAEM Annual Meeting 1993, *Muscle & Nerve*, Oct. 1993 (Abstract).
Luttge, R. "Microneedle array electrode for human EEG recording," IFMBE Proceedings 22, pp. 1246-1249, 2008, Springer-Verlag Berlin Heidelberg 2009.
Maass et al., "Contactless Nerve Stimulation and Signal Detection by Inductive Transducer," *Symposium on Application of Magnetism in Bioengineering*, 1969.
McFarlane, J.P. et al., "Acute Suppression of Idiopathic Detrusor Instability with Magnetic Stimulation of the Sacral Nerve Roots," *British Journal of Urology*, 80(5): 734-41, Nov. 1997.
Morrison, P.R. et al., "Radiofrequency Ablation of Thoracic Lesions: Part I, Experiments in the Normal Porcine Thorax," *American Journal of Roentgenology*, 2005;184:375-380, Feb. 2005, American Roentgen Ray Society.
NeuroStar TMS Therapy, NeuroStar TMS Therapy® Recipient of Medical Design Excellence Award, *PRNewswire*, 3 pages, Apr. 2009.
Newmark, Inc., "Standard Products, Highest Quality Components, Designed & Produced Exclusively for Electrode Manufacturers," *Innovation by Design Newmark*, 2 pages, www.newmarkine.com/std_prods.htm, printed on May 3, 2010.
Noble, J.H. et al., "Automatic segmentation of the facial nerve and chorda tympani in CT images using spatially dependent features values", Medical Phsysics, vol. 35(12), pp. 5375-5384, Dec. 2008, American Association Physical Medicine.
Patel, G. et al., "Microneedles: The option for painless delivery," www.pharmainfo.net/reviews/microneedles-option-painless-delivery, 6 pages, printed on Sep. 9, 2008.
*PubMed, U.S. National Library of Medicine National Institutes of Health*, microneedle array electrode—Pub Med results, www.ncbi.nlm.nig.gov/sites/entrez, 2 pages, Search performed on Apr. 22, 2010.
*PubMed, U.S. National Library of Medicine National Institutes of Health*, microneedle electrode—Pub Med results, www.ncbi.nlm.nig.gov/sites/entrez, 7 pages, Search performed on Apr. 22, 2010.
Shafik, Ahmed, "Magnetic Stimulation: A Novel Method for Inducing Evacuation of the Neuropathic Rectum and Urinary Bladder in a Canine Model," *Urology* 54(2): 368-372, Aug. 1999.
Sheridan, MT. et al., "Pretreatment apoptosis in carcinoma of the cervix correlates with changes in tumour oxygenation during radiotherapy," *British Journal of Cancer*, 82(6):1177-1182, 2000 Cancer Research Campaign.
Sivagangabalan, G. et al., "Comparison of Electroanatomic Contact and Noncontact Mapping of Ventricular Scar in a Postinfarct Ovine Model With Intramural Needle Electrode Recording and Histologi-

(56) References Cited

OTHER PUBLICATIONS cal Validation," *Circulation: Arrhythmia and Electrophysiology, Journal of the American Heart Association*, vol. 1:363-369, 2008, American Heart Association.
Solbiati, L. et al., "Percutaneous US-guided Radio-Frequency Tissue Ablation of Liver Metastases: Treatment and Follow-up in 16 Patients," *Radiology*, 202(1)195-203, 1997 L.S. RSNA.
The Magstim Company Ltd, "Air Film Coil," *Magstim*, 4 pages, 2007.
Thon, W.F. et al., "Neuromodulation of voiding dysfunction and pelvic pain," *World Journal of Urology*, vol. 9: pp. 138-141, 1991, Springer-Verlag.
Trock, David H., "Electromagnetic Fields and Magnets Investigational Treatment for Musculoskeletal Disorders," *Rheumatic Diseases Clinics of North America*, vol. 26, No. 1., Feb. 2000.
Trock, David H., et al., "The Effect of Pulsed Electromagnetic Fields in the Treatment of Osteoarthritis of the Knee and Cervical Spine. Report of Randomized, Double Blind, Placebo Controlled Trials," *The Journal of Rheumatology*, 1903-1911, 1994.
U.S. Appl. No. 12/815,348, filed Jun. 14, 2010 in the name of Reydel et al., non-final Office Action dated Feb. 14, 2011.
U.S. Appl. No. 10/077,434, filed Feb. 19, 2002 in the name of Burnett et al., non-final Office Action mailed Jul. 2, 2003.
U.S. Appl. No. 10/077,434, filed Feb. 19, 2002 in the name of Burnett et al., Notice of Allowance mailed Oct. 17, 2003.
U.S. Appl. No. 11/332,797, filed Jan. 27, 2006 in the name of Mangrum et al., final Office Action mailed Jul. 27, 2009.
U.S. Appl. No. 11/866,329, filed Oct. 2, 2007 in the name of Burnett et al., final Office Action mailed Mar. 16, 2010.
U.S. Appl. No. 11/866,329, filed Oct. 2, 2007 in the name of Burnett et al., non-final Office Action mailed Jun. 10, 2009.
U.S. Appl. No. 12/469,365, filed May 20, 2009 in the name of Mangrum et al., non-final Office Action mailed Aug. 27, 2010.
U.S. Appl. No. 12/695,087, filed Jan. 27, 2010 in the name of Mangrum et al., non-final Office Action mailed Dec. 23, 2010.
vanSonnenberg, E. et al., "Radiofrequency Ablation of Thoracic Lesions: Part 2, Initial Clinical Experience—Technical and Multidisciplinary Considerations in 30 Patients," *American Journal of Roentgenology*, 2005;184:381-390, Feb. 2005, American Roentgen Ray Society.
Wanich, T. et al, "A Randomized Placebo-Controlled Study to Determine Safety and Efficacy in Terms of Pain Reduction, Increased Range of Motion, and Reduced Pain Medications, for a Novel Percutaneous Neuromodulation Pain Therapy Device ("Deepwave®") Following Post-Operative Treatments for Total Knee Replacement Procedures," American Academy of Orthopaedic Surgeons 2009 Annual Meeting, 6 pages, Feb. 25-28, 2008, Biowave Corporation.
Warwick, K. et al., "The Application of Implant Technology for Cybernetic Systems," *Archives of Neurology*, vol. 60:1369-1373, Oct. 2003, American Medical Association.
Wijkstrda et al., "Selective Stimulation and Blocking of Sacral Nerves: Research Setup and Preliminary Results," *Annual International Conference of the IEEE Engineering in Medicine and Biology Society*, vol. 13, No. 2, 1991.
Wilke, N. et al., "Fabrication and Characterisation of Microneedle Electrode Arrays using Wet Etch Technologies," 5 pages, Oct. 20-21, 2004, EMN04, NMRC, University College.
Zhao, M., "Genetic Analysis of Electric Signal-directed Cell Movement," 33 pages, Apr. 8, 2008, Modelling Complex Biological Systems in the Context of Genomics.
Zoll Lifecor Corporation, "What is the LifeVest Wearable Defibrillator," http://www.lifecor.com/about_lifevest/about.asp#, 1 page, printed on Jan. 7, 2011.

\* cited by examiner

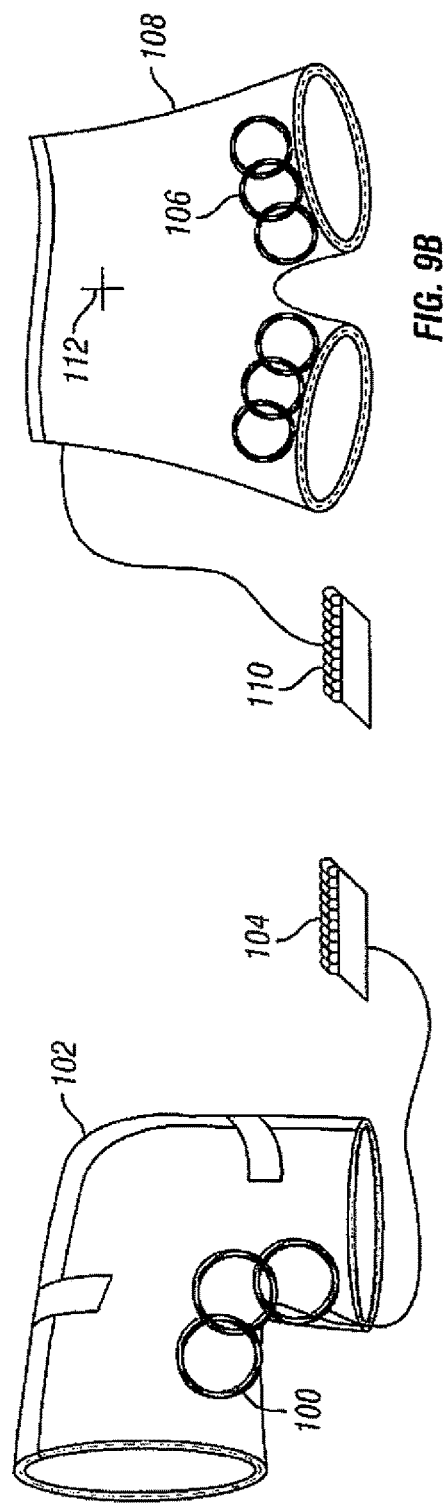
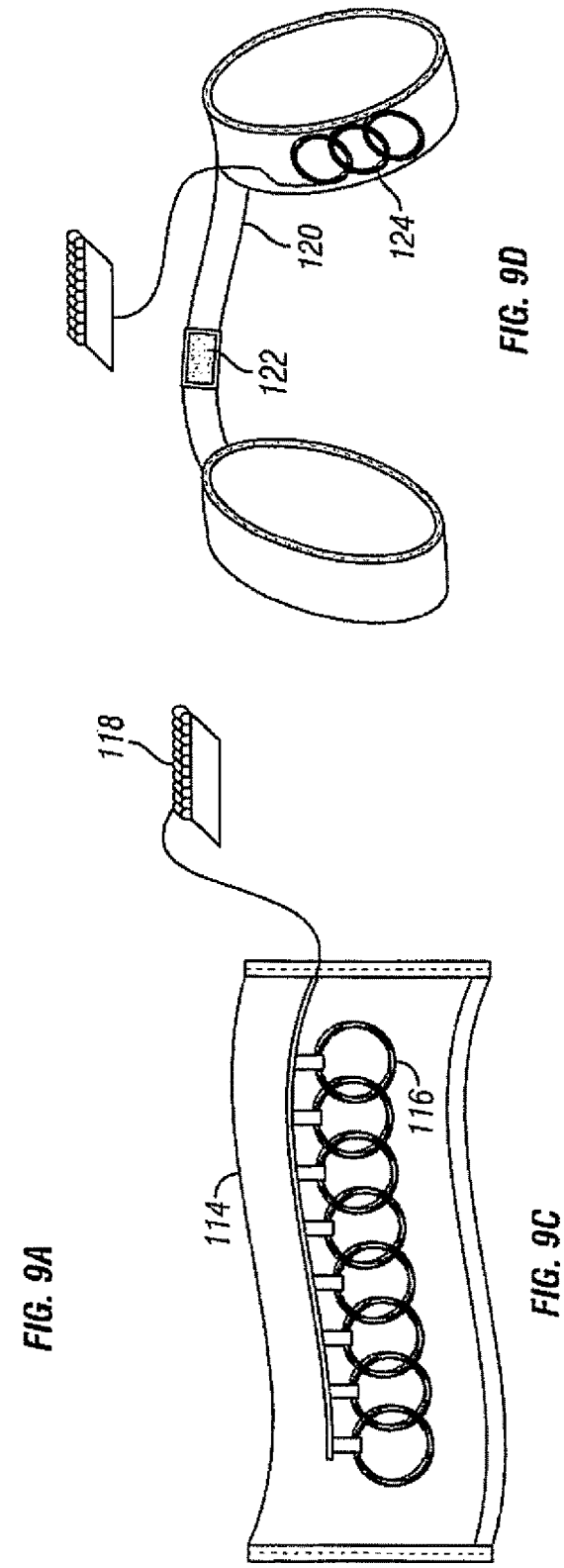

COOLING SYSTEMS AND METHODS FOR CONDUCTIVE COILS

BACKGROUND

Overactive bladder ("OAB") and urinary incontinence ("UI") affect over 16% of the American population each year, or approximately 34 million men and women. Outside of the United States, OAB and UI affects over 46 million Europeans. The economic cost of OAB and UI is estimated to be in excess of $12 billion a year in the United States alone.

Due to the social stigmas attached to OAB and UI and to misunderstandings related to the symptoms associated with OAB and UI, only 40% of the affected individuals in the United States seek medical treatment. Of those 13.6 million Americans seeking medical treatment, nearly 30% or 4 million individuals are reportedly unsatisfied with their current therapy.

Known treatments for OAB and UI include exercise and behavioral modifications, pharmacological therapies, surgical intervention and neuromodulation, but each of these treatments exhibits severe limitations.

Exercise and behavioral modifications often require patients to adhere to stringent routines, including scheduled voiding, maintenance of a bladder diary, and intense exercise regimens. While this type of treatment may be a viable option for a small group of highly dedicated individuals, its daily impact on a person's life makes it unattractive for most patients.

Pharmacological intervention is the most widely prescribed therapy for OAB and UI. Unfortunately, patients often suffer from side effects related to their drug therapies. Such side effects are sometimes serious and are particularly pronounced in elderly patient populations that tend to use a plurality of medications. In addition, approximately 30% of all patients subjected to pharmacological therapies appear to be dissatisfied with the efficacy of their prescribed treatments.

Surgical intervention IS extremely invasive and often results in a long-term requirement for catheterization that may become permanent in some instances. The negative impact of these procedures on the patient's quality of life and their high expense make surgical intervention a recommended option only when all other treatment options have been exhausted.

Neuromodulation is another available therapy for OAB and UI. In general, pulsed electromagnetic stimulation ("PES") has proven to have beneficial effects in a variety of medical applications. The related scientific principle is that an electric current passing through a coil generates an electromagnetic field, which induces a current within a conductive material placed inside the electromagnetic field.

More particularly, PES has been shown to be an effective method of stimulating a nerve positioned within the electromagnetic field, thereby affecting a muscle controlled by that nerve. For example, in the paper titled "Contactless Nerve Stimulation and Signal Detection by Inductive Transducer" presented at the 1969 Symposium on Application of Magnetism in Bioengineering, Maass et al. disclosed that a nerve threading the lumen of a toroid could be stimulated by a magnetic field of 0.7 Volt peak amplitude and a 50 µs duration in a monitor wire, and that such stimulation could generate a contraction of major leg muscles in anesthetized mammals.

Various attempts were made to use PES for treating a variety of ailments. For example, U.S. Pat. No. 4,548,208 to Niemi discloses an apparatus for inducing bone growth by generating an electric current in the body through the external application of an electromagnetic field. Such apparatus includes opposing clamps disposed on a limb and may optionally include feedback coils and a microprocessor for sensing the magnetic field, so to avoid an overcurrent mode. Therefore, this apparatus optimizes the magnetic field on the basis of measurements of the generated magnetic field.

U.S. Pat. No. 4,940,453 to Cadwell discloses a method and apparatus for magnetically stimulating the neural pathways of a higher level organism. In this invention, a sinusoidally fluctuating current flow is created through a coil that overlies neurons to be stimulated, and frequency of the current flow and frequency of the magnetic field produced by the coil predetermined to correspond to the time constant of the neurons to be stimulated. Sensors for sensing coil conditions, such as coil temperature, may also be included.

U.S. Pat. No. 5,000,178 to Griffith discloses an electrical to electromagnetic transducer for applying electromagnetic energy to damaged parts of a living body by directing electromagnetic radiation to a certain damaged body part. Electromagnetic radiation is initially generated by a dipole consisting of a bar of high permeability material wrapped with an electrically conductive coil. Magnetic fields, which are generated away from the damaged body part, intersect a conductive shield and establish eddy currents, which in turn generate magnetic fields opposite and nearly equal to the magnetic fields generated by the electromagnetic source. The resultant electromagnetic fields reinforce the electromagnetic field directed towards the damaged body part and diminish the electromagnetic field directed away from the damaged body part.

U.S. Pat. No. 5,014,699 to Pollack et al. discloses a non-invasive, portable electromagnetic therapeutic method and apparatus for promoting the healing of damaged or diseased living tissue, including fractured bone. These method and apparatus involve generating a signal that has a series of substantially symmetric voltage cycles of bursted pulses with narrow pulse widths of 0.5 to 20 microseconds, and further involve converting the signal into an electromagnetic field extending into an area that contains tissue to be healed. This invention provides for no feedback on the efficiency of the applied stimulation.

In a paper titled "Selective Stimulation and Blocking of Sacral Nerves: Research Setup and Preliminary Results," published in Annual International Conference of the IEEE Engineering in Medicine and Biology Society, Vol. 13, No. 2, 1991, Wijkstrda et al. used an external pulsed magnetic coil to stimulate a peripheral nerve for the treatment of urinary incontinence. The authors used a large magnetic field produced by a single coil to ensure that the nerve was fired and the resulting nerve conduction was frequently painful or intolerable. In addition, coil alignment was problematic because an internally implanted coil was utilized, which had to be aligned with the fully external magnetic field to stimulate the nerve. Due to the difficulty in positioning the device, the practical application of this therapy does not permit home healthcare usage without a preset alignment and monitoring of the nerve, and no provision was made to insure that the nerve was actually being stimulated or to adjust the device in response to commonly occurring physiologic and anatomic variations in nerve locations.

U.S. Pat. No. 5,181,902 Erickson et al. and U.S. Pat. No. 5,314,401 to Tepper disclose pulsed electromagnetic field ("PEMF") transducer systems usable to perform PEMF therapies (such as after spinal fusion) by generating flux-aided electromagnetic fields. The drive electronics includes a PEMF processor that executes a PEMF program for controlling the activation of the electromagnetic fields (field strength and cycle).

In a paper titled: "Magnetic Stimulation of the Bladder in Dogs" presented at the 1993 AAEM Annual Meeting, the abstract of which was published in the Muscle & Nerve issue of October 1993, Lin et al. disclosed that magnetic stimulation could be employed to stimulate the cortex, spinal nerves and peripheral nerves of dogs through direct transabdominal stimulation of the detrusor muscles or through stimulation of the lumbosacral roots.

As shown, however, there has been no provision made to measure the efficacy of PES treatment, causing patients to be treated improperly, either by an insufficient or excessive exposure to PES. Other attempts to monitor PES dosage exhibit serious drawbacks. For example, U.S. Pat. No. 5,518,495 to Kot discloses an apparatus for the treatment of arthritis utilizing a magnetic field therapy, which includes an adjustable voltage source that is connected to a source of line voltage and a coil connected to the adjustable voltage source. This apparatus has no feedback system to advise a healthcare provider of the efficiency of the treatment.

U.S. Pat. No. 5,984,854 to Ishikawa et al. discloses a method for treating urinary incontinence based on delivering a train of current pulses through one or more magnetic stimulation coils so to induce a train of magnetic flux pulses, which then induce an eddy current within the body and stimulates a group of pelvic floor muscles, the pudendal nerve, the external urethral sphincter, or the tibial nerve. While this method includes the use of pulsed electromagnetic for treating urinary incontinence, no specific components are envisioned to facilitate the placement of the magnetic coils over a targeted region of the body or a system for monitoring the efficiency of the therapy being applied.

U.S. Pat. No. 6,086,525 to Davey et al. discloses a magnetic nerve stimulator that includes a core constructed from a material having a high field saturation having a coil winding disposed thereon. A thyrister capacitive discharge circuit pulses the device, and a rapidly changing magnetic field is guided by the core, preferably made from vanadium permendur.

U.S. Pat. No. 6,701,185 to Burnett et al. also discloses an electromagnetic stimulation device that includes a plurality of overlapping coils, which can be independently energized in a predetermined sequence such that each coil will generate its own independent electromagnetic field and significantly increase the adjacent field. Unfortunately, none of these patents provides a system for monitoring the efficiency of the therapy in progress, either with respect to the proper positioning of the winding over the area to be treated or of the intensity of the magnetic field to be applied.

Other PES therapies require the implantation of devices into the patient, with the consequent discomfort, risk and cost to the patient. For example, U.S. Pat. No. 6,735,474 to Loeb et al. discloses a method and system for treating UI and/or pelvic pain by injecting or laparoscopically implanting one or more battery-or radio frequency-powered microstimulators that include electrodes placed beneath the skin of the perineum and/or adjacent the tibial nerve.

U.S. Pat. No. 6,941,171 to Mann et al. describes a method and a system for treating incontinence, urgency, frequency, and/or pelvic pain that includes implantation of electrodes on a lead or a discharge portion of a catheter adjacent the perineal nerve(s) or tissue(s) to be stimulated. Stimulation pulses, either electrical or drug infusion pulses, are supplied by a stimulator implanted remotely through the lead or catheter, which is tunneled subcutaneously between the stimulator and stimulation site.

Other PES therapies involve the use of electrodes placed on or beneath the skin of a patient. Recent data on invasive, needle-based PES of the posterior tibial nerve in individuals with OAB and UI indicates that PES can modulate bladder dysfunction through its action on the pudendal nerve and the sacral plexus, which provide the major excitatory input to the bladder.

In a paper titled "Percutaneous Tibial Nerve Stimulation via Urgent® PC Neuromodulation System—An Emerging Technology for managing Overactive Bladder," which was published in Business Briefing: Global Surgery 2004, CystoMedix, Inc. disclosed that peripheral tibial nerve stimulation ("PTNS") had been found effective in treating OAB. The disclosed procedure involved the use of electrode and generator components, including a small 34-gauge needle electrode, lead wires and a hand-held electrical generator. However, the procedure requires the permanent implantation of an electrical stimulation device in the patient. One estimate put the cost of treatment at nearly $14,000 with additional routine care costs of $593 per patient per year. Additionally, risks of battery failure, implant infection, and electrode migration led to a high re-operation rate and made this procedure unattractive.

U.S. Pat. No. 7,117,034 to Kronberg discloses a method for generating an electrical signal for use in biomedical applications that includes two timing-interval generators. In this invention, skin-contact electrodes may be placed over an area of interest and a microprocessor may direct timing and sequencing functions, although such timing and sequencing functions are not related to the actual efficacy of the treatment while treatment is being performed.

U.S. Patent Application Publication No. 2005/0171576 to Williams et al. discloses an electro-nerve stimulation apparatus that includes a pulse generator, a first electrically conductive, insulated lead wire, a second electrically conductive, insulated lead wire, an electrically conductive transcutaneous electrode and an electrically conductive percutaneous needle electrode. Connected to one end of the first and second lead wires is a connector for electrically coupling with the pulse generator. In this invention, a percutaneous needle electrode is inserted through the skin in proximity to the desired internal stimulation site and electric stimulation is employed, rather than pulsed electromagnetic stimulation. Moreover, the Williams invention does not contemplate mechanisms for facilitating use of the device by an untrained user, nor a monitoring of the applied therapy.

A neuromodulation alternative is a posterior tibial nerve stimulator, often referred to as SANS, but as is the case with other forms of neuromodulation, this procedure is invasive in nature and requires the insertion of a needle five centimeters into the patient's ankle region to stimulate the posterior tibial nerve. This procedure also requires a minimum of twelve sessions for initial treatment, possibly with additional sessions required for maintenance.

Also, therapies involving the use of traditional insertable or implantable percutaneous needles require penetration into deeper tissues and carry with them the added risk of infection, while causing pain and discomfort to the patient. This often results in ineffective treatment and or reduced patient compliance.

Additionally, some existing techniques for cooling coils include limitations and disadvantages. For example, some cooling techniques require air to first be cooled, e.g., refrigerated, which involves the use of additional components and parts and could increase cost. Some cooling devices utilize low flow rates and fail to prevent rapid rises in temperature, such that coils must be powered down frequently to prevent overheating damage. As a result, large treatment gaps and low rep rates are often required during therapy that utilizes such devices. Also, heated air is often vented in the direction of the patient due to the configuration of existing devices and necessary flow patterns. Because the vented air can reach high temperatures, this could pose a danger to patients. These cooling deficiencies can limit the load, power and running time at which coils may be operated.

SUMMARY

In certain embodiments, an energy emitting system for providing a medical therapy is provided. The energy emitting system may include one or more conductive coils configured to generate a magnetic field focused on a target nerve. The conductive coil can include a coil body having a central aperture, and a material may be positioned on a surface of the coil body. Optionally, the material is a non-electrically conductive material. The non-electrically conductive material may be configured to maintain air or fluid flow gaps between adjacent turns of the coil body for cooling the conductive coil. The non-electrically conductive material may also form air or fluid flow channels for cooling the conductive coil.

In certain embodiments, an energy emitting system for providing a medical therapy is provided. The energy emitting system may include one or more conductive coils positioned within a housing, where the conductive coil is configured to generate a magnetic field or deliver an electrical stimulus to a patient. The conductive coil can have a coil body having at least a first turn, a second turn, and a central aperture. Optionally, a cooling device may be provided, where the cooling device is configured to draw air into the housing. The air may be drawn over the coil body, between the first and second turns, and/or through the central aperture to cool the coil.

In certain embodiments, an energy emitting system for providing a medical therapy is provided. The energy emitting system may include one or more conductive coils configured to generate a magnetic field focused on a target nerve. The conductive coils include at least a first turn and a second turn. The first turn can include a first surface having at least one raised protrusion which separates the first turn from the second turn, forming a gap that allows for convection cooling of the coil.

In certain embodiments, an energy emitting system for providing a medical therapy is provided. The energy emitting system may include one or more conductive coils configured to generate a magnetic field focused on a target nerve. The conductive coil can include a first end and a second end, with a coil body positioned between the first end and second end. The coil body may include a lumen, which provides a passage extending from the first end to the second end of the conductive coil. The lumen of the coil is configured to permit the passage of fluid between the first end and the second end for cooling the conductive coil.

In certain embodiments, a method of magnetic induction therapy is provided. The method may include positioning a first portion of a patient's body relative to an energy emitting device such that a target nerve within the first portion of the body is in proximity to a conductive coil disposed within or along the energy emitting device. A current is passed through the conductive coil to generate a magnetic field focused on the target nerve. The patient's body is positioned in order to concentrate an electromagnetic or magnetic flux near or over a target nerve. Also, air may be drawn at a flow rate over the conductive coil body, between the first and second turns of the conductive coil, and through a central aperture of the conductive coil to cool the conductive coil. The therapy may be used to treat or prevent a variety of conditions, e.g., urinary incontinence, fecal incontinence or restless leg syndrome.

Other features and advantages will appear hereinafter. The features and elements described herein can be used separately or together, or in various combinations of one or more of them.

BRIEF DESCRIPTION OF THE DRAWINGS

The drawings constitute a part of this specification and include exemplary embodiments of the invention, which may be embodied in various forms. It is to be understood that in some instances various aspects of the embodiments may be shown exaggerated or enlarged to facilitate an understanding of the embodiments.

FIGS. 9A-9D are schematic representations of different garments adapted to operate as apparatus for magnetic induction therapy.

FIG. 44a is a front view of a variation of a conductive coil.

FIG. 44b shows a top view of a portion of a coil turn of the conductive coil of FIG. 44a.

FIG. 46b shows a side view of an energy emitting system including the conductive coil of FIG. 46a.

DETAILED DESCRIPTION

Detailed descriptions of various embodiments are provided herein. It is to be understood, however, that the embodiments may be embodied in various forms. Therefore, the specific details disclosed herein are not to be interpreted as limiting, but rather as a representative basis for teaching one skilled in the art how to employ the various embodiments in virtually any detailed system, structure, or manner.

Various embodiments will now be described. The following description provides specific details for a thorough understanding and enabling description of these embodiments. One skilled in the art will understand, however, that the embodiments may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments. Certain terms may even be emphasized below. Any terminology intended to be interpreted in any restricted manner, however, will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

Figure 1:
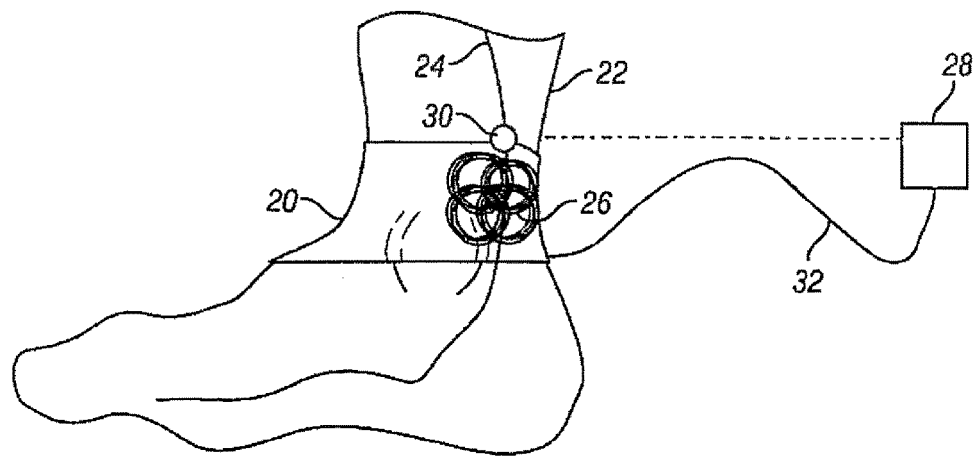
FIG. 1 is a schematic view of a variation of an apparatus for magnetic induction therapy.

Referring first to FIG. 1, a first embodiment includes a coil wrap 20, which is depicted as disposed over ankle 22 circumferentially to surround a portion of tibial nerve 24. Because tibial nerve 24 is targeted, this embodiment is particularly suited for the treatment of OAB and VI. In other embodiments, coil wrap 20 may be configured to surround other body parts that contain a portion of tibial nerve 24 or of other nerves branching from or connected to tibial nerve 24, still making these embodiments suitable for treating OAB and VI. In still other embodiments, coil wrap 20 may be configured for surrounding body parts that contain other nerves when treatments of other ailments are intended.

Coil wrap 20 may be manufactured from a variety of materials suitable for wearing over ankle 22. Preferably, coil wrap is produced from a soft, body-compatible material, natural or synthetic, for example, cotton, wool, polyester, rayon, Gore-Tex®, or other fibers or materials known to a person skilled in the art as non-irritating and preferably breathable when tailored into a garment. Coil wrap 22 may even be manufactured from a molded or cast synthetic material, such as a urethane gel, to add extra comfort to the patient by providing a soft and drapable feel. Additionally, coil wrap 20 may be produced from a single layer of material or from multiple material layers and may include padding or other filling between the layers.

Coil wrap 20 contains one or more conductive coils 26 arranged to produce a pulsed magnetic field that will flow across tibial nerve 24 and generate a current that will flow along tibial nerve 24 and spread along the length of tibial nerve 24 all the way to its sacral or pudendal nerve root origins. Coils 26 may be a single coil shaped in a simple helical pattern or as a figure eight coil, a four leaf clover coil, a Helmholtz coil, a modified Helmholtz coil, or may be shaped as a combination of the aforementioned coils patterns. Additionally, other coil designs beyond those mentioned hereinabove might be utilized as long as a magnetic field is developed that will encompass tibial nerve 24 or any other target nerve. When a plurality of coils is utilized, such coils may be disposed on a single side of ankle 22, or may be disposed on more than one side, for example, on opposing sides, strengthening and directionalizing the flow of the magnetic field through tibial nerve 24 or other peripheral nerves of interest.

Coil wrap 20 is preferably configured as an ergonomic wrap, for example, as an essentially cylindrical band that can be pulled over ankle 22, or as an open band that can be wrapped around ankle 22 and have its ends connected with a buckle, a hoop and loop system, or any other closing system known to a person skilled in the art. By properly adjusting the position of coil wrap 20 over ankle 22, a patient or a health care provider may optimize the flow of the magnetic field through tibial nerve 24, based on system feedback or on sensory perceptions of the patient, as described in greater detail below.

The electric current that produces the magnetic field by flowing through coils 26 is supplied by a programmable logic controller 28, which is connected to coils 26, for example, with a power cord 32. A sensor 30 that feeds information to logic controller 28 is also provided, in order to tailor the strength of the magnetic field and control activation of coils 26 based on nerve conduction. The purpose of sensor 30 is to detect and record the firing of the target nerve and to provide related information to logic controller 28, so to render the intended therapy most effective. For example, sensor input may cause logic controller 28 to alter the strength or pulse amplitude of the magnetic field based on sensor input, or fire the coils in a certain sequence.

In this embodiment, as well as in the other embodiments described hereinafter, sensor 30 may include one or more sensor patches and may be placed at different distances from the region of direct exposure to the magnetic field. For example, sensor 30 may be configured as a voltage or current detector in the form of an EKG patch and may be placed anywhere in the vicinity of the target nerve to detect its activation. For ease of description, the term "coils" will be used hereinafter to indicate "one or more coils" and "sensor" to indicate "one or more sensors," unless specified otherwise.

By virtue of the above described arrangement, coil wrap 20 provides a reproducibly correct level of stimulation during an initial therapy session and during successive therapy sessions, because the presence or absence of nerve conduction is detected and, in some embodiments, measured when coil wrap 20 is first fitted and fine-tuned on the patient. In addition to properly modulating the applied magnetic field, the positioning of coils 26 over ankle 22 may also be tailored according to the input provided by sensor 30, so to fine-tune the direction of the magnetic field. Such an adjustment of the direction, amplitude, and level of the stimulation provided to the target nerve through the above described automated feedback loop, to ensure that peripheral nerve conduction is being achieved can be an important feature when implemented.

If the magnetic pulse does not substantially interfere with sensor 30, sensor 30 may be placed directly within the field of stimulation, so that power supplied to the system may be conserved. This is particularly important for battery-powered systems. Alternatively, sensor 30 may also be placed at a distance from the magnetic field and still properly detect neural stimulation.

In a method of use of coil wrap 20, the amplitude and/or firing sequence of coils 26 may be ramped up progressively, so that the magnetic field is increased in strength and/or breadth until nerve conduction is detected, after which the applied stimulus is adjusted or maintained at its current level for the remainder of the therapy. The level of stimulation may be also controlled through a combination of feedback from sensor 30 and feedback based on perceptions of the patient. For example, the patient may activate a switch once she perceives an excessive stimulation, in particular, an excessive level of muscular stimulation. In one instance, the patient may be asked to push a button or turn a knob when she feels her toe twitching or when she experiences paresthesia over the sole of her foot. The patient will then continue pressing the button or keep the knob in the rotated position until she can no longer feel her toe twitching or paresthesia in her foot, indicating that that level of applied stimulation corresponds to an optimal therapy level. From that point on, the patient may be instructed to simply retain her foot, knee, or other limb within coil wrap 20 until therapy has been terminated while the system is kept at the optimal level. Adding patient input enables control of coil wrap 20 during outpatient treatments, because the patient is now able to adjust the intensity of the magnetic field herself beyond the signals provided to logic controller 28 by sensor 30.

Detecting and, if the case, measuring conduction in one or more nerves along the conduction pathways of the stimulated nerve confirms that the target nerve has been stimulated, providing an accurate assessment of the efficiency of the applied therapy on the patient. A concomitant detection of muscle contraction may also confirm that the target nerve is being stimulated and provide an indication to the patient or to a healthcare provider as to whether stimulation has been applied at an excessive level in view of the anatomical and physiological characteristics of the patient.

Based on the foregoing, coil wrap 20 allows for a consistent, user-friendly targeting and modulation of the peripheral nerves via the posterior tibial nerve on an outpatient basis, in particular, the targeting and modulation of the pudendal nerve and of the sacral plexus. When multiple coils 26 are present, coils 26 may be activated simultaneously or differentially to generate the desired magnetic field. The direction and location of each of coils 26 may be reversibly or irreversibly adjusted by the healthcare provider or by the patient, customizing the location of the applied stimulation to the anatomy and therapy needs of each patient. After a healthcare provider has optimized position and firing sequence for each of coils 26, the patient may be sent home with coil wrap 20 adjusted to consistently target the desired nerve. In one variant of the present embodiment, an automatic feedback system adjusts one or more of firing sequence, firing strength or position of coils 26 within coil wrap 20 during the initial setup and also during successive therapy sessions.

In summary, certain embodiments include the creation of a loop consisting of feeding information on nerve conduction to logic controller 28 and on logic controller 28 tailoring the electrical current sent to coil wrap 20 according to the information received from sensor 26 based on whether or not the nerve is receiving the desired stimulation and, in some embodiments, the desired amount of stimulation. This arrangement offers an unparalleled level of therapy control and flexibility within a home care setting, because a consistent, repeatable stimulation of the target nerve can be attained. Aside from adjusting the position of coils 26 in accordance with the patient's anatomy and physiological variations, controlling pulse amplitude is also of great importance even during different therapy sessions with the same patient. For example, a patient with leg edema will encounter difficulties in properly adjusting coil wrap 20 based on whether her legs and ankles are swollen or not swollen, and the power required to penetrate to posterior tibial nerve 24 (in the case of a VI therapy) will vary greatly due to the variable depth of the nerve. Thus, having feedback provided by sensor 26 becomes a necessity for achieving an accurate dosage of the treatment rather than an option. Benchtop testing has demonstrated that a system constructed according embodiments described herein is capable of non-invasively generating electrical currents similar to those found in therapeutic electro-stimulation and to do so in different settings.

Figure 2:
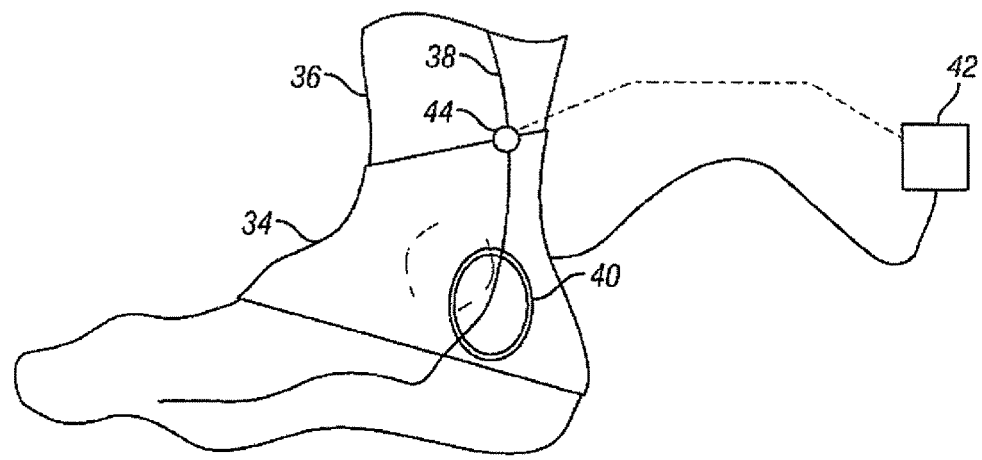
FIG. 2 is a schematic view of a variation of an apparatus for magnetic induction therapy.

Referring now to FIG. 2, a second embodiment will be described with reference to a coil wrap 34 disposed over ankle 36 for the purpose of treating VI by targeting tibial nerve 38. In this second embodiment, one or more Helmholtz coils 40 are disposed within coil wrap 34 to create a more narrowly directed magnetic field over tibial nerve 38. Like in the all other embodiments described herein, more than one coil (in the present embodiment, more than one Helmholtz coil 40) may be placed within coil wrap 34 and be disposed in different positions within coil wrap 34, in order to optimize magnetic flux over tibial nerve. For example, two Helmholtz coils may be disposed one opposite to the other within coil wrap 34.

Having coil windings arranged along a common longitudinal axis, as required in a Helmholtz coil configuration, generates a more focused magnetic field and a more accurate targeting of tibial nerve 38 or of any other nerve. Like in the previous embodiment, the operation of coils 40 is controlled by a logic controller 42, which is in turn connected to sensor 44 that monitors conduction in tibial nerve 44 and that generates a feedback to logic controller 42 about the efficiency of the therapy in progress. Therefore, like in the previous embodiment, the coupling of sensor 44 with logic controller 42 optimizes operation of coil wrap 34 according to results measured at the level of tibial nerve 38. Also like in the previous embodiment, manual adjustments to the parameters of electric current provided by logic controller 42 to Helmholtz coil 40 may also be made manually by the patient or by a healthcare provider, and coil wrap 34 may be structured so that the position of Helmholtz coil 40 within coil wrap 34 is adjusted as desired either manually by the patient or by a healthcare provider, or automatically by logic controller 42.

Figure 3:
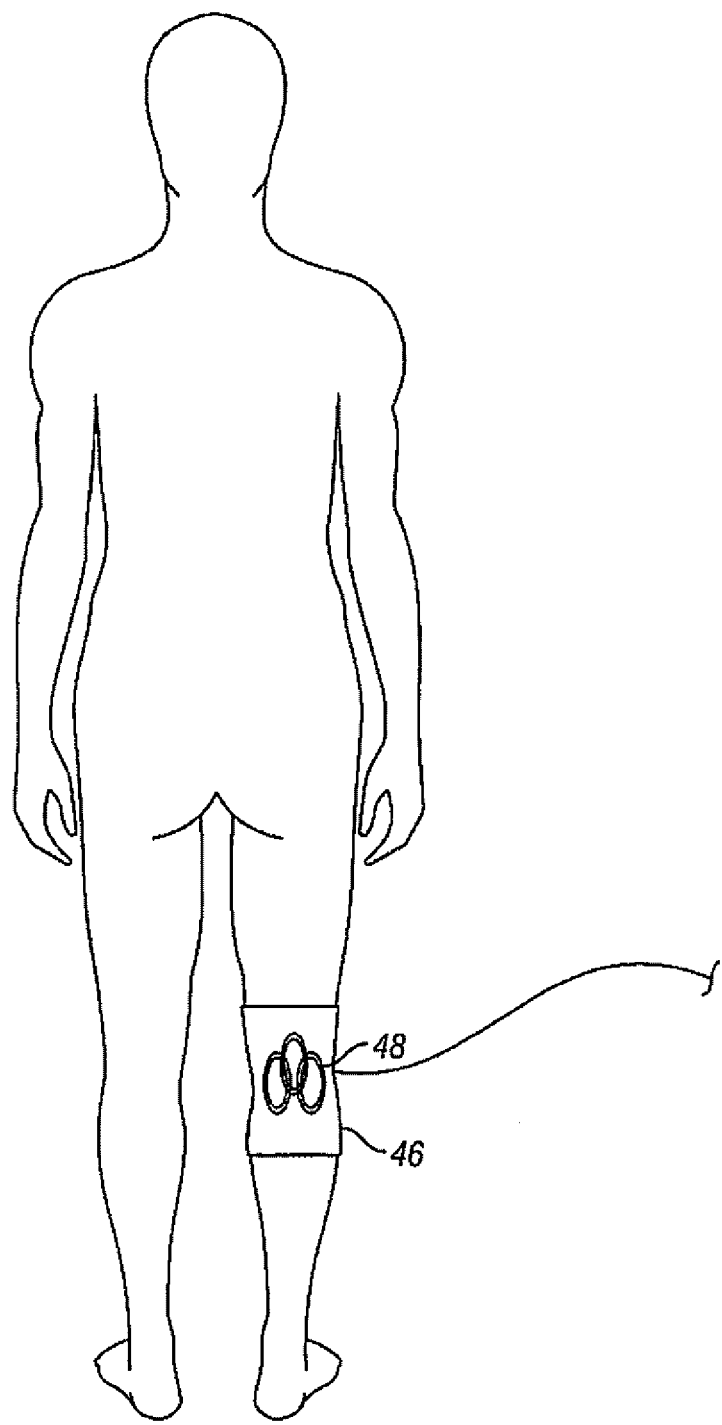
FIG. 3 is a schematic view of a variation of an apparatus for magnetic induction therapy.

Referring now to FIG. 3, a third embodiment includes a coil wrap 46 configured for wrapping over the popliteal fossa of a patient, in the region of the knee, to stimulate the posterior tibial nerve (not shown). The configuration and structure of coil wrap 46 reflect the body portion covered by coil wrap 46, but the key system components of coil wrap 46, such as the type, number and disposition of the coils (for example, the use of overlapping coils); the connections of the coils with a logic controller; and the use of one or more sensors (also not shown) to detect nerve conduction are all comparable to those in the previously described embodiments.

Figure 4:
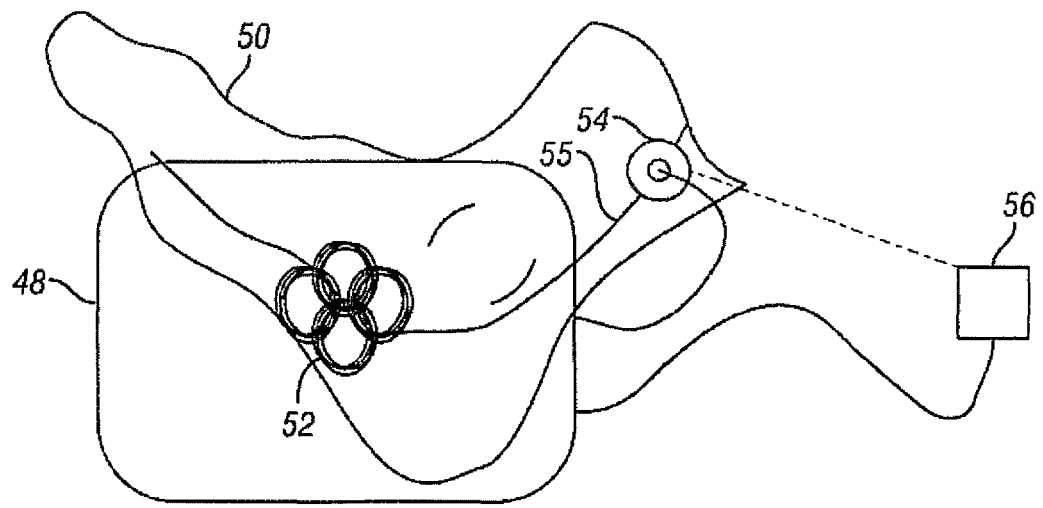
FIG. 4 is a schematic view of a variation of an apparatus for magnetic induction therapy.

Referring now to FIG. 4, a fourth embodiment includes a footrest or foot cradle 48, which is structured to contain at least a portion of a foot 50. One or more coils 52 are enclosed within cradle 48, and a sensor 54 is disposed along the pathway of tibial nerve 55, sensing conduction in tibial nerve 55, and is also connected to a logic controller 56. Coils 52, sensor 54 and logic controller 56 may be arranged in different configurations, in the same manner as in the preceding embodiments.

Cradle 48 may be made from a variety of materials and may be monolithic, or have a hollow or semi-hollow structure to enable the movement of coils 52 within cradle 48, as described in greater detail below. Preferably, cradle 48 has an ergonomically design allowing the ankle and heel of the patient to be retained within cradle 48, in a position that matches the positions of stimulating coils 52 to the area of stimulation. The design of cradle 48 provides for a particularly comfortable delivery of therapy to patients that prefer to remain seated during their therapy, and enables the patient to perform the required therapy within a health care facility, or to take cradle 48 home, typically after an initial session and appropriate training in a health care facility. In that event, the patient will be trained to apply sensor 54 autonomously and to adjust stimulation to a comfortable level.

FIG. 4 shows coils 52 disposed as overlapping and the use of a single sensor patch 54 positioned proximally to the stimulation site. However, coil 52 may be configured as a single coil, a figure eight coil, a four leaf clover coil, a Helmholtz coil, a modified Helmholtz coil or a any combination of the aforementioned coils, or as any other coil design providing an effective stimulation to the target nerve. In addition, coils 52 may be fired individually, sequentially or simultaneously according to the feedback provided by sensor 54.

In one variant of this embodiment, sensor 54 may include a conductive electrode patch that provides a feedback to logic controller 56 for adjusting, if necessary, the stimulation parameters of coils 52. Alternatively, sensor 54 may be a sensor patch that is either applied to the skin of the patient or is incorporated within the structure of cradle 48.

Figure 5:
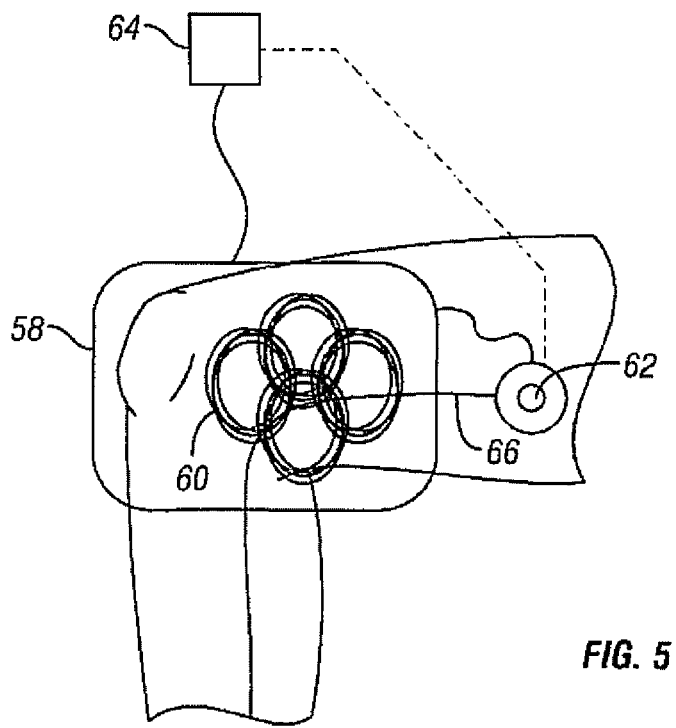
FIG. 5 is a schematic view of a variation of an apparatus for magnetic induction therapy.

Referring now to FIG. 5, a fifth embodiment includes a knee rest or knee cradle 58 that contains one or more conductive coils 60, one or more sensors 62 and a logic controller 64. The components of this embodiment are similar to those described with reference to the preceding embodiments, as regards the structure and materials of cradle 58, the nature and disposition of coils 60, the type and operation of sensor 62, and the function and operation of logic controller 64. Cradle 58 is configured to target the popliteal fossa of the patient, thus to target tibial nerve 66. In that respect, the present embodiment is similar to the embodiment illustrated in FIG. 3, but while the embodiment of FIG. 3 is configured as a wrap that may be worn while the patient is standing, the present embodiment is configured as a cradle that is more suited for treatment while the patient is sitting or laying down.

A method of use of the foot cradle depicted in FIG. 4 is described with reference to FIGS. 6A-6D. During a first step illustrated in FIG. 6A, foot 68 is disposed in cradle 70 that contains one or more conductive coils 72, which are connected to a logic controller (not shown) that manages the flow of electric power to coils 72.

Figure 6A:
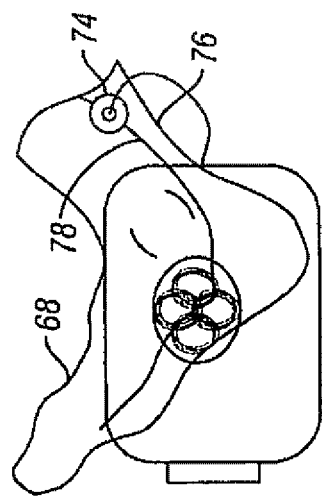
FIGS. 6A-6D are schematic illustrations depicting a first method of use of an apparatus for magnetic induction therapy. This method is based on adjusting the position of the conductive coils so to optimize a magnetic flow applied to a target nerve.
Figure 6B:
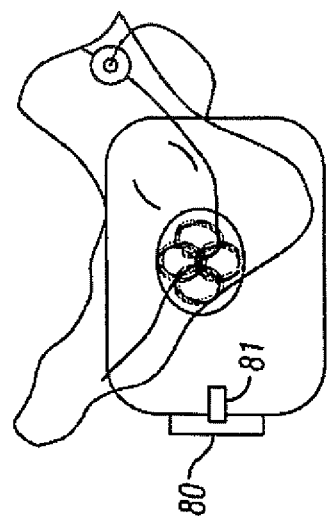

During a second step illustrated in FIG. 6B, a sensor 74 is disposed on foot 68 or on ankle 76 or on another appropriate portion of the patient's body, in order to detect conductivity in tibial nerve 78 or in another target nerve.

Figure 6C:
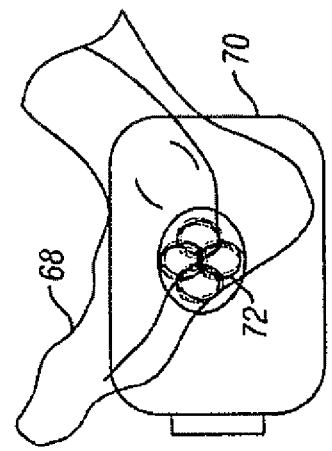

During a third step illustrated in FIG. 6C, a healthcare provider analyzes conductivity measurements provided by sensor 74 (for example, by reading gauge 77) and first adjusts the positioning of coils 72 until conduction in nerve 78 is detected. For example, the healthcare provider may rotate a knob 80, slide a lever or actuate any other displacement system for coils 72 that is known in the art, so that coils 72 are translated until a magnetic field of the proper amplitude and intensity is applied to cause conduction in nerve 78. The position of coils 72 is then fine-tuned manually until an optimal level of conduction in nerve 78 is attained, and the therapy is continued for a length of time as prescribed by the attending healthcare provider.

Figure 6D:
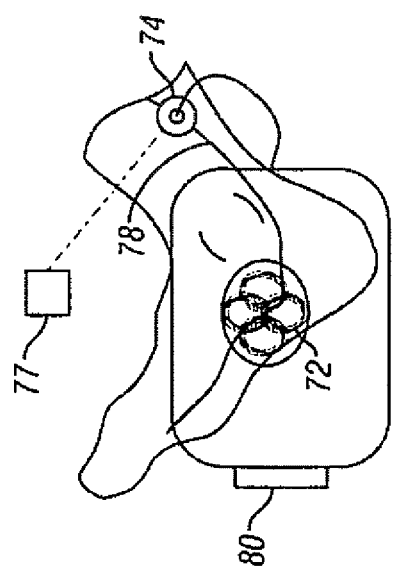

During a fourth, optional step illustrated in FIG. 6D, settings for successive therapy sessions are set, for example by locking knob 80 (in one embodiment, with a pin 81) so that the healthcare provider or the patient repeat the therapy using the predetermined settings. Alternatively, the patient may be trained to adjust the amplitude and/or strength of the applied magnetic field, as each therapy session requires.

While the present method has been described with regard to foot cradle 70, the same method steps may be envisioned for coil wraps or cradles of different configurations, for example, for the coil wraps and cradles described with reference to the previous figures.

In an alternative embodiment, the logic controller (not shown) may automatically adjust coil positioning to optimize therapy during the initial and successive sessions. While this set-up may be more difficult to implement, it also provides for an accurate targeting of the target nerve during each therapy session, regardless of alterations in patient positioning or changes to the anatomy of the patient (for example, when a foot is swollen). In this embodiment, the device simply varies the orientation of coils 84 until stimulation has been sensed.

Further, coils 84 may be translated along a single direction (for example, horizontally) or along a plurality of directions, to provide for the most accurate positioning of coils 84 with respect to the target nerve.

A second method of use of the foot cradle depicted in FIG. 4 is described now with reference to FIG. 7. While this second method is also described with reference to a foot cradle 82 employing one or more coils 84 that have a reversibly lockable, adjustable orientation, the present method may be equally implemented with a body-worn coil wrap, such as those described with reference to the previous figures, or to other embodiments. In this method, the patient or the healthcare provider adjusts the positioning of coils 84 to detect conductivity in target nerve 89.

The position of coils 84 may be translated in different directions (in the illustrated embodiment, may be translated horizontally) and may be locked in an initial position once conduction in nerve 89 is detected by a sensor (for example, sensing patch 86)

Figure 7A:
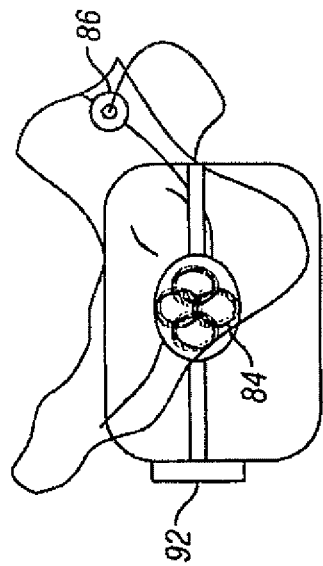
FIGS. 7A-7D are schematic illustrations of a second method of use of an apparatus for magnetic induction therapy. This method is based on locking the conductive coils in position once electrical conduction in a target nerve has been detected.
Figure 7B:
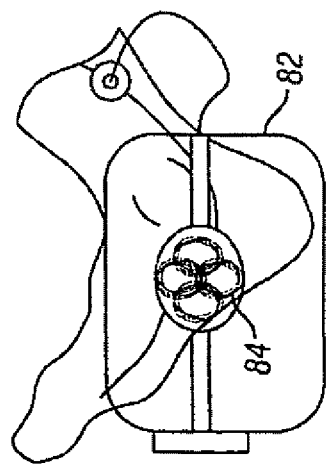

More particularly, FIG. 7A illustrates the initial positioning of foot 88 into cradle 82 and of sensor patch 86 on ankle 90 or other appropriate body part of the patient. After proper positioning of foot 88 is attained, a knob 92 (or other equivalent device) may be employed to adjust the position of coils 84, based on the signals (for example, nerve conduction signals) provided by sensor patch 86, as shown in FIG. 7B.

Figure 7C:
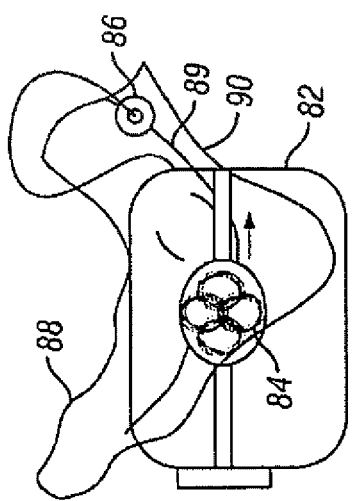
Figure 7D:
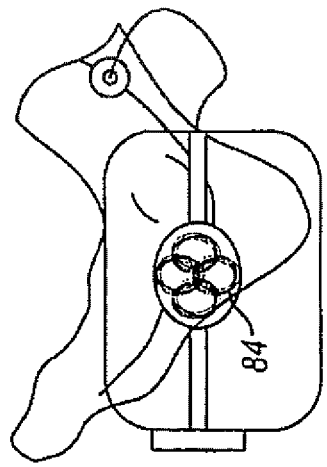

With reference to FIG. 7C, after neural conduction is detected, coils 84 are locked in place, and, with further reference to FIG. 7D, foot cradle 82 retains coils 84 locked in position for further use in a home or healthcare office environment. Therefore, in the present method, the patient or a healthcare provider simply adjusts coil position by sliding coils 84 back and along one axis until electric conduction in the target nerve is detected, although adjustments along all three axes may be possible in different variants of the present embodiment.

Figure 8:
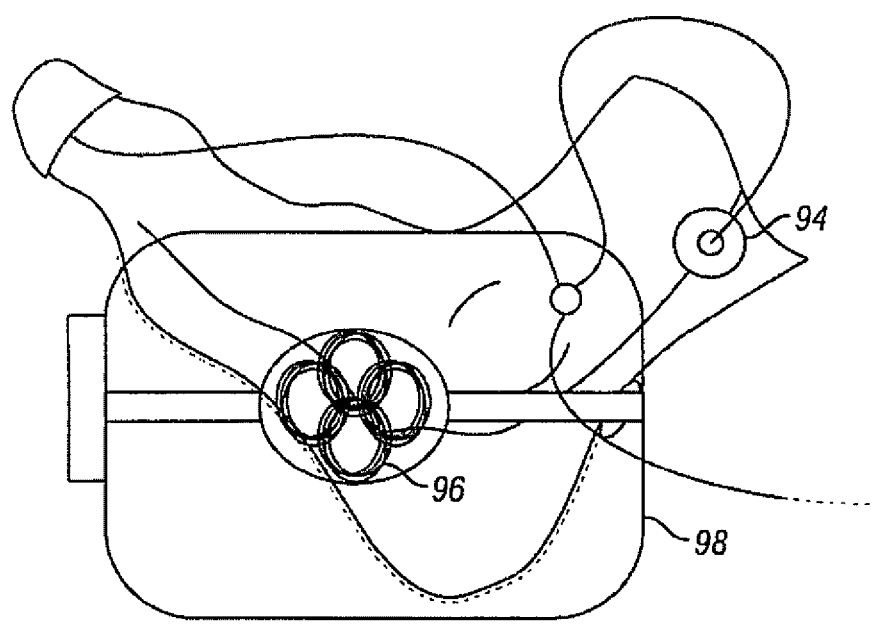
FIG. 8 is a schematic view of an embodiment that includes a plurality of sensors.

Referring now to FIG. 8, a sixth embodiment relates to the use of multiple sensors. While FIG. 8 depicts an embodiment shaped as a foot cradle 98, it should be understood that the following description also relates to any other design, whether shaped as a cradle or a wrap or otherwise. The plurality of sensors 94 described herein may detect a variety of physiologic changes, including neural impulses, muscular contraction, twitching, etc. that may occur with neural or muscular stimulation.

One or more of the illustrated sensors 94 may be employed over body regions being stimulated (for example, back, leg, arm, neck, head, torso, etc.) and may be either incorporated within an actual cradle or wrap or, otherwise, be applied separately from the cradle or the wrap.

Sensors 94 may be structured as disposable, single-use, EKG-type patches that are attached to the body outside of cradle 98 along the nerve conduction pathway and are then connected to the logic controller (not shown) before beginning therapy. This arrangement provides for an intimate body contact of sensors 94 without the risk of infection or other detrimental side effects that may be present with transcutaneous devices. Sensors 94 may be employed both for beginning and for monitoring the stimulation therapy; more specifically, sensors 94 may be employed during the beginning of the therapy to optimize the strength of the magnetic field and/or to adjust the positioning of coils 96 within the cradle 98. Once therapy has begun, sensors 94 continue to monitor nerve conduction to ensure that the correct level of stimulation is being provided. In the event that for some reason nerve conduction decays during therapy, the logic controller can automatically adjust the magnetic field, ensuring that the appropriate therapy is delivered for the appropriate amount of time.

One or more of sensors 94 in this embodiment, or any of the embodiments described herein, may take the form of an inductive coil designed to receive impulses from the underlying nerves, so that inductive technologies may be used to both stimulate the nerve or tissues as well as to record the effect of the stimulation on nerves or tissues. Any of sensors 94 may be connected to the logic controller through one or more connection modes, including, but not limited to, wireless signals, wired signals, radio frequencies, Bluetooth, infrared, ultrasound, direct switching of the current circuit, etc., so long as communication between the sensor and the device is effective.

During implementation of the present method, a healthcare provider may simply elect to use sensors 94 to adjust the device, for example, to lock coils 96 into position, during the first therapy session and not require the use of sensors 94 during each successive therapy session.

Referring now to FIGS. 9A-9D, there are shown different, non-limiting embodiments shaped as body worn ergonomic applicator garments. Each of these embodiments is shown with overlapping coils, although coils of any configurations may be used. Each of the wraps of FIGS. 9A-9D corresponds to a coil wrap, into which a body part may be placed. These garments contain one or more sensors (not shown) that provide feedback to a logic controller (also not shown), or sensors may be applied separately from those garments. Systems may also be included for reversibly or irreversibly locking the coils within the applicator.

More particularly, FIG. 9A illustrates an embodiment, in which coils 100 are embedded in a knee wrap 102 and are connected to a logic controller (not shown) by a connector 104. FIG. 9B instead illustrates an embodiment, in which coils 106 are disposed within an abdominal garment, for example shorts 108 and in which coils 106 are also connected to a logic controller (not shown) by a connector 110. A marking 112 may be added on one side of shorts 108 to indicate wrap orientation. FIG. 9C illustrates a coil wrap shaped like a band 114, in which coils 116 are connected to a logic controller (not shown) by a connector 118. When this embodiment is employed, band 114 may be wrapped around a body portion (for example, an arm) and be retained in place by a system known in the art, for example, a hook and loop system, a strap and buckle system, or simply a hook disposed at one end of band 114 for engaging fabric or other material in another portion of band 114. FIG. 9D illustrates an embodiment shaped as a shoulder strap 120, the length of which may be adjusted by a buckle 122 and which has coils 124 disposed in one or more points, for example, at the joint between an arm and a shoulder as shown. Each of these embodiments includes one or ore sensors (not shown) that may be coupled to the garment, or that may be applied separately from the garment.

Other embodiments that are not illustrated include, bur are not limited to: a head worn garment, such as a cap; a neck worn garment, such as a neck brace; and a lower-back garment. Each garment and applicator may also utilize the locking, targeting coil feature described previously, without requiring the use of the any sensing components after a proper positioning of the coils in relation to the target nerve or nerves has been established.

Figure 10:
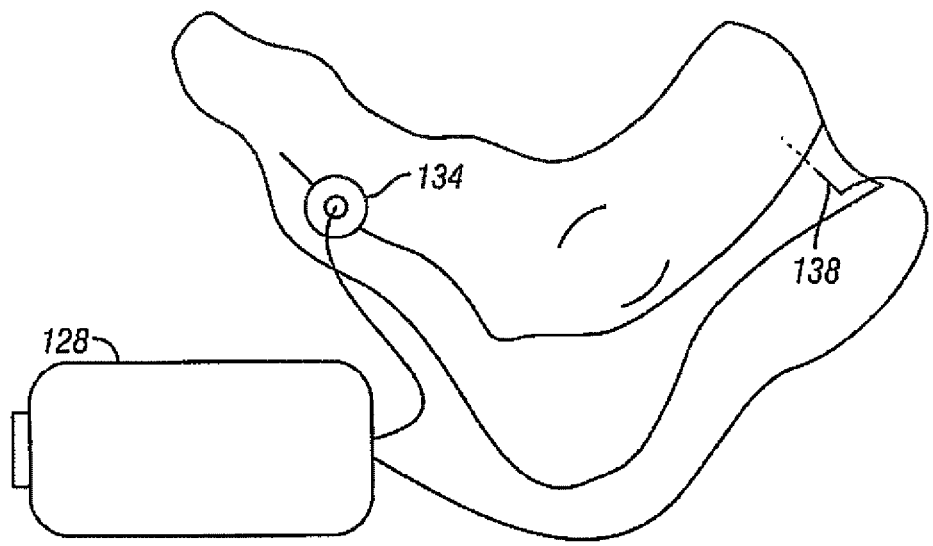
FIG. 10 is a schematic view of an apparatus for providing electrical stimulation.
Figure 11:
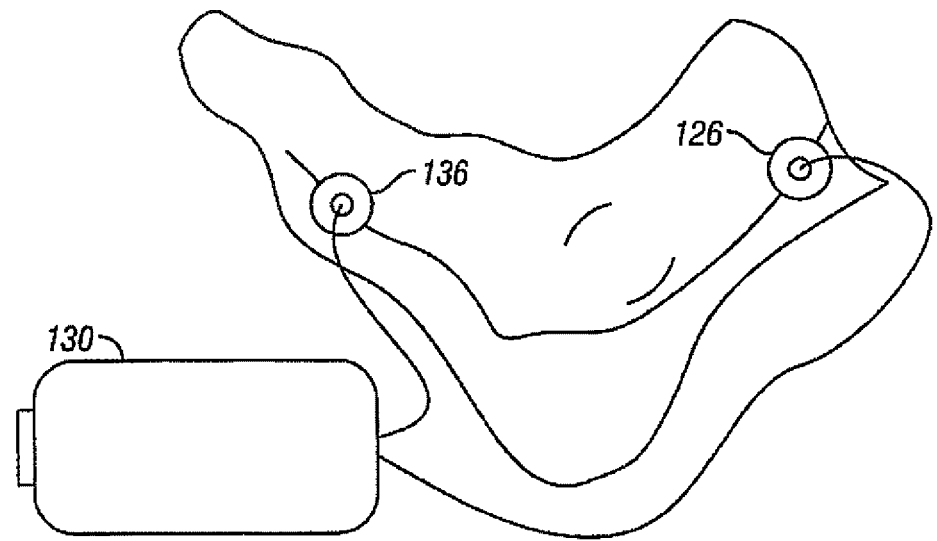
FIG. 11 is a schematic view of another embodiment of an apparatus for providing electrical stimulation.

Still other embodiments are depicted in FIGS. 10 and 11. In these embodiments, the source of energy for nerve stimulation is electrical energy that is dispensed through a percutaneous stimulator, such as a percutaneous needle 124, or a transcutaneous stimulator, such as an electrode 126. As shown in FIG. 10, an electrical pulse controller 128 is electrically connected both to percutaneous needle 124 and to sensor 134, to provide the desired feedback and modulate the power to percutaneous needle 134. In the embodiment of FIG. 11, electrical pulse controller 130 is connected both to electrode 126 and to sensor 136, and performs a function similar to that of electrical pulse controller 128. With these embodiments, nerve conduction may be detected at a site sufficiently distant from the site of stimulation, so to enable detection of nerve conduction despite the confounding interference from the direct electrical stimuli. Further, direct electrical stimulation of nerve and muscle may be tailored to provide optimal therapy and, in the case of electrode migration or other electrode malfunction, to report lack of stimulation of the bodily tissues. Still further, these embodiments enable a reduction in power requirement, because control of the signal is provided by the sensor to the signal generator loop.

As shown, a device constructed according to the principles described herein can provide a targeted and precise stimulation of the posterior tibial nerve, or of other peripheral nerves, in a non-invasive manner by employing an ergonomic wrap or cradle that specifically targets the posterior tibial nerve in a consistent and repeatable manner. For example, in patients with OAB or VI, the novel, reversibly lockable movement of the coils and the use of a logic controller-sensor loop enables the application of a magnetic field that can be varied in location, amplitude and strength according to the amount of stimulation actually induced in one or more target nerves and of the response of the patient to the therapy. An apparatus according to certain embodiments described herein may deliver any frequency of stimulation, including low frequencies, high frequencies, mid frequencies and ultrahigh frequencies, and overlapping and non-overlapping coils may be used to generate the desired field, although overlapping or Helmholtz coils are preferred due to their ability to target a broader region and achieve more thorough stimulation.

Ailments that may be treated through the use of the various embodiments of the apparatus and methods described herein include not only OAB and VI, but also obesity, depression, urinary incontinence, fecal incontinence, hypertension, pain, back pain, restless leg syndrome, Guillain Barre syndrome, quadriplegia, paraplegia, diabetic polyneuropthy, dyskinesias, paresthesias, dental procedure pain, knee osteoarthritis, anesthesia (pain relief during surgery), Alzheimer's disease, angina (chest pain from heart disease), ankylosing spondylitis, back pain, burn pain, cancer pain, chronic pain, dysmenorrhea (painful menstruation), headache, hemiplegia, hemiparesis (paralysis on one side of the body), labor pain, local anesthesia during gallstone lithotripsy, facial pain, trigeminal neuralgia, bruxism (tooth grinding) pain, myofascial pain, pregnancy-related nausea or vomiting, neck and shoulder pain, pain from broken bones, rib fracture or acute trauma, diabetic peripheral neuropathy, phantom limb pain, post-herpetic neuralgia (pain after shingles), postoperative ileus (bowel obstruction), irritable bowel syndrome, postoperative nausea or vomiting, postoperative pain, post-stroke rehabilitation, rheumatoid arthritis, skin ulcers, spinal cord injury, temporomandibular joint pain, detrusor instability, spinal muscular atrophy (in children), pain during hysteroscopy, gastroparesis, chronic obstructive pulmonary disease rehabilitation, carpal tunnel syndrome, soft tissue injury, multiple sclerosis, intermittent claudication, attention-deficit hyperactivity disorder (ADHD), cognitive impairment, knee replacement pain, achalasia, atopic eczema, bursitis, carpal tunnel syndrome, dementia, depression, dry mouth, dystonia, enhanced blood flow in the brain, enhanced blood perfusion of the uterus and placenta, esophageal spasm, fibromyalgia, fracture pain, Guillain-Barre syndrome, hemophilia, herpes, hip pain, interstitial cystitis, irritable bowel syndrome, pruritis, joint pain, labor induction, local anesthesia, menstrual cramps, muscle cramps, muscle spasticity, muscle strain or pain, musculoskeletal trauma, myofascial pain dysfunction syndrome, nerve damage, osteoarthritis, pain medication adjunct, pancreatitis, Raynaud's phenomenon, repetitive strain injuries, sacral pain, schizophrenia, shingles, shoulder subluxation, sickle cell anemia pain, Skin flap ischemia (during plastic surgery), sphincter of Oddi disorders, sports injuries, thrombophlebitis, tinnitus (ringing in the ear), restless legs, tremor, whiplash and neuralgias. In contrast to implantable nerve stimulators, this therapy is completely non-invasive and does not require a major surgery to implant a permanent nerve stimulation device. Moreover, this therapy can be controlled to optimize the level of therapy delivered according to power consumption and nerve stimulation requirements and need not be delivered by a professional healthcare provider.

In other embodiments, neural stimulation may be applied as electrical transcutaneous stimulation, for example, by inserting an invasive electrical needle into a target body part and by modulating stimulation is modulated on the basis of information sent back to the logic controller from the one or more sensors that are used to detect and/or maintain the correct level of stimulation. The transcutaneous electrical stimulation sensor may be placed in the body independently or be incorporated within the wrap and may provide, among other things, feedback as to the quality of the electrical connection to the skin, which is directly related to the burn risk inherently associated with this type of therapy. In fact, these methods of stimulation may not be optimal due to the resulting skin irritation and risk of potential burns, a very serious issue in the large percentage of patients that have neuropathies. Even when patches are applied to monitor transcutaneous stimulation very closely, the patches may still become displaced and allow a burn to occur. Moreover, potentially interfering electrical impulses may develop at the treatment site, creating a noisy environment for the detection of nerve conduction.

In still other embodiments, an external coil or coils may be inductively connected to an implanted coil or coils may be utilized. In these embodiments, an ergonomic applicator may be adjusted by the user or by a healthcare provider such to optimize inductive power transmission between the external and implanted coils. One or more sensors may be utilized to provide a feedback that the relative coil positions have been optimized, and the external coil may then be reversibly locked into position within the ergonomic applicator. Two applications of this embodiment relate to the transfer of power to recharge an implantable device, and to the transfer of power to activate an implantable device.

In the first application, when an implantable rechargeable device is utilized, the external coils may be used for recharging the implanted device by means of inductive fields generated by the external coils. The external coils may include circuitry that determines the amount of resistance encountered by the magnetic field or other electrical properties related to the quality and degree of the magnetic coupling that is being established. Based on this feedback, the position of the external coils may be adjusted manually or automatically to optimize the coupling achieved with during each recharging session. Alternatively, a sensor may be incorporated into the implantable device and may communicate the degree and quality of the magnetic coupling to the external coils and/or the connected circuitry via wireless communication, providing a feedback for the automatic or manual adjustment of the external recharging coils.

The coils within the ergonomic applicator may be reversibly locked into place for the duration of the recharge session, and the implantable device may also communicate to the external recharging unit that the implantable device has been fully recharged, terminating the recharging session has been completed. By providing for an intermittent recharging of an implanted device, an apparatus according to various embodiments described herein can enable the implantable device to devote more power to performing its intended function optimally and with a lesser concern about protecting or extending battery life.

In the second application, the powering coils may contain circuitry to determine the amount of resistance encountered by the applied magnetic field, or other electrical properties that may reflect the quality and degree of the magnetic coupling that is being achieved. Based on this feedback, the powering coils in the applicator may be adjusted manually or automatically to activate and optimize the coil coupling at the beginning of each therapy session. Alternatively, a sensor may be incorporated into the implantable device and communicate the degree and quality of the magnetic coupling externally via wireless communication, which may in turn provide feedback for the automatic or manual adjustment of the powering coil. In one variant of the present embodiment, the inductive coils may be magnetically coupled to a needle targeting the posterior tibial nerve.

An exemplary method of use of an apparatus according to the embodiments described herein on a patient suffering from VI and/or OAB includes the following steps:

The patient places a conductive wrap contained within a flexible material over a region of the ankle (or alternatively over the knee) to provide the required pulsed magnetic field. Alternatively, the patient may use an ergonomic foot/leg rest or cradle having embedded coils.

A sensor (for example, a sensor patch) is placed on the patient's body along the path of the nerve, ideally proximal to the stimulation site to ensure afferent nerve stimulation, and is connected to a logic controller.

A physician or healthcare provider adjusts the coils in the wrap or cradle until nerve conduction is achieved based on patient and sensor feedback. An optimal position is sought, and the coils may be reversibly locked into position within the conductive wrap or ergonomic cradle and remain in this position during subsequent use.

During the therapy session, the logic controller provides an electric current to the coils, generating an inductive magnetic field. In one embodiment, this field begins at low amplitude and slowly ramps up until nerve conduction exceeds a threshold level, as signaled by the sensor and possibly by the patient, who may feel motory conduction. Alternatively, one or more coils may also be activated to increase the covered area of stimulation in the event that stimulation does not occur with the initial coil configuration or is inadequate The optimal stimulation may be determined in a variety of manners, for example, by measuring exposure to electromagnetic fields capable of generating a square wave electric signal at a frequency of 10-30 Hz at the targeted tissue depth. The square wave configuration of the signal may be generated via Fourier transformation or may be a ramped current generated in any manner.

The inductive magnetic pulses continue for an appropriate duration of use, for example, for 15-30 minutes. The sensor may remain in place during the entire therapy session to ensure that stimulation occurs consistently and to provide for appropriate corrections if nerve conduction deteriorated. The logic controller may be powered either by a portable power source such as a battery, or by or a fixed power source such as a traditional wall outlet.

The conductive wrap and/or ergonomic cradle is removed from the body when therapeutic stimulation is not being delivered, typically at the end of the therapy session.

The conductive wrap and/or ergonomic cradle is reapplied along with the sensor patch (ideally disposable) from time to time as indicated, for example, on a daily basis, and steps 4-8 are repeated.

The devices and methods described herein may be applied to any body tissues, including nerve, muscle, skin, vasculature, or any other organ or tissue within the human body. Further, the devices and methods described herein may be used to treat any conditions suited for neuromodulation regardless of whether the stimulation source is an electromagnetic field, a direct electric current, a RF field, infrared energy, visible light, ultraviolet light, ultrasound, or other energy dispensing device.

Figure 12:
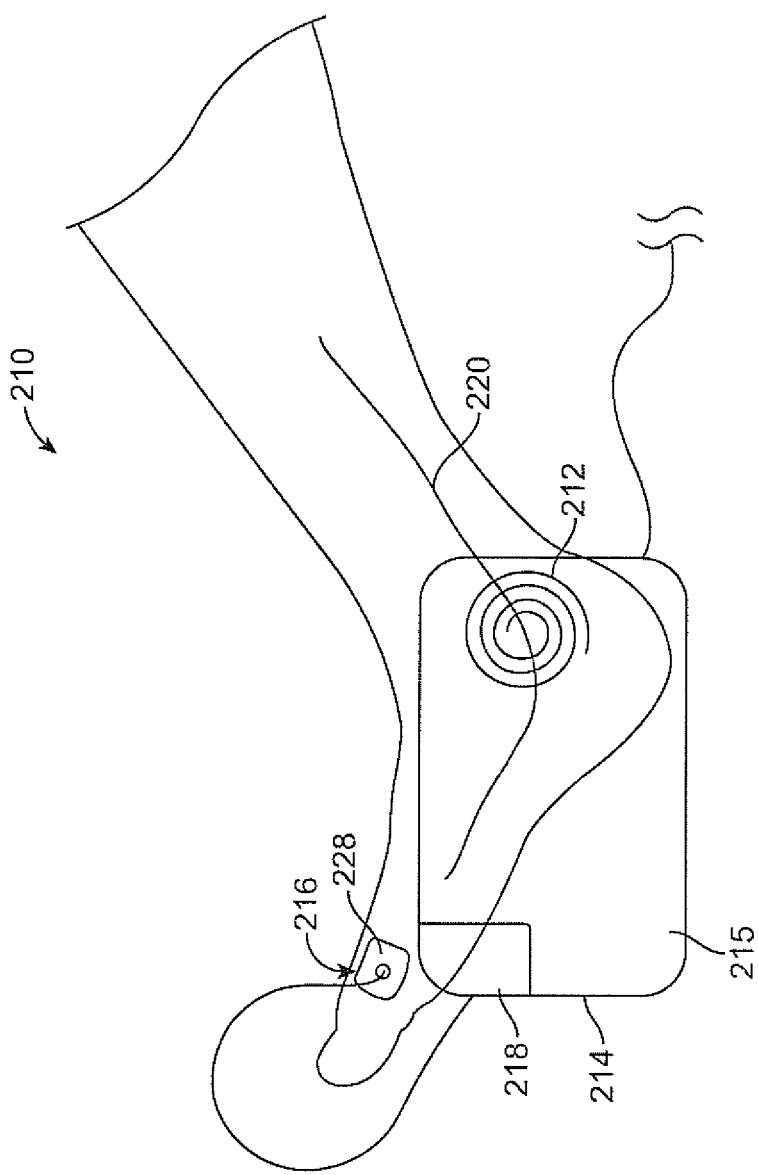
FIG. 12 shows a schematic view of an energy emitting system including a microneedle patch sensor.

In other embodiments, as shown in FIG. 12, an energy emitting system 210 for providing a medical therapy may include one or more conductive coils 212 disposed within or along a housing 214, one or more sensors 216 configured to detect electrical conduction in a target nerve or to detect muscle stimulation, and/or a controller 218 coupled or connected to the conductive coils 212 and optionally in communication with the sensor 216. The coils 212 are configured such that an electrical current generated by the controller 218 is passed through the coils 212 generating a magnetic field which will stimulate a target nerve, e.g., the tibial nerve 220, a muscle or other body part containing a portion of a target nerve, or any nerves branching off of a target nerve, located in proximity to the coils 212. In this particular embodiment, the housing 214 is in the form of a foot cradle, as shown in FIG. 4, however, the housing could also be in the form of a flexible wrap, garment or other design suitable for use with a subject. In various embodiments described herein, sensors may detect voltage or current and may be connected, coupled, wirelessly connected or coupled or otherwise in communication with the housing and/or controller using a variety of methods or techniques known in the art. The sensor may be placed over a muscle to detect muscle stimulation as a result of stimulating the target nerve (as shown in FIG. 12) or over any other portion of the subject's body suitable for detecting conduction of the target nerve.

Figure 13:
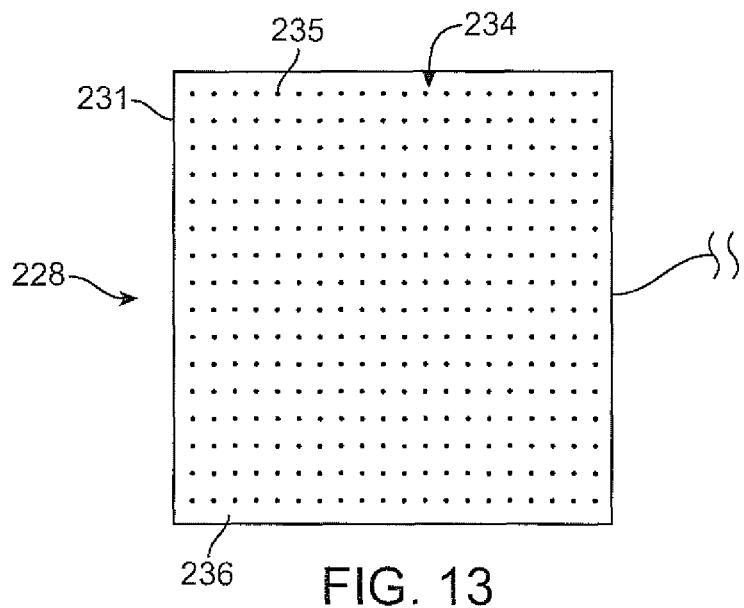
FIG. 13-15 shows magnified bottom views of various embodiments of microneedle patches.
Figure 14:
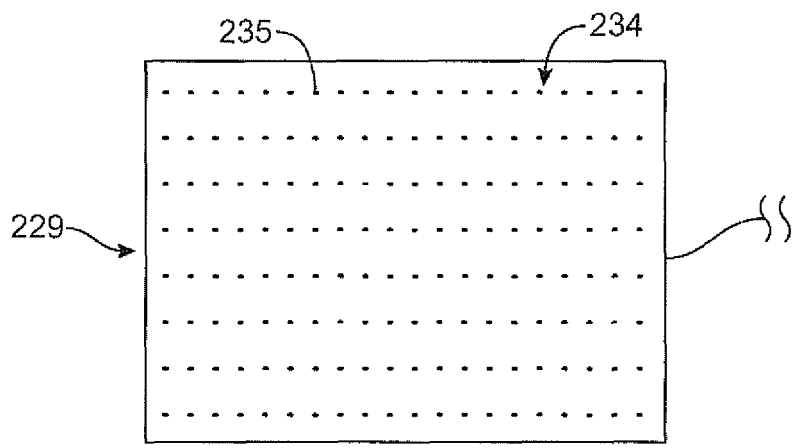
Figure 15:
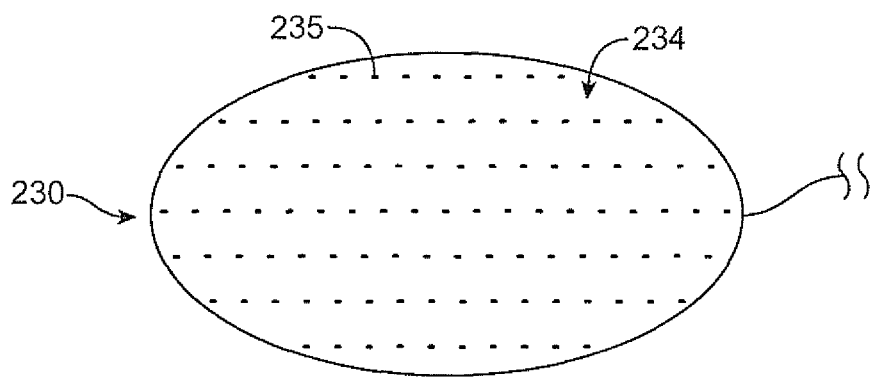
Figure 16:
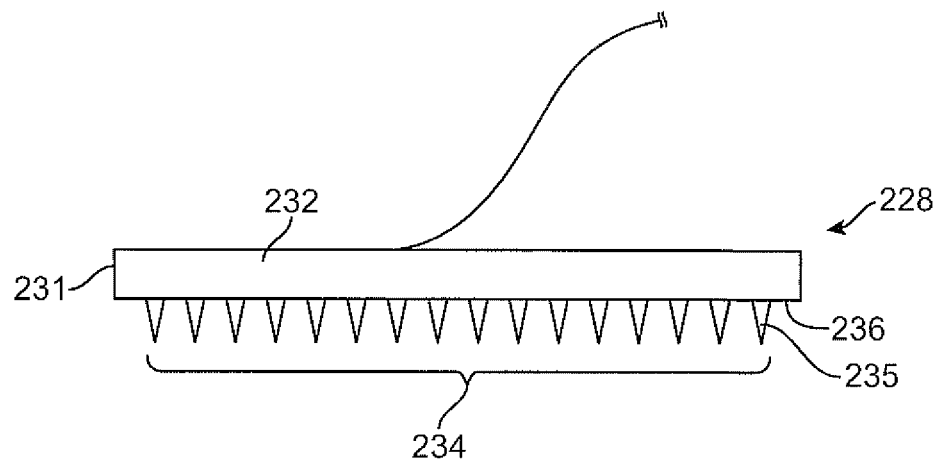
FIGS. 16-17 shows magnified side views of various embodiments of a microneedle patch.

Referring to FIGS. 13 and 16, the sensor may be in the form of a microneedle patch 228, which can be removably attached to the skin surface of a subject. The microneedle patch 228 may include a housing 231, having one or more electrodes 232 and one or more microneedles 235 deposited or arrayed on a surface of the electrode 232, forming one or more microneedle arrays 234. In FIG. 13, microneedle patch 228 has the shape of a square, and the microneedles 235 are arrayed on the bottom surface 236 of the electrode 232 in a 16×16 configuration. However, as shown in FIGS. 14-15, microneedle patches may be designed in a variety of shapes, e.g., round, oval 229, rectangular 230, hexagonal, and a variety of sizes. The microneedles may be arrayed in a variety of arrangements and patterns (e.g., 14×14, 12×12, etc.) depending on the particular use and needles.

Additionally, microneedles may be attached, deposited, or arrayed on an electrode surface or patch in a variety of configurations and arrangements, depending on where the particular microneedle patch will be utilized and the treatment to be delivered. The number of microneedles included in an array can vary. For example, the number of microneedles may range from about 5 to 500 or 100 to 400 or about 200 to 300 or about 256. In certain embodiments where microneedles are composed of strong, highly conductive material, the number of microneedles necessary may be less and may range from about 5 to 100 or 10 to 50 or 5 to 50. However, where microneedles are composed of higher resistance metal, a greater number of needles may be needed, e.g., about 100 to 500 or about 200 to 300 or greater than 500.

Figure 17:
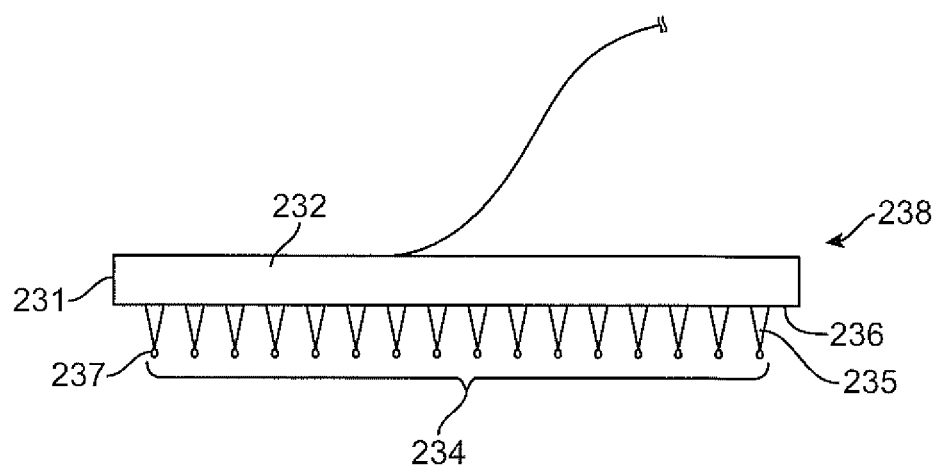
Figure 18:
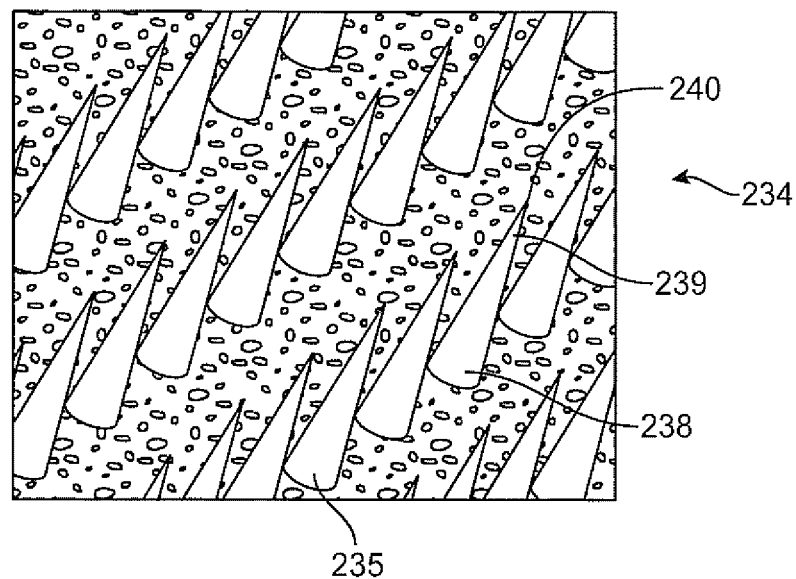
FIG. 18 shows a magnified bottom perspective view of a microneedle patch.

Referring to FIG. 18, a magnified view of a microneedle array 234 composed of one or more microneedles 235 is shown. Microneedles 235 may include a base portion 238 and an upper portion 239. Microneedles 235 may have lengths in the range of about 1 to 400 microns or 10 to 400 microns or preferably about 100 to 150 microns, and a diameter in the range of about 1 to 100 microns. A microneedle 235 may be tapered in diameter, going from a larger to smaller diameter from the base portion 238 to the upper portion 239 where the distal tip 240 of the microneedle is preferably pointed or sharp. The upper portion 239 of the microneedle 235 may have a diameter in the range of about 10-30 microns or about 15 to 25 microns. Optionally, for ease of production, the base portion 238 of the microneedle 235 may be thicker than the distal tip 240 or upper portion 239 of the microneedle 235. In certain embodiments, as shown in FIG. 17, a bulb 237 may be provided at the distal tip 240 of a microneedle 235 to provide for effective anchoring of the microneedle 235 in the skin of a patient or subject. Microneedles 335 can include any number of friction or grip increasing features. For example, they may include projections, barbs, bulbs or a roughened surface or tip. Microneedles 235 may take on various configurations, e.g., straight, bent, filtered, hollow or a combination of the above.

In other embodiments, microneedles may have lengths that range from about 480 to 1450 microns, widths from about 160 to 470 microns, thicknesses from about 30 to 100 microns and tip angles from about 20 to 90 degrees, and arrays can contain from 5 to 50 microneedles. For example, microneedles having these dimensions have been shown to be less painful than hypodermic needles. Length and number of microneedles can affect the level of pain experienced. Decreasing microneedle length and/or the number of microneedles may be beneficial and act to further reduce pain and provide comfort.

In certain embodiments, the one or more microneedles may include an electrically conductive material such that the microneedles may transmit an electrical signal to an overlying electrode or other surface. Microneedles may be constructed of an electrically conductive material and/or coated with an electrically conductive material. Optionally, microneedles may be coated with an electrically conductive material and constructed of a non-conductive material. Microneedles may be fabricated using a variety of materials, e.g., metals, stainless steel, solid or coat of gold over NI, Pd or Pd—Co, Pt, silicon, silicon dioxide, polymers, glass, biocompatible polymers, titanium, silver, or suture materials. Biodegradable polymers may also be used such that if a tip of a microneedle were to snap or break off during insertion, it would easily biodegrade.

A microneedle array 234 may be constructed or fabricated using any variety of manufacturing methods known to persons of ordinary skill in the art. Microneedles may be arrayed, attached, etched or deposited onto a surface of an electrode. In another embodiment, microneedles may be etched from or deposited onto a silicon electrode, such that the microneedle patch, including electrode and microneedles, are made from one material creating a durable and stable microneedle patch.

As shown in FIG. 18, microneedles may be fabricated by creating micron sized holes on a silicon substrate and by using a KOH solution to create the needle shape. In other embodiments, the microneedles may be made of non-conductive material but may still be utilized to provide superior anchoring properties such that a microneedle patch may effectively adhere or attaché to a subject's skin.

In certain embodiments, microneedle arrays are fabricated by patterning SU-8 onto glass substrates and defining needle shapes by lithography. The tips of the needles can be sharpened using reactive ion etching. Optionally, holes may be drilled, e.g., by laser, through the microneedles and base substrate. Holes may be drilled off-center, but parallel to the microneedle axis, terminating in side-opening holes along the needle shaft below the needle tip. If desired, the holes can serve as micro fluidic needle bores for injection or infusion of drugs, medicines, insulin, proteins, nanoparticles that would encapsulate a drug or demonstrate the ability to deliver a virus for vaccinations, etc. to be used separately or in combination with electrical or magnetic therapy. The microneedles may also be coated with nickel by electroplating, which can increase their mechanical strength.

In certain embodiments, microneedle patches or microneedle electrode arrays are made by fabricating master structures from which replicates are molded and then made electrically active. For example, SU-8 may be spun on a glass substrate bearing an array mask pattern, baked, and then exposed from the backside to from a tapered needle structure. Microneedles may be sharpened by RIE etching. A PDMS (polydimethylsiloxane) or similar material mold can then be copied from the master. A PMMA (polymethylmethacrylate) microneedle array is formed by solvent-casting and then released from the mold.

To provide the arrays with electrical functionality, a Ti/Cu seed layer may be deposited on the PMMA array and patterned by excimer laser to electrically isolate adjacent rows. A Ni layer (e.g., about 15 to 30 microns or 20 to 25 microns thick) may be electroplated on the patterned seed layer to enhance structural rigidity. A backside electrical connection to the array may be formed by backside etching of a hole and forming an electrical connection through the hole.

In another embodiment, the microneedle array is arranged in a 16×16 array (i.e., 256 needles). Each needle has a height of about 400 microns and the base diameter is about 100 microns. The pitch between microneedles can be about 250 microns. The microneedle arrays are then coated with metal and laser-etched to provide electrical functionality. Optionally, rows of microneedles can be electrically isolated from each other so that alternating rows can provide alternating electrical polarity. The arrays are also interfaced with a power source. Microneedles may be made of polymer, coated with a metal, and etched to act as alternating electrodes. In certain embodiments, the firing sequence of the microneedles by rows or groups may be varied or configured to alternate.

In certain embodiments, a microneedle array may include one or more microneedles having multiple channels. For example, a multichannel silicon microneedle may be constructed to deliver bioactive compounds into neural or other tissue while simultaneously monitoring and stimulating neurons and nerves.

Figure 19:
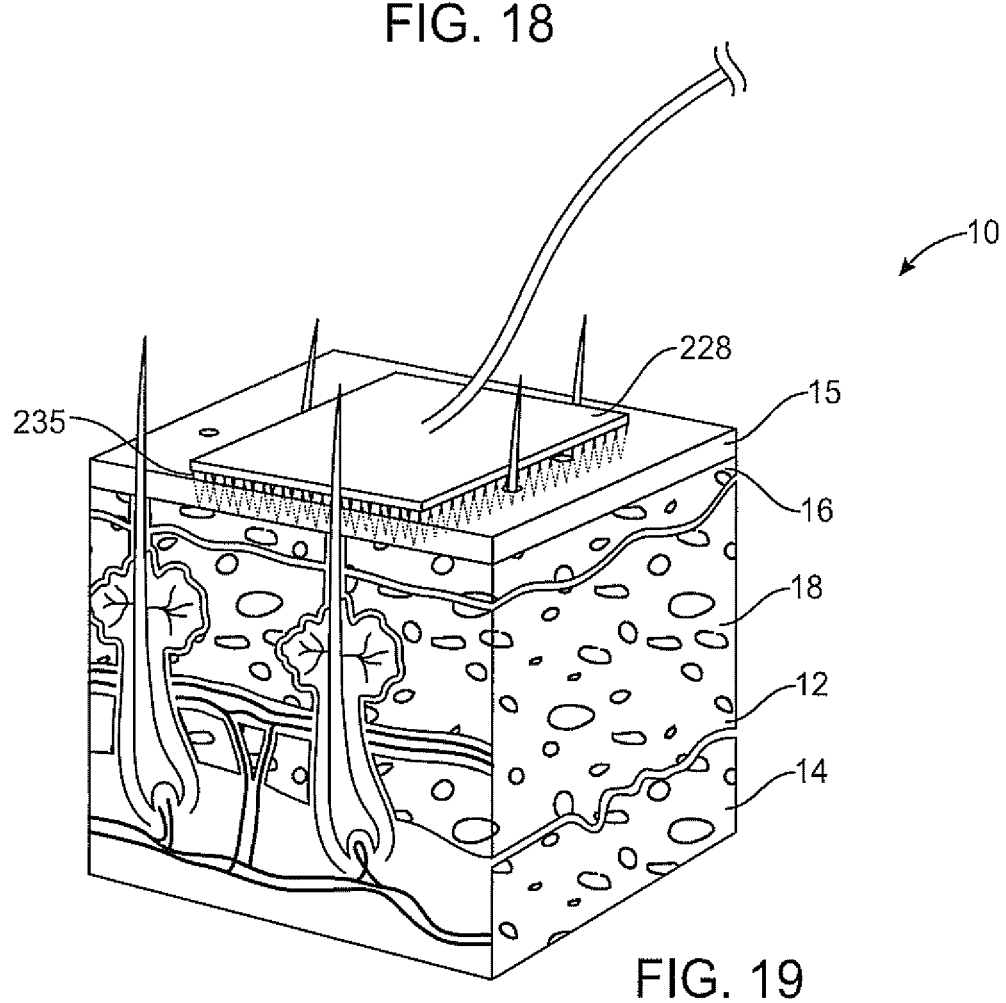
FIG. 19 shows a representative cross sectional view of the skin composed of an outer stratum corneum covering the epidermal and dermal layers of skin and the underlying subcutaneous tissue, with a variation of a microneedle patch attached thereto.

FIG. 19 shows a cross sectional view of the skin 10 composed of an outer stratum corneum 15 covering the epidermis 16. The skin also includes the dermis 18, subcutaneous tissue/fat 12, and these layers cover muscle tissue 14. As shown in FIG. 19, when a microneedle patch 228 is attached to a subject's skin, the microneedles 235 pierce the outer insulating stratum corneum layer 15. The microneedle patch 228 can detect current passing through a stimulated nerve, and provide a superior signal as the current detected is conducted through the microneedles 235, thereby bypassing the poorly conductive stratum corneum layer 15 which generally encompasses the outer 10 to 15 microns of skin. In other embodiments, microneedles 235 may be fabricated to be long enough to penetrate the stratum corneum 15, but short enough not to puncture nerve endings, thus reducing the risk of pain, infection or injury.

In certain embodiments, microneedles are formed such that they are in direct contact with their corresponding or overlying electrodes. For example, a microneedle patch may include an adhesive electrode pad and may utilize a conductive gel to help hold the microneedles in place to prevent shear forces from breaking or bending the microneedles.

Figure 20A:
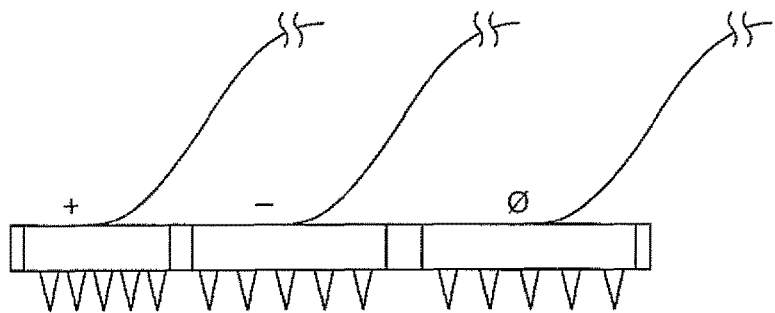
FIG. 20 shows a magnified side view of a variation of a microneedle patch including multiple electrodes.
Figure 20B:
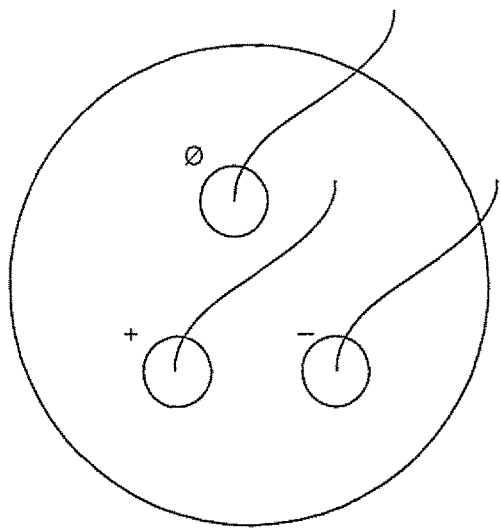
Figure 20C:
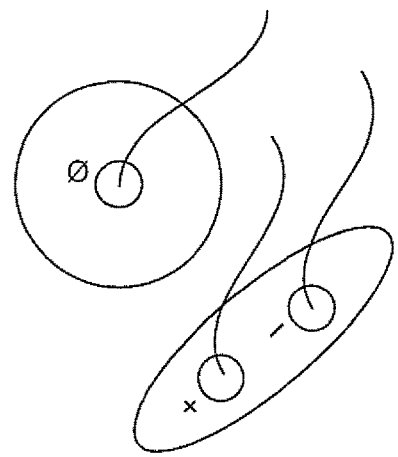
Figure 20D:
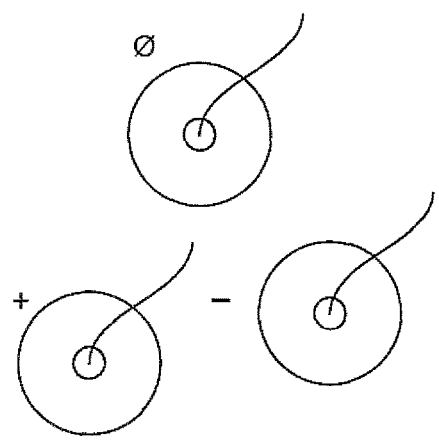

In certain embodiment, as shown in FIGS. 20a-20d, a microneedle patch or applicator may include multiple electrodes on a single patch or applicator, e.g., positive, negative, and/or control or ground electrodes, where the microneedles will be grouped in multiple arrays such that they conduct to the appropriate electrode. For example, FIGS. 20a and 20b show a single patch having positive, negative and control electrodes where a separate array of electrodes is in contact with each respective electrode. This arrangement can be created using a single patch. Alternatively, as shown in FIG. 20c, two patches may be implemented, one including the control electrode with corresponding microneedle array and the other including the positive and negative electrodes with corresponding microneedle arrays. The various electrodes could be interchanged. Alternatively, as shown in FIG. 20d, three patches may be implemented, each having a separate electrode (control, positive, or negative) with a corresponding microneedle array. In use, in certain embodiments, the control may be attached above or near bone, while the positive and/or negative electrodes may be attached above nerve or muscle.

Referring again to FIG. 12, the energy emitting system 210 can be used to treat or prevent various conditions, e.g., urinary incontinence, restless leg syndrome and fecal incontinence, among others. Energy emitting system 210 includes one or more conductive coils 212 disposed within or along a housing 214, one or more sensors 216 configured to detect electrical conduction in the target nerve or to detect muscle stimulation, and a controller 218 coupled to the conductive coils 212 and optionally in communication with the sensor 216. The coils 212 are configured such that an electrical current generated by the controller 218 is passed through the coils 212 generating a magnetic field which will stimulate a target nerve, e.g., the tibial nerve 220, a muscle or other body part containing a portion of a target nerve, or any nerves branching off of a target nerve, located in proximity to the coils 212. In this particular embodiment, the housing 214 is in the form of a foot cradle, as shown in FIG. 4, however, the housing could also be in the form of a flexible wrap, garment or other design suitable for use with a subject.

Referring again to FIG. 12, energy emitting system 210 may be used to treat or prevent various conditions, e.g., urinary incontinence, restless leg syndrome or fecal incontinence. In certain embodiments, a method of using the energy emitting system 210 includes positioning a first portion of a patient's body, for example a foot, ankle, or leg, relative to housing 214 such that a posterior tibial nerve 220 within the first portion of the patient's body is in proximity to one or more conductive coils 212 disposed within or along the housing. In this particular embodiment, a patient's foot is positioned in a housing which is in the form of a foot cradle 215. A sensor in the form of a microneedle patch 228 may optionally be positioned along a second portion of the patient's body in proximity to the posterior tibial nerve 220. In this particular embodiment, microneedle patch 228 is attached to the patient's foot over a muscle to detect muscle stimulation. Alternatively, a patch could be placed elsewhere on the patient, for example, on the leg in proximity to the posterior tibial nerve 220, proximal to and up-stream from coils 212. Microneedle patch 228 may be composed of one or more microneedle arrays and one or more electrodes, as described supra.

Once the patient's foot is in position and the microneedle patch 228 (e.g., conductive microneedle patch) is in place, a current is passed from controller 218 through coils 212, and as a result, the coils 212 generate a magnetic field which is focused on the posterior tibial nerve 220. The magnetic field stimulates tibial nerve 220, generating a current that will flow along the tibial nerve 220 and spread along its length, to its sacral or pudendal nerve roots. Microneedle patch 228 detects corresponding muscle stimulation or twitching or electrical conduction through the stimulated posterior tibial nerve. Upon detection, the microneedle array may conduct and transmit an electrical signal to the overlying electrode of microneedle patch 228. The signal may be transmitted to controller 218, which can be integral or a separate controller or device, or a separate controller coupled to controller 218. The controller can then be varied or adjusted (to adjust the current or magnetic field) based on the signal received from microneedle patch 228 to ensure that adequate conduction of the posterior tibial nerve 220 occurs and an adequate and accurate dosage of treatment is being received. Although shown utilizing a sensor, it is also contemplated that the system could be used without a sensor.

Figure 21:
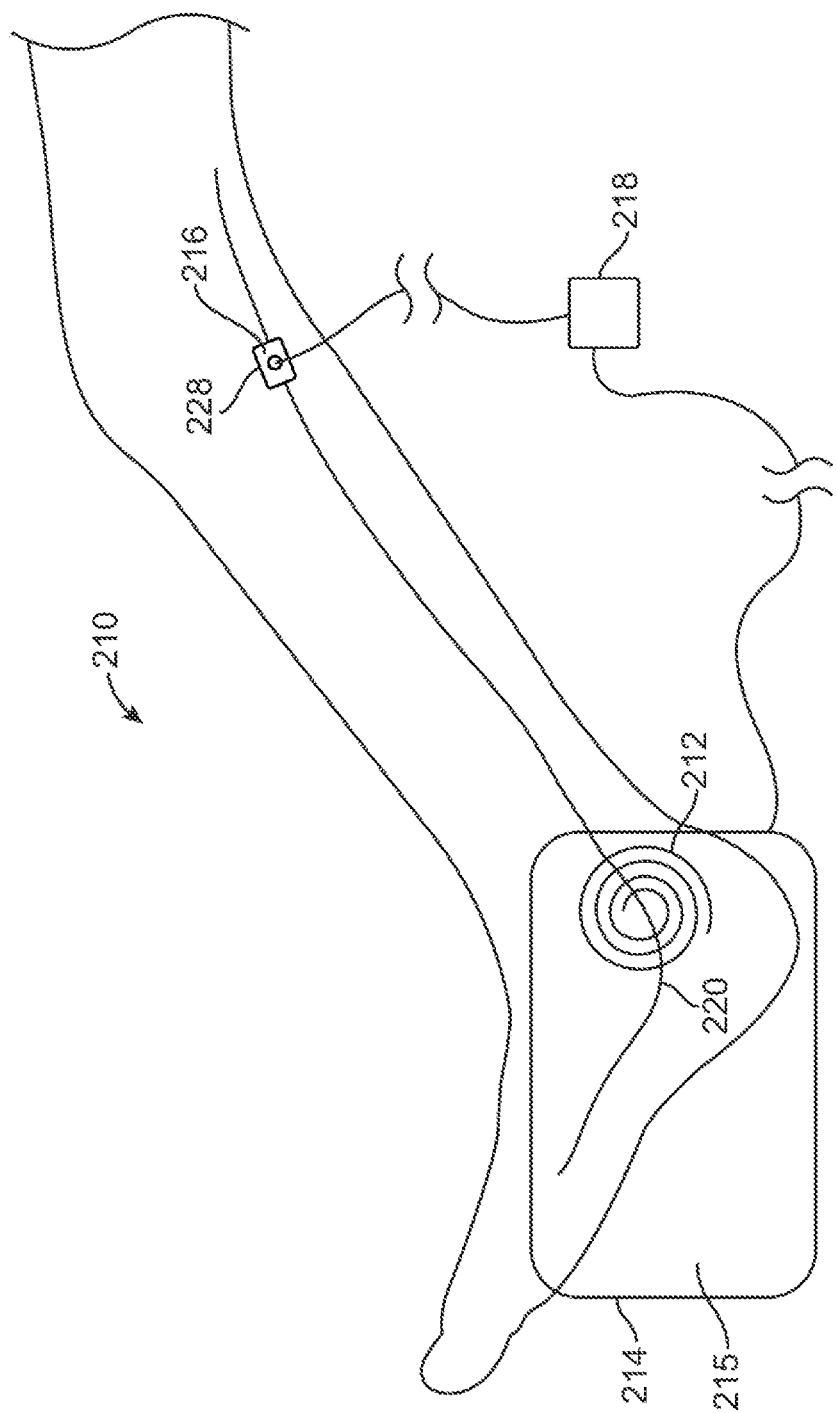
FIG. 21 shows a schematic view of an energy emitting system including a microneedle patch sensor placed behind a subject's knee.

Referring to FIG. 21, the method of using energy emitting system 210 described above with respect to FIG. 12 may be varied such that a conductive microneedle patch 228 is placed in proximity to or proximally over the afferent posterior tibial nerve 220, i.e., behind the patient's knee. In this position, a conductive microneedle patch 228 detects electrical conduction through the afferent posterior tibial nerve, i.e., it detects the electrical signal traveling through the posterior tibial nerve back up to the brain and spinal cord or it may detect corresponding muscle stimulation. The microneedle patch 228 sends the signal to controller 218 or to a separate controller coupled to controller 218. The controller can then be varied or adjusted based on the signal received from microneedle patch 228 to ensure that adequate conduction or stimulation of the posterior tibial nerve 220 occurs and an adequate and accurate dosage of treatment is being received.

A sensor utilized in the energy emitting system 210 may be a microneedle patch 228 as described above or optionally the sensor may be a sensor type known in the art (e.g., EKG sensor) or as described in any of the embodiments described herein. It is also contemplated that energy emitting system 250 can be utilized without a sensor. Optionally, the sensor may be positioned within or along the housing, e.g., the foot cradle, along with the one or more conductive coils, or positioned at a site distant from the housing or conductive coils.

In certain embodiments, energy emitting system 210 my optionally include one or more conductive microneedle patches which can be positioned in proximity to the target nerve or muscle and provide an additional or supplemental electrical or magnetic stimulus to the target nerve or muscle.

Figure 22:
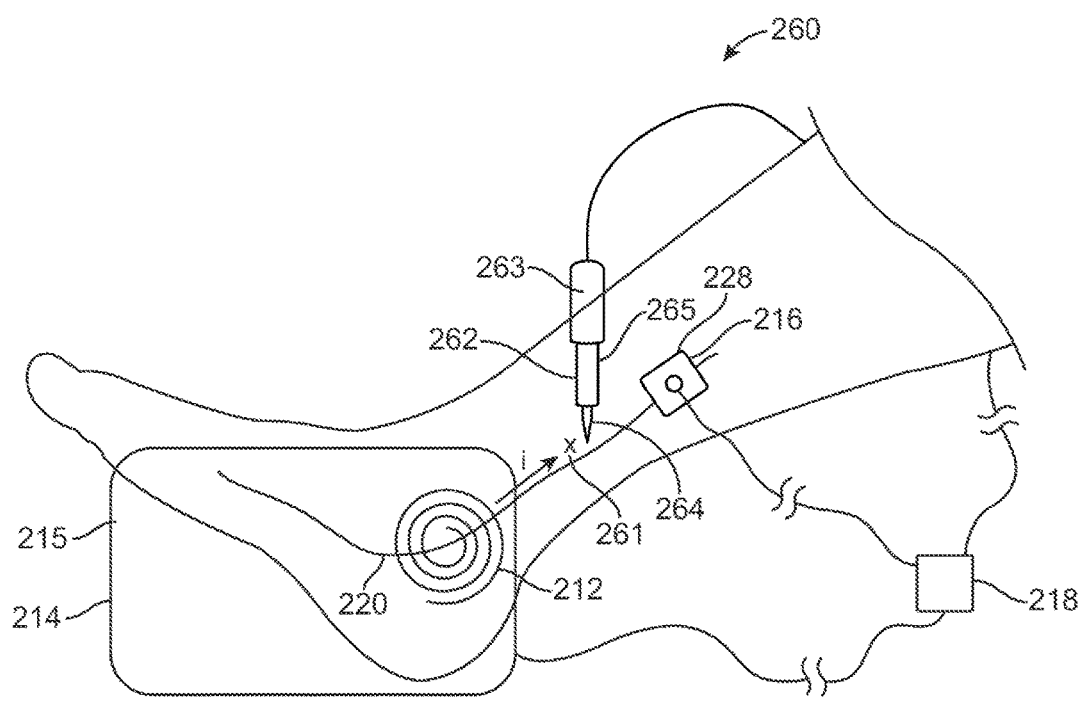
FIGS. 22-23 show schematic views of energy emitting systems including an electrode needle and sensor.

Referring to FIG. 22, the energy emitting system 210 described above with respect to FIG. 12 may be varied to create energy emitting system 260. Energy emitting system 260 further includes one or more percutaneous electrode needles 262 or other needles or other percutaneous electrodes coupled to a controller 218 and having an end insertable into a subject's body in proximity to said target nerve or stimulation site. The percutaneous electrode needle 262 is inductively coupled to one or more conductive coils 212. In use, a first portion of a patient's body, for example a foot, ankle, or leg, is positioned relative to housing 214, e.g., foot cradle 215, such that a target nerve, e.g., posterior tibial nerve 220, located within the first portion of the patient's body is in proximity to one or more conductive coils 212 disposed within or along the housing 214. Conductive coils 212 are positioned proximate, optionally down-stream or distal to, a selected stimulation site 261. The percutaneous electrode needle 262 is inserted through the skin at a location and to a depth that brings the tip in close proximity to the stimulation site or target nerve to be stimulated. The controller 218 is activated and a current passes through conductive coils 212. The resulting magnetic field generates a current that traverses the internal stimulation site 261 by passing from conductive coils 212 to the internal percutaneous electrode needle 262, as indicated by arrow i. Also, the percutaneous electrode needle may be positioned within the generated magnetic field, whereby the magnetic field generates a current in the percutaneous electrode which stimulates a target nerve or traverses an internal stimulation site. Optionally, a current may be passed from the controller 218 through conductive coils 212 and/or from the controller 218 through percutaneous electrode needle 262, traversing the internal stimulation site as the current passes between the coils and needle.

In energy emitting system 260, current density and subsequent electric field intensity generated between conductive coils 212 and percutaneous electrode needle 262 is greater than that generated by traditional percutaneous stimulators. A greater electric field intensity makes site location for conductive coils 212 and percutaneous electrode needle 262 easier. Furthermore, the load impedance through the surface of the skin is much higher than the internal impedance, and as such, the relatively high load impedance lessens the likelihood of damage to tissue and nerves due to high current pulses.

Referring again to FIG. 22, a percutaneous electrode needle for use in any of the energy emitting systems described herein may include a variety of designs. For example, percutaneous electrode needle 262 may include a metal or plastic handle 263 to provide a secure grip for the user, while minimizing the risk of shock to the user. The needle tip can have a terminal portion 264 which may extend between about 0.5 and 10 mm or about 2.0 mm from the needle tip and may be constructed out of medical grade stainless steel or other biocompatible metals. The diameter of the needle can be small (less than about 0.25 mm) which minimizes trauma during insertion. Optionally, needle 262 can be coated with Teflon or similar insulative material 265 except for an exposed tip area 264. This allows for a higher field density at the tip for more precise operation. The exposed needle tip area 264 should have a sufficiently large surface area so as not to create too high a local current field that may cause irritation or pain.

Figure 23:
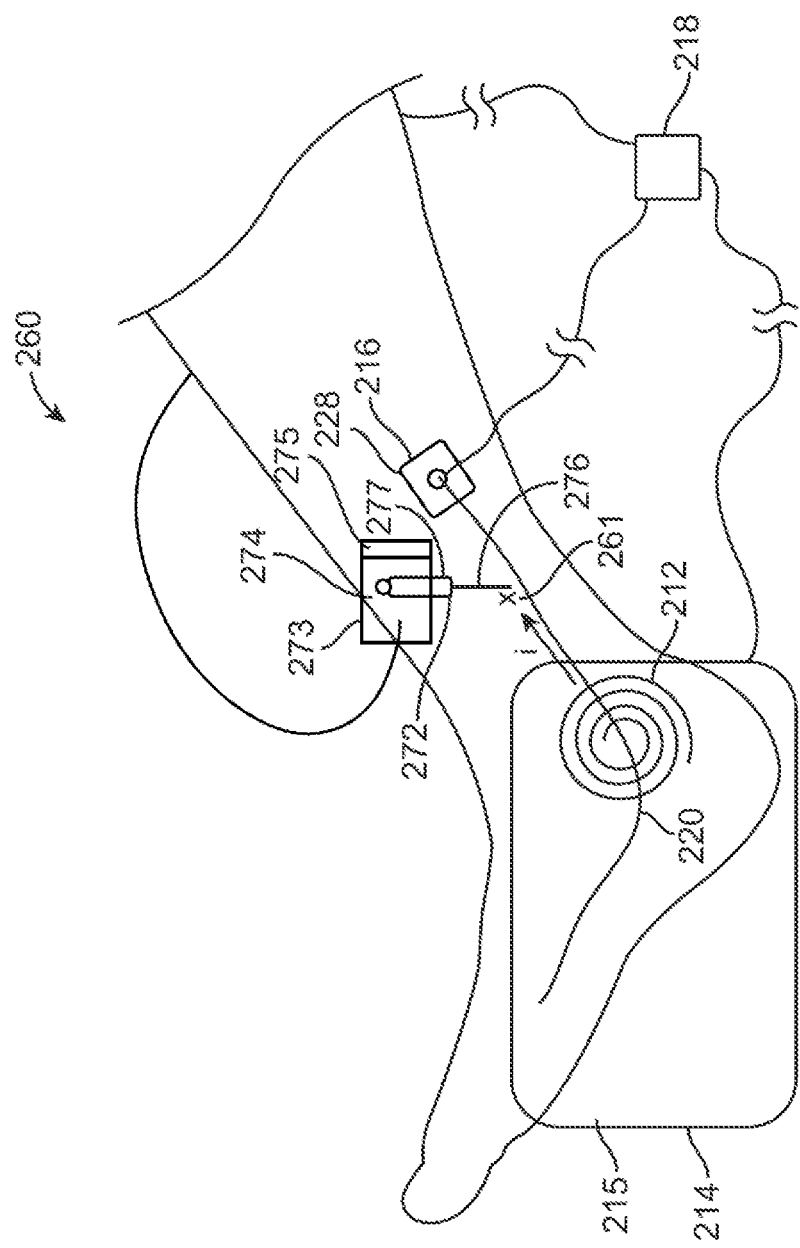

In another embodiment, as shown in FIG. 23, percutaneous electrode needle 272 may be used in energy emitting system 260. Percutaneous electrode needle 272 may be constructed out of medical grade stainless steel or other biocompatible electrically conductive metal. Percutaneous electrode needle 272 includes a first end 276 for insertion into the patient's body in proximity to the preselected internal stimulation site or target nerve to be stimulated, and a second end 277. The size of the needle electrode 272 is preferably small, for example 34 G needle electrode (0.22× 10 mm), to minimize trauma during insertion. Percutaneous electrode needle 272 may also include an electrically conductive adaptor, e.g., an electrically conductive tape member 273. The tape member 273 includes an electrically conductive adhesive portion 274 and an electrically conductive non-adhesive portion 275. Alternatively, the adaptor may include an electrically conductive clip. The second end 277 of the needle electrode 272 preferably includes an enlarged portion to enable the electrically conductive tape member 273 to be more easily adhered thereto. Once it is determined that the percutaneous needle electrode 272 is properly positioned, the needle is fixedly adhered to the electrically conductive tape member 273 by folding the ends of the adhesive portion 274 of the electrically conductive tape member 272 over the second end 277 of the needle electrode thereby forming an electrical connection there between. The percutaneous needle electrode 272 is electrically coupled to controller 218 via electrically conductive tape member 273. Various other implantable or insertable electrode needles known to persons of skill in the art may also be utilized in the above described systems.

Figure 24:
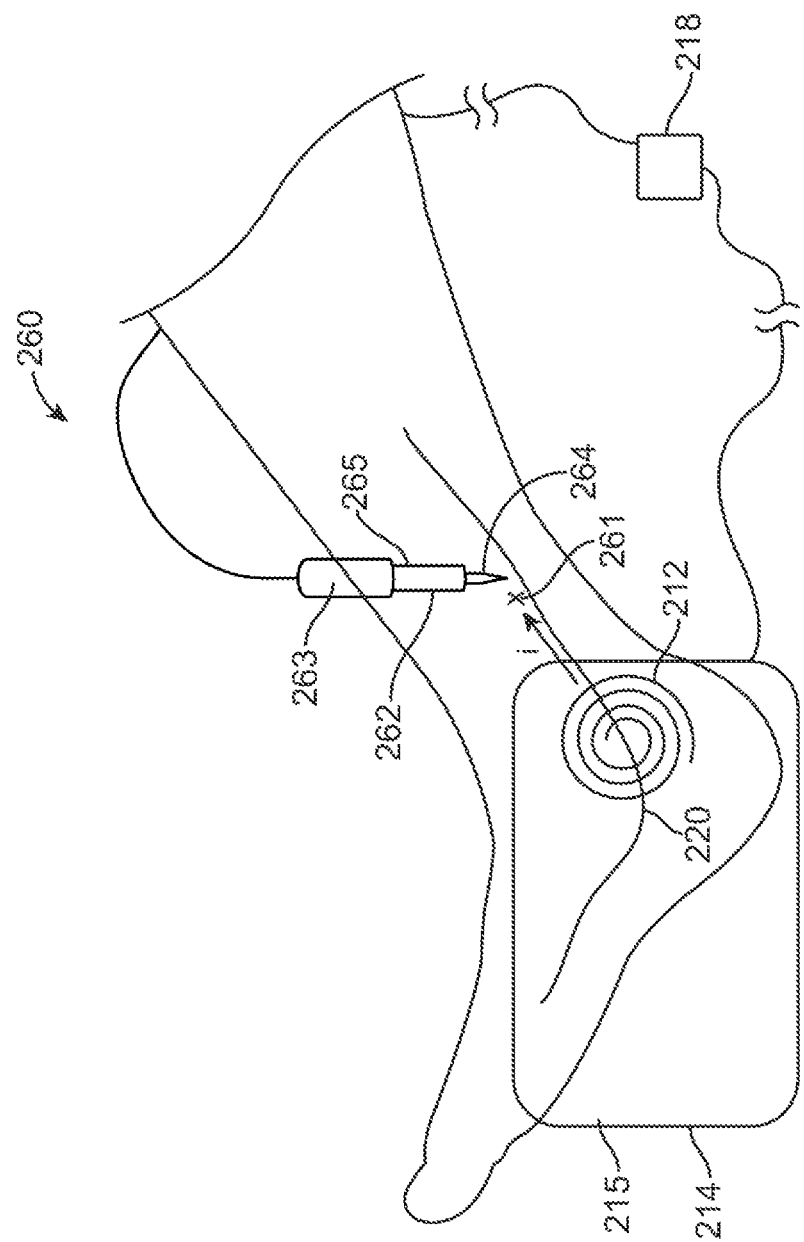
FIGS. 24-25 show schematic views of energy emitting systems including an electrode needle without a sensor.
Figure 25:
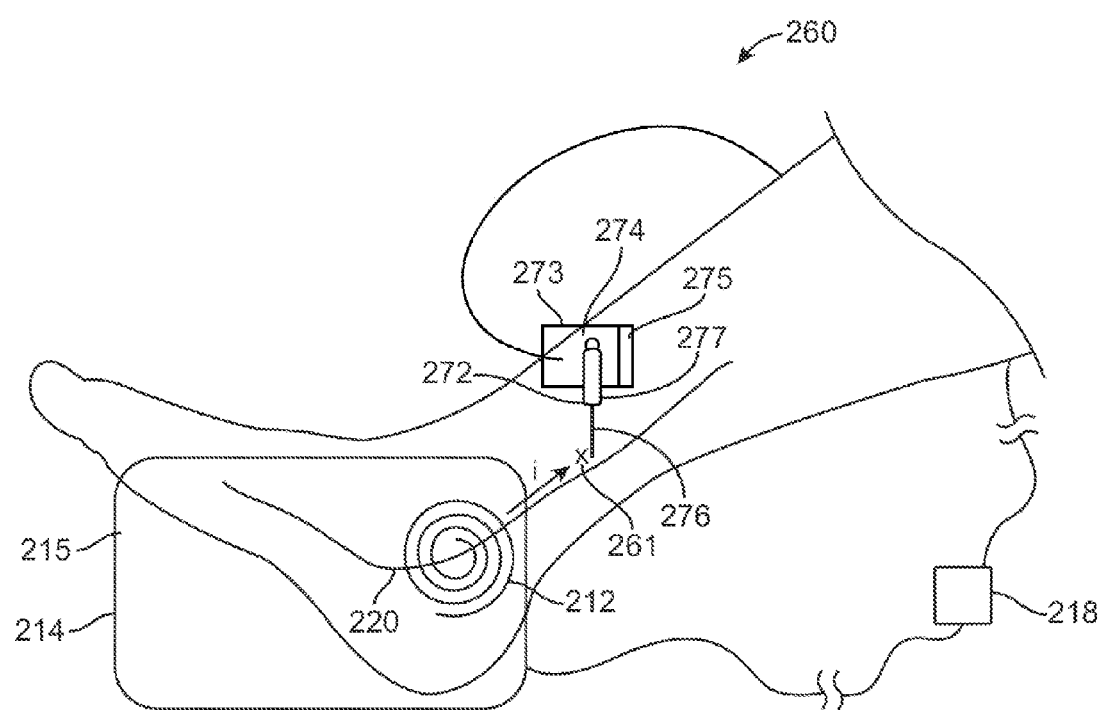

In certain embodiments of energy emitting system 260 as described above and shown in FIGS. 22-23, a sensor 216, such as a conductive microneedle patch 228, may be utilized to detect electrical conduction through the stimulated posterior tibial nerve 220 or to detect muscle stimulation and transmit the signal to controller 218. The signal may be transmitted to controller 218, a separate controller or device, or a separate controller coupled to controller 218. The controller can then be varied or adjusted based on the signal from microneedle patch 228 to ensure that adequate conduction of the posterior tibial nerve 220 occurs and an adequate and accurate dosage of treatment is being received. It is also contemplated that energy system 260 may be utilized without a sensor 216, see for example FIGS. 24-25. Optionally, other types of sensors may be used in place of a microneedle patch sensor, such as other sensors described herein and sensors known to persons of ordinary skill in the art. The sensor may be placed over a portion of the subject's body suitable for detecting conduction of the target nerve (e.g., on the leg as shown) or over a muscle to detect muscle stimulation resulting from stimulating the target nerve.

Figure 26:
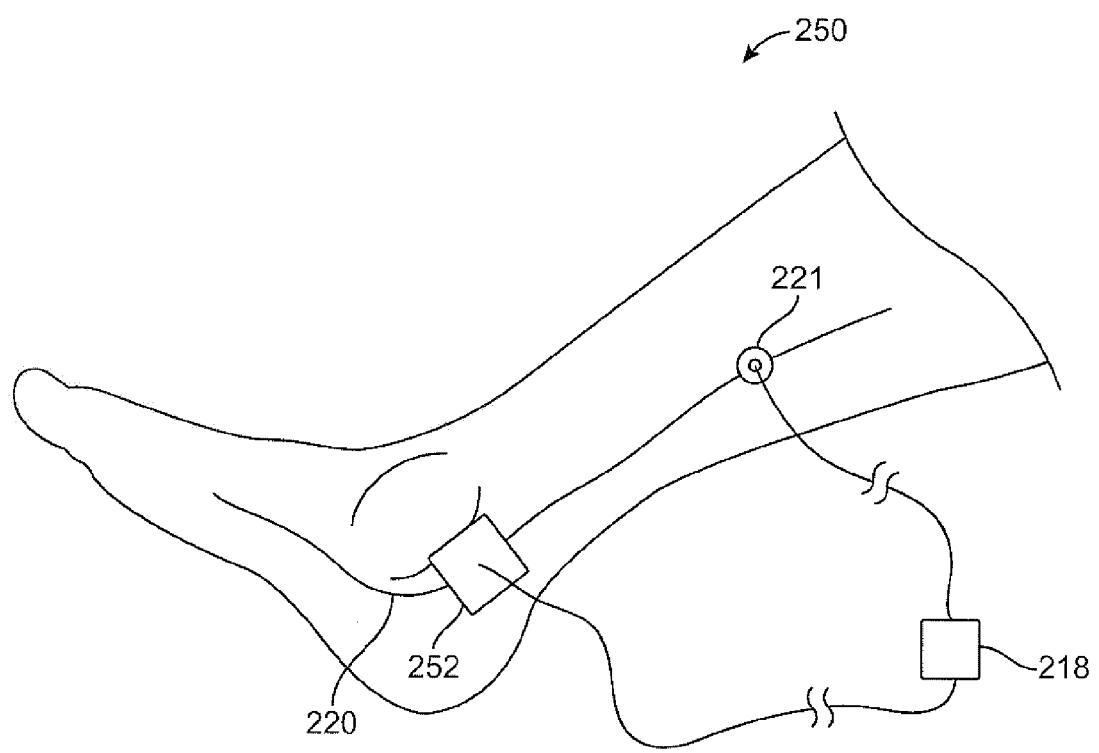
FIG. 26 shows a schematic view of an energy emitting system including a microneedle patch for providing stimulation.

In certain embodiments, as shown in FIG. 26, an energy emitting system 250 for providing a medical therapy includes a microneedle patch 252 (e.g., conductive microneedle patch) having one or more microneedle arrays deposited on a surface of one or more electrodes; one or more sensors 221 configured to detect electrical conduction in the target nerve or to detect muscle stimulation; and a controller 218 coupled to microneedle patch 252 and in communication with sensor 221. The microneedle patch 252 is configured such that an electrical current generated by the controller 218 is passed through the microneedle patch 252, generating a magnetic field or delivering or generating an electrical or magnetic stimulus to a target nerve, e.g., the tibial nerve 220, a muscle or other body part containing a portion of a target nerve, or any nerves branching off of a target nerve, located in proximity to microneedle patch 252.

Referring to FIG. 26, a method of using the energy emitting system 250 may include placing a conductive microneedle patch 252 on a first portion of a patient's body, for example a foot, ankle, or leg, in proximity to posterior tibial nerve 220 within the first portion of the patient's body. Sensor 221 is positioned along a second portion of the patient's body in proximity to the posterior tibial nerve 220. In this particular embodiment, sensor 216 is attached to the patient's leg in proximity to the posterior tibial nerve 220, proximal to and up-stream from conductive microneedle patch 252. Conductive microneedle patch 252 is composed of one or more microneedle arrays and one or more electrodes, as described in the embodiments above.

Once conductive microneedle patch 252 and sensor 221 are in position, a current is passed from controller 218 through conductive microneedle patch 252, resulting in an electrical stimulus of the posterior tibial nerve 220. Alternatively, the microneedle array may be insulated or constructed of non conductive material such that the microneedle patch 252 generates a magnetic field that stimulates tibial nerve 220 in a manner similar to the one or more coils described in the embodiments above, without an electrical stimulus. Whether the stimulus is electrical or magnetic, either stimulus will generate a current that will flow along the tibial nerve 220 and spread along its length, to its sacral or pudendal nerve roots. Sensor 221 detects electrical conduction through the stimulated posterior tibial nerve 220, and then transmits the signal to controller 218. In certain embodiments, the sensor may be in the form of a microneedle patch sensor. The signal may be transmitted to controller 218, a separate controller or device, or a separate controller coupled to controller 218. The controller can then be varied or adjusted based on the signal from sensor 221 to ensure that adequate conduction of the posterior tibial nerve 220 occurs and an adequate and accurate dosage of treatment is being received.

The sensor utilized in the energy emitting system 250 may be a sensor of the type described above, with respect to other embodiments. Optionally, for example, the sensor may be a microneedle patch. It is also contemplated that energy emitting system 250 can be utilized without a sensor.

In certain embodiments, energy emitting system 250 my optionally include one or more conductive coils disposed within or along a housing which can be positioned in proximity to the target nerve or muscle and provide an additional or supplemental stimulation of the target nerve or muscle.

Figure 27:
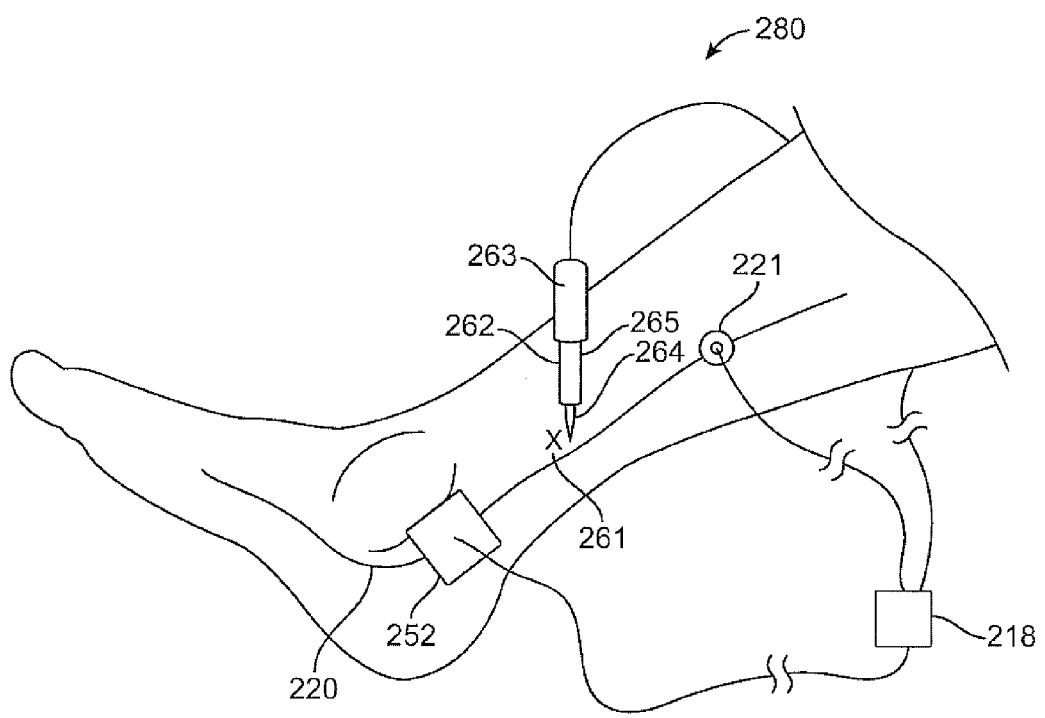
FIGS. 27-28 show schematic views of energy emitting systems including an electrode needle and microneedle patch for providing stimulation.

Referring to FIG. 27, the energy emitting system 250 described above with respect to FIG. 26 may be varied to create energy emitting system 280. Energy emitting system 280 further includes one or more percutaneous electrode needles 262 coupled to a controller 218 and having an end insertable into a subject's body in proximity to said target nerve. Optionally, the electrode needle may be non-percutaneous, such that it is insertable in an orifice or opening in the subject, such as a natural orifice. The percutaneous electrode needle 262 may be inductively coupled to conductive microneedle patch 252. In use, a microneedle patch 252 is placed on a first portion of a patient's body, for example a foot, ankle, or leg, in proximity to posterior tibial nerve 220 within the first portion of the patient's body and down-stream or distal to a selected stimulation site 261. The percutaneous electrode needle 262 is inserted through the skin at a location and to a depth that brings the tip in close proximity to the target nerve to be stimulated.

The controller 218 is activated and a current passes through microneedle patch 252 and traverses the internal stimulation site 261 by passing from microneedle patch 252 to the internal percutaneous electrode needle 262, as indicated by arrow i. The current passing through microneedle patch 252 may also generate a magnetic field which can generate a current that traverses the internal stimulation site 261 by passing from microneedle patch 252 to the internal percutaneous electrode needle 262. Also, the percutaneous electrode needle may be positioned within the generated magnetic field, whereby the magnetic field generates a current in the percutaneous electrode which stimulates a target nerve and traverses an internal stimulation site. Optionally, a current may be passed from the controller 218 through microneedle patch 252 and/or from the controller 218 through percutaneous electrode needle 262, traversing the internal stimulation site as the current passes between the patch and needle.

Figure 28:
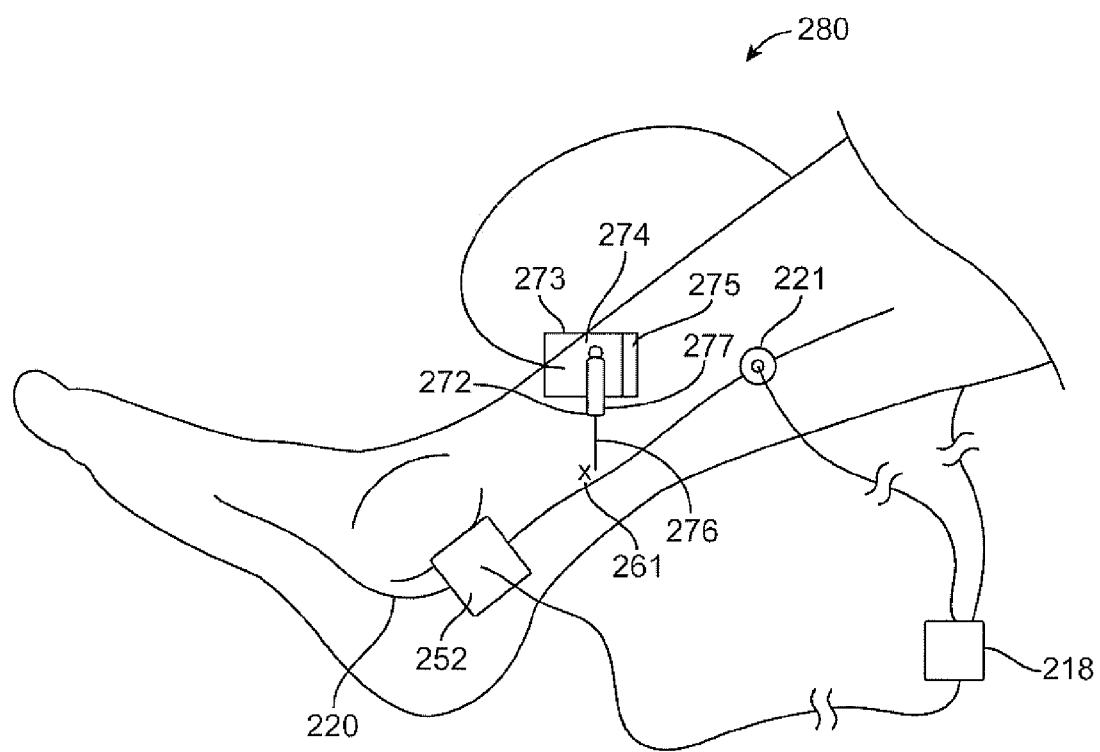
Figure 29A:
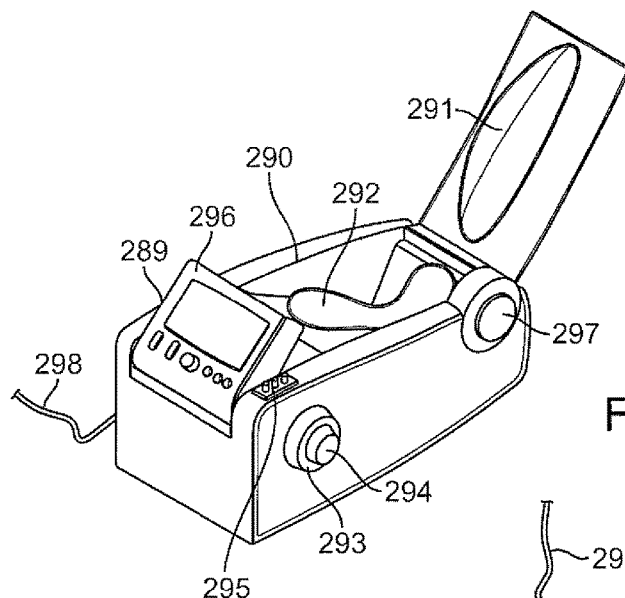
FIG. 29 shows prospective, side, top and rear views of an energy emitting device in the form of a foot cradle.
Figure 29B:
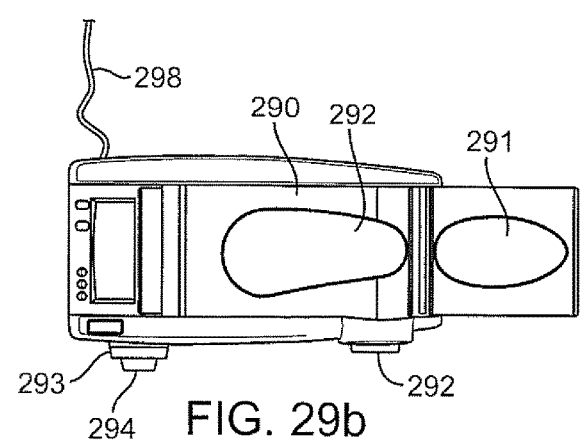
Figure 29C:
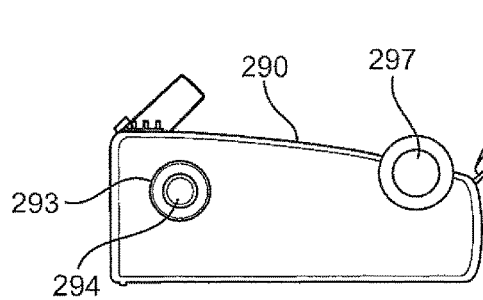
Figure 29D:
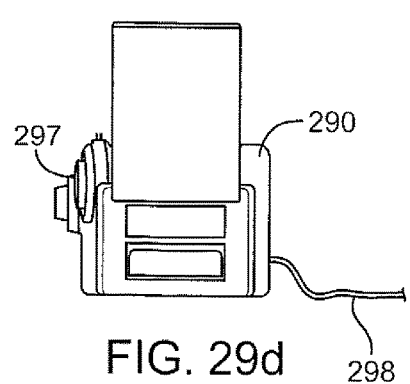

Referring to FIG. 28, energy emitting system 280 may be modified by using percutaneous electrode needle 272 in place of percutaneous electrode needle 262. Percutaneous electrode needle 272 would be constructed and function as described above with respect to FIG. 23. Various other implantable or insertable electrode needles known to persons of skill in the art may also be utilized in the above described systems. Additionally, energy emitting system 280 may utilize a sensor to detect electrical conduction through the stimulated posterior tibial nerve 220 and send a corresponding signal indicative of the detected conduction to controller 218 or other device such that the electrical or magnetic stimulus can be adjusted as necessary. The sensor may be a sensor 221, or optionally the sensor may be a microneedle patch. It is also contemplated that energy emitting system 280 can be utilized without a sensor. The sensor may be placed over a portion of the subject's body suitable for detecting conduction of the target nerve (e.g., on the leg as shown) or over a muscle to detect muscle stimulation resulting from stimulating the target nerve.

In any of the above systems, embodiments are contemplated where the sensors are also coupled or connected to or otherwise in communication with energy emitting devices, e.g., the conductive coils or conductive microneedle patches.

In certain embodiments, the one or more microneedles of the microneedle patch may include an electrically conductive material such that the microneedles may transmit an electrical signal to an overlying electrode or other surface. Microneedles may be constructed of an electrically conductive material and/or coated with an electrically conductive material. Optionally, microneedles may be coated with an electrically conductive material and constructed of a non-conductive material. Microneedles may be fabricated using a variety of materials, e.g., metals, stainless steel, solid or coat of gold over NI, Pd or Pd—Co, Pt, silicon, silicon dioxide, polymers, glass, biocompatible polymers, titanium, silver, or suture materials. Biodegradable polymers may also be used such that if a tip of a microneedle were to snap or break off during insertion, it would easily biodegrade. Optionally, the microneedle patch may be non-conductive.

In certain embodiments, an electrode patch for improved conductance or conduction is provided. The patch can include at least one electrode having a first surface and/or a second surface. The electrode may optionally be attached to various other materials or adhesive materials. An array of microneedles may be deposited on a surface of the electrode, or attached to a patch or other material and indirectly or directly connected to the electrode. The array of microneedles may include a conductive material. Such patches may be used as a sensor to detect muscle stimulation or electrical conductance, or to provide or deliver an electrical stimulus or magnetic field, e.g., to a target nerve, and may optionally be used in any of the embodiments described herein or in any application where improved conductance or conduction is desired. Microneedles yield improved reduction in impedance compared to simple abrasion and other techniques, and are less painful and more comfortable for the patient.

In certain embodiments, typical voltage sensed at the skin and detectable or conductable by a microneedle patch or microneedle array may range from about 1 to 400 microvolts or about 10 to 300 microvolts.

In certain embodiments, methods of treating a subject with urinary incontinence or various pelvic floor disorders utilizing the energy emitting systems described herein are contemplated. Symptoms associated with urinary incontinence may be observed, detected, or diagnosed. An energy emitting device having one or more energy generators, e.g., one or more conductive coils or one or more microneedle patches, may be positioned in proximity to a target nerve, e.g., the tibial or posterior tibial nerve or popliteal or sacral nerve or branches thereof of a subject or patient along a first portion of a subject's or patient's body. The subject may or may not be exhibiting symptoms associated with urinary incontinence. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with urinary incontinence, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn may cause the stimulation of a pudendal nerve, sacral plexus, or other nerves in the pelvic floor. Various nerves innervating the various muscles, sphincters, nerves, organs and conduits of the urinary tract and bladder may be stimulated directly or indirectly. In certain embodiments, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of urinary incontinence by achieving the appropriate level of conductance and appropriate level of nerve or muscle stimulation. Appropriate levels for current, frequency, magnetic field, treatment duration, etc., are levels that result in an observed or detected reduction or prevention of symptoms associated with urinary incontinence. Treatment could also be administered and the appropriate levels and parameters achieved through observing or detecting reduction or prevention of symptoms where a sensor is not used. Examples of these symptoms include but are not limited to the inability to control urinary function, urinary leakage, and loss of bladder control.

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat urinary incontinence, the magnetic field or electrical stimulus is applied to a subject or patient until the desired effects (e.g., reduction of symptoms) are achieved.

In certain embodiments, methods of treating a subject with fecal incontinence utilizing the energy emitting systems described herein are contemplated. Symptoms associated with fecal incontinence may be observed, detected, or diagnosed. An energy emitting device having one or more energy generators, e.g., one or more conductive coils or one or more microneedle patches, may he positioned in proximity to a target nerve, e.g., the tibial or posterior tibial nerve, or popliteal or sacral nerve or branches thereof of a subject along a first portion of a subject's body. The subject may or may not be exhibiting symptoms associated with fecal incontinence. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with fecal incontinence, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn causes the stimulation of a pudendal nerve, sacral plexus, or nerves in the pelvic floor. Various nerves innervating the various muscles, sphincters, rectum, nerves, organs and conduits associated with bowel movements, fecal control, and the intestines may be stimulated directly or indirectly. Optionally, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor is in the form a of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the posterior tibial nerve. The current may be adjusted or varied using a controller which is in communication with the energy generator. Adjustments may be made in response to the nerve or muscle stimulation detected by the conductive sensor, in order to optimize or ensure adequate treatment of fecal incontinence by achieving the appropriate level of conductance and appropriate level of nerve or muscle stimulation. Appropriate levels for current, frequency, magnetic field, treatment duration, etc., are levels that result in an observed or detected reduction or prevention of symptoms associated with fecal incontinence. Treatment could also be administered and the appropriate levels and parameters achieved through observing or detecting reduction or prevention of symptoms where a sensor is not used. Examples of these symptoms include but are not limited: the loss of voluntary control to retain stool in the rectum; loss of fecal control; inability to control bowel movements, and fecal leaking:

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat fecal incontinence, the magnetic field or electrical stimulus is applied to a subject or patient until the desired effects (e.g., reduction of symptoms) are achieved.

In certain embodiments, methods of treating a subject with restless leg syndrome utilizing the energy emitting systems described herein are contemplated. Victims afflicted with Restless Leg Syndrome (RLS or Ekbom's syndrome), are unable to remain seated or to stand still. Activities that require maintaining motor rest and limited cognitive stimulation, such as transportation, e.g., in a car, plane, train, etc., or attending longer meetings, lectures, movies or other performances, become difficult if not impossible. These sensations become more severe at night and RLS patients find sleep to be virtually impossible, adding to the diminishing quality of their lives. The urge to move, which increases over periods of rest, can be completely dissipated by movement, such as walking. However, once movement ceases, symptoms return with increased intensity. If an RLS patient is forced to lie still, symptoms will continue to build like a loaded spring and, eventually, the legs will involuntary move, relieving symptoms immediately.

Thus, symptoms associated with restless leg syndrome may be observed, detected, or diagnosed. An energy emitting device having one or more energy generators, e.g., one or more conductive coils or one or more microneedle patches, may be positioned in proximity to a target nerve, e.g., the tibial or posterior tibial nerve, or popliteal or sacral nerve or branches thereof or other nerves associated with restless leg syndrome, of a subject along a first portion of a subject's body. The subject may or may not be exhibiting symptoms associated with restless leg syndrome. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with restless leg syndrome, relative to an energy emitting device such that a target nerve within the first portion of the body is in proximity to at least one energy generator disposed within or along the energy emitting device.

A current is then passed through the energy generator to produce, generate or deliver energy, e.g., a magnetic field or electrical or magnetic energy or stimulus, focused on the tibial or posterior tibial nerve or branches thereof or other nerves associated with restless leg syndrome. This in turn causes the stimulation of a pudendal nerve, sacral plexus or other nerves innervating the various muscles, nerves, or organs associated with restless leg syndrome. The various nerves may stimulated directly or indirectly. Optionally, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form a of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of restless leg syndrome by achieving the appropriate level of conductance and appropriate level of nerve or muscle stimulation. Appropriate levels for current, frequency, magnetic field, treatment duration, etc., are levels that result in an observed or detected reduction or prevention of symptoms associated with restless leg syndrome. Treatment could also be administered and the appropriate levels and parameters achieved through observing or detecting reduction or prevention of symptoms where a sensor is not used. Examples of these symptoms include but are not limited to: uncomfortable sensations in the limbs, irresistible urges to move, usually the legs; motor restlessness; when at rest, symptoms return or worsen; and symptoms worsen in the evening and at night.

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat restless leg syndrome, the magnetic field or electrical stimulus is applied to a subject or patient until the desired effects (e.g., reduction of symptoms) are achieved.

In certain embodiments, methods of treating a subject suffering from premature ejaculation or various pelvic floor disorders utilizing the energy emitting systems described herein are contemplated. Symptoms associated with premature ejaculation may be observed, detected, or diagnosed. An energy emitting device having one or more energy generators, e.g., one or more conductive coils or one or more microneedle patches, may be positioned in proximity to a target nerve, e.g., the tibial or posterior tibial nerve or popliteal or sacral nerve or branches thereof of a subject along a first portion of a subject's body. The subject may or may not be exhibiting symptoms associated with premature ejaculation. In the case of the conductive coils, the coils may be positioned within or along a housing, such as a foot or knee cradle, and a foot or leg may be positioned therein. In the case of a microneedle patch, the patch maybe attached to a subject's skin. Optionally, the method involves positioning a first portion of a subject's body, the subject exhibiting symptoms associated with premature ejaculation, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn may cause the stimulation of a pudendal nerve, sacral plexus, or other nerves in the pelvic floor or nerves associated with the control of ejaculation. Various nerves innervating the various muscles, sphincters, nerves, organs and conduits of the urinary tract, bladder or reproductive system, or pelvic floor may be stimulated directly or indirectly. Optionally, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of premature ejaculation by achieving the appropriate level of conductance and appropriate level of nerve or muscle stimulation. Appropriate levels for current, frequency, magnetic field, treatment duration, etc., are levels that result in an observed or detected reduction or prevention of symptoms associated with premature ejaculation. Treatment could also be administered and the appropriate levels and parameters achieved through observing or detecting reduction or prevention of symptoms where a sensor is not used. Examples of these symptoms include but are not limited to: ejaculation that frequently occurs within one minute or less of penetration; the inability to delay ejaculation on penetrations; or persistent or recurrent ejaculation with minimal stimulation before, on or shortly after penetration.

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat premature ejaculation, the magnetic field or electrical stimulus is applied to a subject or patient until the desired effects (e.g., reduction of symptoms) are achieved.

Exemplary treatment parameters for treating various conditions, e.g., urinary incontinence, using the systems and methods described herein may include the following. Operation of a conductive coil at about 10 to 20 hertz generating a magnetic field of about 0.25 to 1.5 tesla, where the coil is administered to a patient for a duration of about 30 minutes/day or 30 minutes per week, depending on the severity of the symptoms, until the symptoms subside. The above treatment parameters or variations on the parameters may be used for treatment of urinary incontinence, fecal incontinence, restless leg syndrome, or premature ejaculation or other conditions. For example, the coil may be operated at various parameter ranges falling with the following ranges: about 5 to 100 hertz, about 1 to 10 tesla, for about 15 minutes to 2 hours per day or week. In treating premature ejaculation, a patient may receive treatment about 4 to 10 hours prior to intercourse. A maintenance phase of treatment, after the initial treatment, may vary for various conditions. For example, the maintenance phase may require application of the systems and methods described herein at the parameters described herein for 30 minutes/week or 30 minutes/month. Any treatment parameter may be varied or modified based on the effect on the patient or sensor or patient feedback regarding stimulation, until the desired result of treating or preventing a condition is achieved.

In certain embodiments, as shown in FIG. 29a-29d, an energy emitting device can include a controller 289 and a foot cradle 290. Foot cradle 290 may include vertical foot plate 291, and horizontal foot plate 292, where each plate can be adjusted using vertical foot plate knob 293 and horizontal foot plate knob 294. One or more EMG plugs 295 are provided. An air core coil 297 or other type of coil is provided. A display screen 296 may also be provided along with power cord 298. The display screen 296 can display a variety of information to the user and/or practitioner such as the level of power or current applied, treatment time, temperature of the cradle device, detected current levels and/or physiological parameters, etc., to facilitate effective and efficient therapeutic treatment. The information can be used to vary or adjust the controller to ensure that adequate conduction of a target nerve, e.g., posterior tibial nerve 220 or muscle stimulation, occurs and an adequate and accurate dosage of treatment is being received. Controls may also be included to affect the following: power, field strength, frequency, pulse, start/pause and cancelation of therapy (as shown), or other parameters one of skill in the art would find necessary or useful to control or monitor. In certain embodiments, a sensor may be connected, or in communication with the foot cradle or other energy emitting apparatus, controller, housing, conductive coils, or microneedle patch.

Figure 30:
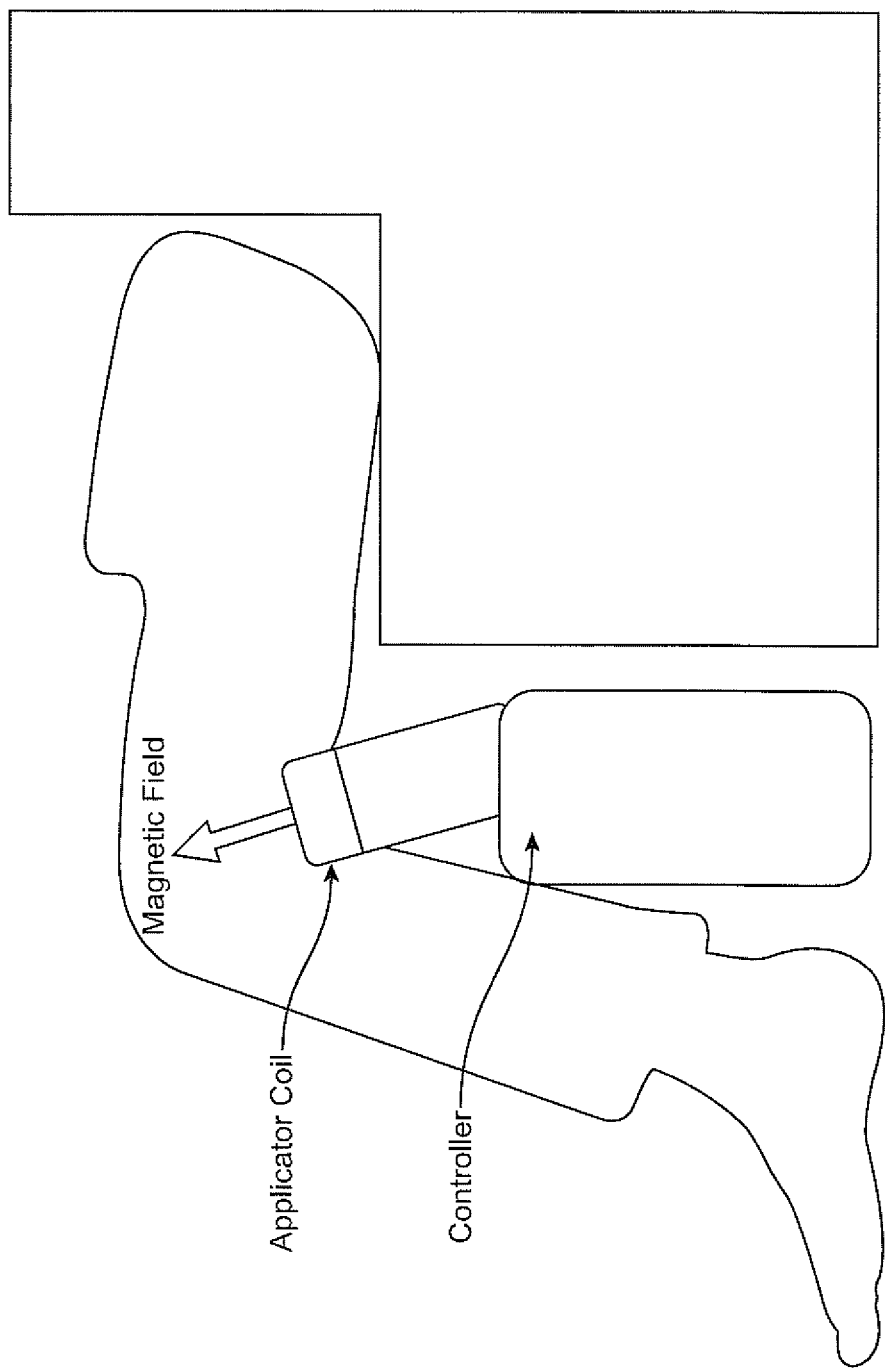
FIGS. 30-31 show schematic views of an energy emitting device in the form of a knee cradle.
Figure 31:
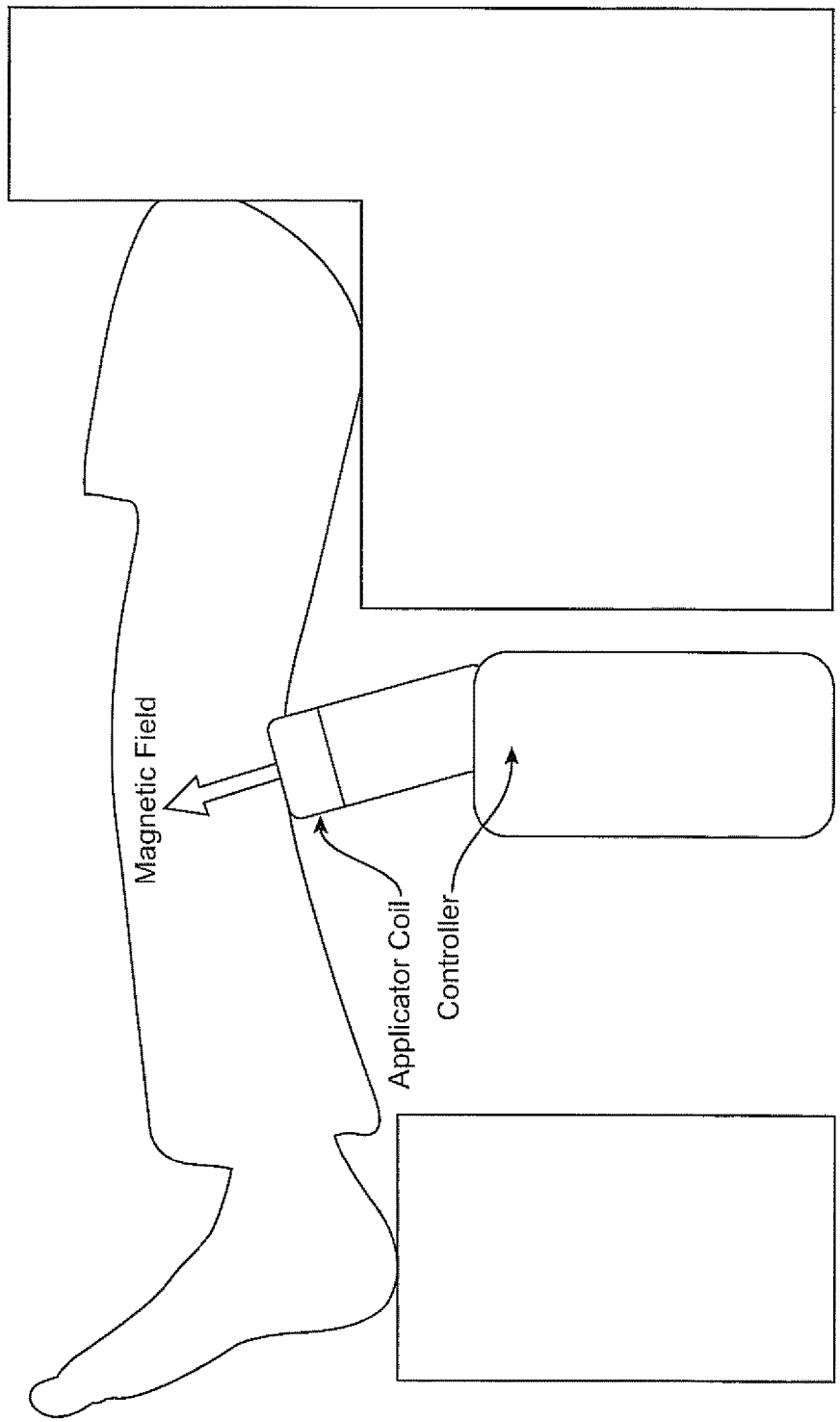

In certain embodiments, as shown in FIGS. 30-31, an energy emitting device may include a controller and a knee cradle. The cradle may be configured to provide the conductive coil in proximity to the popliteal fossa or area directly behind the knee. In certain embodiments, the knee cradle may configured to cradle or surround at least a portion of the knee or substantially the entire knee without placing direct pressure on the popliteal fossa, thereby minimizing or avoiding venous thrombosis. In one embodiment, the device may be utilized while the knee is in the flexed position (FIG. 30). In another embodiment, the device may be utilized while the knee is in a non-flexed position (FIG. 31).

In certain embodiments, the energy emitting device, e.g., foot cradle, knee cradle, etc., includes a conductive coil positioned such that a target nerve is automatically targeted. The conductive coil is configured, sized and positioned within the device such that the generated electromagnetic or magnetic field may encompass and stimulate the target nerve in any patient based on the target nerve's anatomical location, thus providing automatic targeting of the nerve in any patient once the patient positions a particular body portion in the device.

In various embodiments described herein, sensors may detect voltage or current and may be connected, coupled, wirelessly connected or coupled or otherwise in communication with housing, conductive coils, microneedle patch, energy emitting apparatus or device, energy generators, or electrode needles and/or controller using a variety of methods or techniques known in the art. In various embodiments described herein, housings, conductive coils, microneedle patches, energy emitting apparatus, energy generators, or electrode needles may be connected, coupled, wirelessly connected or coupled or otherwise in communication with each other, controllers or sensors, using a variety of methods or techniques known in the art.

An energy emitting system for providing a medical therapy according to any of the embodiments described herein may include an energy emitting device and/or one or more energy generators for generating an electromagnetic field or magnetic field and/or delivering an electromagnetic stimulus. In certain embodiments, the energy generator may be a conductive coil, which is configured to generate a magnetic field to be focused on a target nerve. The one or more conductive coils are optionally positioned within or along a housing, as described herein. Various embodiments of conductive coils are contemplated. A conductive coil utilized in any of the embodiments described herein may optionally include a variety of configurations or features, e.g., cooling features for conduction or convection cooling, which optimize the conductive coil's effectiveness in generating a magnetic field and stimulating a target nerve, while providing a safe and effective medical therapy for a patient.

Figures 32, 33:
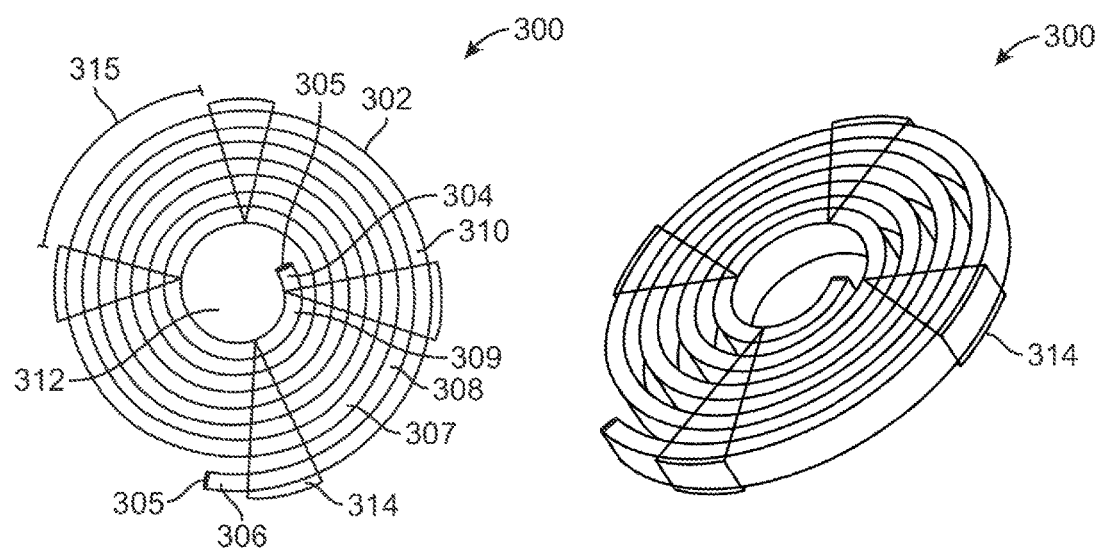
FIG. 32 shows a front view of a variation of a conductive coil.
FIG. 33 shows a prospective view of a variation of a conductive coil.

Referring to FIG. 32, in certain embodiments, a conductive coil 300 may be configured in the form of a spiral. The conductive coil 300 may have a coil body 302. The coil body 302 includes a first end portion 304 and a second end portion 306. The first end portion 304 and the second end portion 306 may include electrical contact points 305. In between the first and second end portions 304, 306 the coil body includes one or more turns 307 forming a spiral configuration. Each turn 307 may be spaced apart from an immediately adjacent turn such that a space or gap 308 is provided between adjacent turns. The space or gap between a turn and an immediately adjacent turn may vary. For example, the space or gap may be from about 0.05 mm to about 0.5 mm or from about 0.15 mm to about 0.25 mm or the gap may be about 0.15 mm. The radius of curvature for each turn may increase from the inner turn 309, positioned at the center of the coil body 302, to the outer turn 310, which forms the outer perimeter of the coil body 302. Thus, the radius for each successive turn may increase from the center of the spiral coil to the outer perimeter of the spiral coil. Optionally, a central aperture 312 is provided at the center of the coil body. The central aperture 312 is surrounded by inner turn 309.

The diameter of the central aperture may vary. For example, the diameter may range from about 0.5 inch to 2 inches or 1 inch to 1.5 inches or the aperture may have a diameter of about 1 inch. The diameter of the coil body may vary. For example, the diameter may range from about 3.0 to about 7 inches or from about 4 to about 5 inches or the diameter may about 4.5 inches. The coil body may include any suitable number of turns. For example, the coil body may include from about 2 to about 25 turns or from about 10 to about 20 turns or 14 to 17 turns. A turn may have various dimensions. For example, the turn or end or cross section of the turn may have a height that is greater than its width or thickness, e.g., 15 to 60 times or 25 to 50 times greater in height relative to its width. In certain embodiments, a turn or an end or cross section of a turn may have a height ranging from about 1 to 5 cm or from about 10 mm to 51 mm (about 0.3 inches to 2 inches) or about 25 mm to 40 mm (about 1 inch to 1.5 inches) or about 12 mm to 40 mm (about 0.5 inch to 1.5 inch) or about 0.5 inch to 2 inch. The turn or end or cross section of the turn may have a width ranging from about 0.5 mm to about 5 mm (about 0.019 inch to 0.19 inch) or from about 1 mm to about 2 mm (about 0.03 inch to 0.07 inch) or about 0.2 mm to about 1.6 mm (about 0.01 inch to 0.06 inch). Optionally, the dimensions may allow the coil turns to be tightly packed or rolled while still maintaining gaps or spaces in between adjacent turns, allowing for conduction and/or cooling. Optionally, the dimensions may allow the coil to be more loosely packed or rolled, allowing for conduction and/or cooling. The above are exemplary dimensions, where other dimensions are also contemplated depending on the use and configuration of a device.

Any of the embodiments of coils described herein and illustrated in the corresponding figures may have the above dimensions and configurations or any other suitable dimension or configuration depending on the coils intended use.

In certain embodiments, referring to FIGS. 32 and 33, a material 314, e.g., a non-electrically conductive, thermally conductive, non-thermally conductive and/or insulator material positioned on the surface of the coil body 302 or conductive coil 300. The material may be an epoxy or other material having similar properties. Such materials can include but are not limited to, e.g., plastic, non-electrically conductive polymers, silicone, etc. The material, for example, a non-electrically conductive material 314, may be configured in a variety of shapes, sizes, designs, etc., depending on the particular coil and may be applied over or along portions of the surfaces of the conductive coil 300 or coil body 302 to hold or maintain the coiled configuration as well as to maintain separation between adjacent turns of the coil body 302, maintaining air flow or fluid flow gaps 308 between the adjacent turns. For example, in the embodiments shown in FIGS. 32 and 33, the non-electrically conductive material 314 can be configured in the form of a wedge. The wedge may be positioned on the surface of coil body 302. A wedge may be adhered to or otherwise attached or affixed to one or more surfaces or faces of a coil body 302. The wedge may extend from the central aperture or the inner turn 309 of the coil body 302 over a front face or surface of the coil body, around and over the outer surface of the outer turn or outer perimeter of the conductive coil, and over a back surface or back face of the coil body 302, thereby partially encasing or surrounding the coil body. Optionally, the wedges or other configuration of non-electrically conductive material may be attached on a single surface or face of the coil body, or as separate pieces or a single piece on the front and back faces and outer perimeter or surface of the coil body, or on one or both of the front and back faces of the coil body and the outer surface of the outer turn or perimeter of the coil body. The total diameter of the coil body with the non-electrically conductive material on its surface, may vary. For example, the total diameter may range from about 3 to about 7 inches or from about 4 to about 5 inches or the total diameter may be about 5 inches. Although shown in a tapered wedge configuration, other shapes or configurations are utilizable; for instance, a uniform strip of material may be applied along one or more radii of the coil body 302. Any number of alternative variations may be applied so long as the material maintains separation between the turns of the coil body 302.

In certain embodiments, as shown in FIGS. 32 and 33, one or more wedges of non-electrically conductive material 314 are positioned on or around the coil body 302. The wedges maintain separation between adjacent turns of the coil body 302, maintaining gaps 308 between adjacent turns for air flow or fluid flow passage, and further providing one or more air flow or fluid flow channels 315 in between each wedge. The gaps 308 between adjacent turns provide a path or passage for air or other fluid to pass through the coil body in between and over the coil turns, which assists in cooling the coil. Also, the air or fluid flow channels 315 provide a path for directing air or other fluid to pass over or around the coil body, which assists in cooling the coil.

Figure 34:
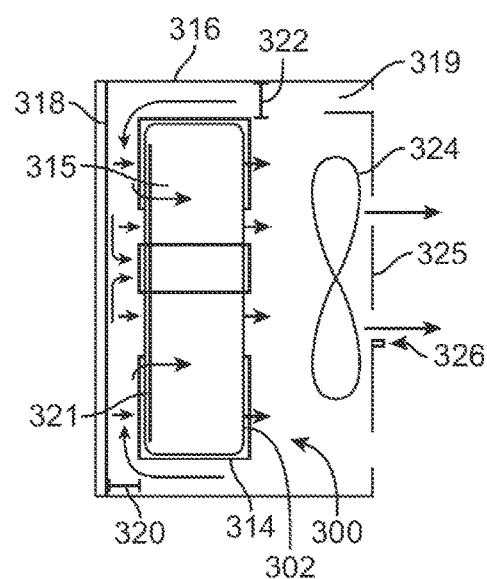
FIG. 34 shows a side view of an energy emitting system including the conductive coil of FIG. 32.

FIG. 34 shows a side view of an embodiment of the conductive coil 300, positioned within a housing 316 (a cross section of the housing is shown surrounding the conductive coil). The housing 316 includes a patient interface plate 318. The housing and/or patient interface plate can be made from a variety of materials having various properties, such as non-electrically conductive or non-thermally conductive or insulating materials. Such materials may include but are not limited to, e.g., ceramic, ceramic alloy, plastic, epoxy, other materials made by Cool Polymers® or materials having similar properties. The patient interface plate 318 may be substantially rigid, if desired. A rigid plate helps prevent bending or flexing of the plate due to pressure applied against the plate by a patient during use, thus avoiding contact between the patient interface plate 318 and the non-electrically conductive material 314, e.g., an epoxy.

In certain embodiments, a shield of insulating material or an insulating shield or layer, e.g., an overlay of thin flexible plastic or other non-electrically conductive or non-thermally conductive material, may optionally be provided over or under the patient interface plate. This material would serve as a backup insulator providing an additional barrier between the patient and the conductive coil. One or more insulating shields or layers may be provided. The shield or layer provides additional insulation and backup insulation should the patient interface plate crack or break. The shield or layer may optionally be made from any of the materials described herein for making the patient interface plate or housing.

The conductive coil 300 may be positioned within the housing such that a space or gap is provided between the conductive coil 300 and the patient interface plate 318, e.g., gap 320. The distance between the patient interface plate 318 and the non-electrically conductive material 314 may vary. For example, the distance may range from about 0.2 mm to 0.5 mm or about 0.2 mm to 0.7 mm or about 0.3 mm to 0.5 mm or the distance may be about 0.5 mm. The distance between the patient interface plate 318 and the front face 321 of the conductive coil may vary. For example, the distance may range from about 0.5 mm to 3 mm or about 1 mm to 2 mm or the distance may be about 1.5 mm. A space or gap 322 may also be provided between the housing and the outer turn or outer perimeter of the conductive coil. The distance making up gap 322 may vary. For example, the distance of the gap may range from about 1.58 mm to 6.35 mm (about 1/16 inch to about 1/4 inch) or the distance may be about 3.17 mm (about 1/8 inch).

Still referring to FIG. 34, a cooling device, e.g., a blower 324, may be provided within or near the housing 316. In certain embodiments, the conductive coil 300 is positioned between the patient interface plate 318 and the blower 324. The blower 324 may be a fan or other device for pulling, pushing, forcing or circulating air. The air may be ambient, cooled, refrigerated, etc. The blower 324 may be, e.g., configured to pull air over, around, and/or through the conductive coil 300, thereby cooling and/or insulating the conductive coil 300.

In operation in certain embodiments, as indicated by the arrows in FIG. 34, blower 324 actively pulls or pushes air into the housing 316 through one or more inlets 319. The air is pulled or pushed through gaps 320 and 322, around and/or over the conductive coil 300 and in between wedges 314 and through air flow channels 315. The air may be pulled or pushed through gaps 308, in between turns 307, which make up coil body 302, and/or through the central aperture 312 (shown in FIG. 32). Therefore, air is continuously or periodically refreshed as it is circulated and flows over, around, and/or through the conductive coil 300 and coil body 302, in between the patient interface plate 318 and the remainder of the housing and the conductive coil 300, and is withdrawn from the housing 316, thereby cooling or insulating the conductive coil and keeping the patient interface plate 318 at an acceptable temperature for patient use. For example, the patient interface plate 318 may be kept a temperature less than about 50 degrees Celsius or less than about 45 degrees Celsius or less than about 42 degrees Celsius or from about 37 to 42 degrees Celsius. In the event that the blower 324 is used to push airflow through gaps 320, one or more blowers may be positioned to force airflow through the gaps 320 such that the heated air is pushed (rather than pulled) over and through the coil 300 and vented from the housing 316. In certain embodiments, various fluids, including air or other fluids, may be actively or passively pulled or pushed over, around and/or through the spaces and/or gaps of the coil to provide cooling.

Optionally, the warmed air or other fluid is withdrawn from the housing by being vented out of the rear face of the housing or a venting plate 325, opposite the patient interface plate. The rear face of the housing may have one or more vents, outlets or openings for venting the heated air. In certain embodiments, one or more vents, outlets or openings for venting warmed air may be located at various positions on the housing, e.g., the side, top, bottom, etc.

In certain embodiments, the fluid flow or airflow may vary. For example, the flow rate may be greater than about 100 CFM (cubic feet per minute) or it may range from about 20 CFM to about 100 CFM or from about 25 CFM to about 60 CFM. In other embodiments, the cooling device may provide an air or fluid flow at a flow rate ranging from about 0.5 liters per second to about 4 liters per second or from about 1 liter per second to about 2 liters per second. The pressure head parameters may vary. For example, the pressure head may range from about 0.5 inches of 1-120 to about 10 inches of H20 or from about 0.5 inches of H20 to about 4 inches of H20.

In certain embodiments, the conductive coil 300 may be configured without a material, e.g., a non-electrically conductive or thermally conductive material, on its surface. Air or other fluid may still be pulled or pushed over, through, and/or around the conductive coil to cool the coil.

In certain embodiments, a chilling or refrigerator device, external or internal cooling supply, water or other fluid reservoir or other device may optionally be used alone as the cooling device or in combination with another cooling device, e.g., a blower, to provide cool fluid over, through, and/or around the coil to cool the conductive coil.

The patient interface plate 318 may optionally include a reflective surface, to provide an additional cooling mechanism. A reflective surface positioned on or next to the patient interface plate 318 may be used in addition to or in place of the blower 324. A reflective surface may reflect light and radiant heat, thereby cooling the patient interface plate 318 and helping to maintain the patient interface plate 318 at an acceptable temperature for patient use.

Figure 35:
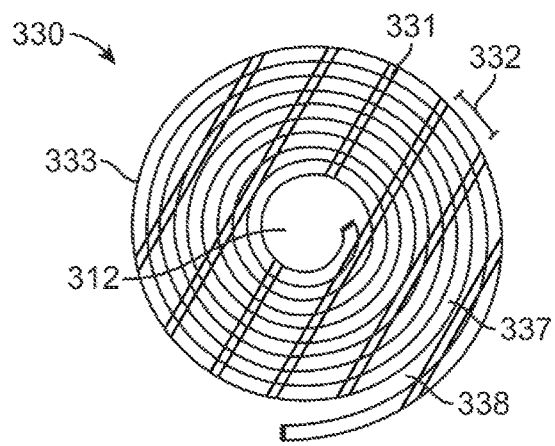
FIG. 35 shows a front view of a variation of a conductive coil.
Figure 36:
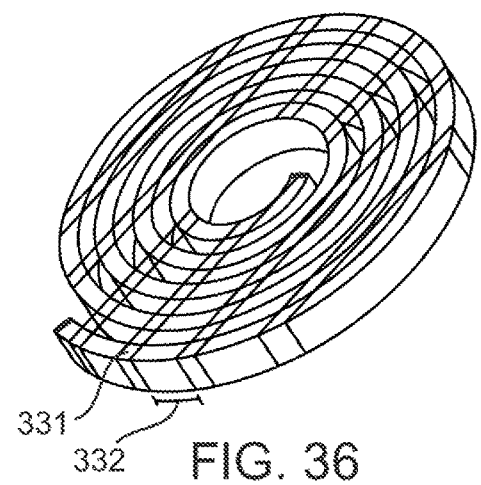
FIG. 36 shows a prospective view of a variation of a conductive coil.
Figure 37:
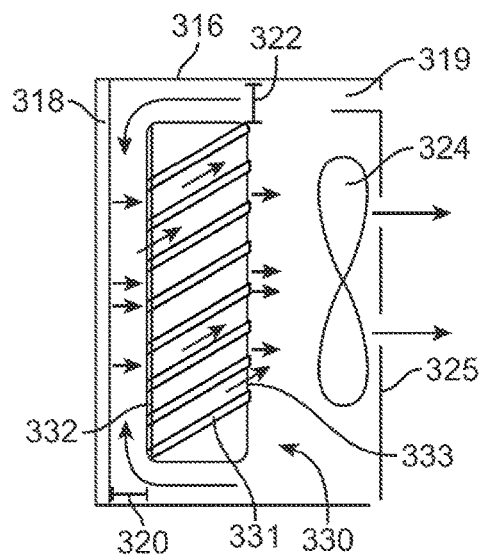
FIG. 37 shows a side view of an energy emitting system including the conductive coil of FIG. 35.

Referring to FIGS. 35-37, in certain embodiments, a material in the form of a tape, wrap or strip, may be positioned along portions of the surfaces of the conductive coil 330. For example, a non-electrically conductive tape 331 may be wrapped around the coil body 333 such that when the coil is wrapped about itself, at least one surface of apposed adjacent surfaces of turns 337 of the coil body 333 are maintained at a distance from one another by the tape 331 to provide air flow or fluid flow gaps 338. The tape 331 also creates a series of air flow or fluid flow channels 332 on the surface of the coil body 333 directing fluid over the coil. Optionally, the tape 331 is wrapped about the coil body 333 at a non-zero angle, e.g., at about a 45 degree angle to prevent or minimize denting or bending of the turns 337. In some embodiments, a zero angle wrap may be suitable. The tape 331 may be made from a variety of materials. For example, the tape may be made from silicone or other materials having similar properties. Such materials may include but are not limited to, e.g., plastic, non-electrically conductive polymers, epoxy, etc.

In operation, as indicated by the arrows in FIG. 37, blower 324 can pull or push air into the housing 316 through one or more inlets 319. The air is pulled or pushed through gaps 320 and 322 and around or over the conductive coil 330 and in between the strips of non-electrically conductive tape 331 and through air or fluid flow channels 332. The air may also be pulled or pushed through air or fluid flow gaps 338, in between turns 337 which make up coil body 333, and/or through the central aperture 312 (shown in FIG. 35). Therefore, air is continuously or periodically refreshed as it is circulated and flows over, around, and/or through the conductive coil 330 or coil body 333, in between the patient interface plate 318 and the remainder of the housing and the conductive coil 330, and is withdrawn from the housing 316. This allows for cooling or insulating of the conductive coil and keeping the patient interface plate 318 at an acceptable temperature for patient use. For example, the patient interface plate 318 may be kept a temperature less than about 50 degrees Celsius or less than about 45 degrees Celsius or less than about 42 degrees Celsius or from about 37 to 42 degrees Celsius.

Referring again to FIGS. 34 and 37, in certain embodiments, an energy emitting device includes a conductive coil positioned within a housing, the conductive coil has a coil body which has one or more turns and a central aperture. A material may be positioned on a surface of the coil body to provide a fluid flow channel for cooling the conductive coil and to maintain separation between adjacent coil turns. Also, a cooling device may be provided. The cooling device may be a blower 324 or other device configured to cool the conductive coil by drawing air into the housing, over the coil body, through the gap in between the turns, and/or through the central aperture.

Optionally, the housing can include a patient interface plate 318, which can come into contact with the patient and separates the patient from the conductive coil 300 or 330. The housing may also include a venting plate 325. The venting plate 325 may be positioned substantially opposite the patient interface plate 318, facing generally away from the patient and enclosing the cooling device, e.g., blower 324 or other device for cooling the conductive coil.

In certain embodiments, (e.g., as shown in FIG. 34) a sensor, e.g., sensor 326, may optionally be provided, positioned near to or in close proximity to the venting plate 325 or in the path of the vented air. The sensor may be attached to the housing, conductive coil, or cooling device, or may be separate from the energy emitting device, but located in close proximity to the energy emitting device. The sensor may be a temperature sensor used to monitor the temperature of warmed air vented from the venting plate 325 to ensure that the temperature does not reach dangerous levels that could be harmful to the patient, physician or other user, even when the conductive coil is operating continuously at heavy loads. Optionally, the desired temperature may be maintained by providing automatic or manual feedback loop, where the load at which the conductive coil is being run may be adjusted according to the temperature data provided by the sensor.

Optionally, a temperature sensor may be provided to monitor the temperature of the patient interface plate 318. The sensor may be attached to the housing, conductive coil, or patient interface plate, or may be separate from the energy emitting device, but located in close proximity to the patient interface plate 318. The sensor may be a temperature sensor used to monitor the temperature of the patient interface plate to ensure that the temperature does not reach dangerous levels that could be harmful to the patient as the conductive coil is operating continuously at heavy loads. In certain embodiments, a temperature sensor for monitoring temperature of the patient interface plate ensures that the plate remains at a temperature of no greater than about 42 degrees C. Optionally, the desired temperature may be maintained by providing an automatic or manual feedback loop, where the load at which the conductive coil is being run may be adjusted according to the temperature data provided by the sensor.

In certain embodiments, the conductive coil may be configured to run continuously or periodically at various loads, including very high loads, while a patient interface plate positioned on the housing remains at an acceptable and patient safe temperature, e.g., a temperature of no greater than about 42 degrees C. For example, the number of pulses provided by the energy emitting system and the time intervals for doing so can vary. For example, the energy emitting system may be configured such that the conductive coil provides from about 34,000 to about 47,000 pulses or 36,000 to about 45,000 pulses over about 20 to 40 minutes or up to about 44,400 pulses over about 30 minutes, while the patient interface plate positioned on the housing is maintained at a temperature of no greater than about 42 degrees C. The various features of the energy emitting system described herein, including the conductive coil, housing and cooling device, allow the conductive coil to operate at high power rates and heavy loads. For example, the coils may operate at the following parameters: about 10 to 30 hertz or about 15 to 25 hertz or about 20 hertz and at about 700 to 1100 volts or about 800 to 1000 volts or about 900 volts, for over about 25 to 40 minutes or 27 to 35 minutes or about 30 minutes. In certain embodiments, the features of the energy emitting system allow the conductive coil to be operated continuously, substantially continuously, periodically, or at a high rep rate, with no shutdown of the conductive coil necessary to prevent overheating or to prevent a risk to the patient.

In certain embodiments, a method of magnetic induction therapy is provided. The method includes positioning a first portion of a patient's body relative to an energy emitting device such that a target nerve within the first portion of the patient's body is in proximity to the conductive coil disposed within or along the energy emitting device. A current is then passed through the conductive coil to generate a magnetic field focused on the target nerve. The first portion of the patient's body, e.g., the patient's leg or ankle, is positioned relative to the energy emitting device and conductive coil, or optionally, the conductive coil is situated relative to the first portion of the patient's body, such that the electromagnetic or magnetic flux generated by the conductive coil is concentrated on, near or over the target nerve or in close proximity to the target nerve.

The conductive coil can be cooled during, after or before operation. Cooling may be performed by drawing air or other fluid at a flow rate over the conductive coil body, between the various turns making up the conductive coil, and optionally through a central aperture of the conductive coil. The fluid flow or airflow may vary. For example, the flow rate may be greater than about 100 CFM or it may range from about 20 CFM to about 100 CFM or from about 25 CFM to about 60 CFM. In other embodiments, the cooling device may provide air or fluid flow at a flow rate ranging from about 0.5 liters per second to about 4 liters per second or from about 1 liter per second to about 2 liters per second. The pressure head parameters may vary. For example, the pressure head may range from about 0.5 inches of H20 to about 10 inches of H20 or from about 0.5 inches of H20 to about 4 inches of H20.

As the conductive coil is cooled, warm air or other warm fluid that has passed, over, around and/or through the conductive coil to cool the coil may be vented out of the energy emitting device away from the first portion of a patient's body. The energy emitting device or housing may have a venting plate or other outlet whereby the warmed air is vented such that it exits the device in a direction substantially opposite the first portion of the patient's body to prevent or minimize the patient's contact with warmed or heated air.

Optionally, the temperature of the warmed air exiting the device is monitored such that the temperature can be regulated to maintain temperatures at a relatively safe level. In certain embodiments, the temperature of the patient interface plate or a portion of the energy emitting device that can come into contact with the patient may also be monitored or detected. This monitoring allows the temperature to be regulated to maintain temperatures at a relatively safe level, e.g., no greater than about 42 degrees C.

In certain embodiments, the conductive coil may be configured to run continuously or periodically at various loads including very high loads, while a patient interface plate positioned on the housing remains at an acceptable and patient safe temperature, e.g., a temperature of no greater than about 42 degrees C. For example, the number of pulses provided by the energy emitting system and the time intervals for doing so can vary. For example, the energy emitting system may be configured such that the conductive coil provides from about 34,000 to about 47,000 pulses or 36,000 to about 45,000 pulses over about 20 to 40 minutes or up to about 44,400 pulses over about 30 minutes, while the patient interface plate positioned on the housing is maintained at a temperature of no greater than about 42 degrees C.

The methods described above can be use to treat or prevent various conditions and/or reduce or minimize their associated symptoms. Examples of such conditions include urinary incontinence, fecal incontinence and or restless leg syndrome.

Figure 38:
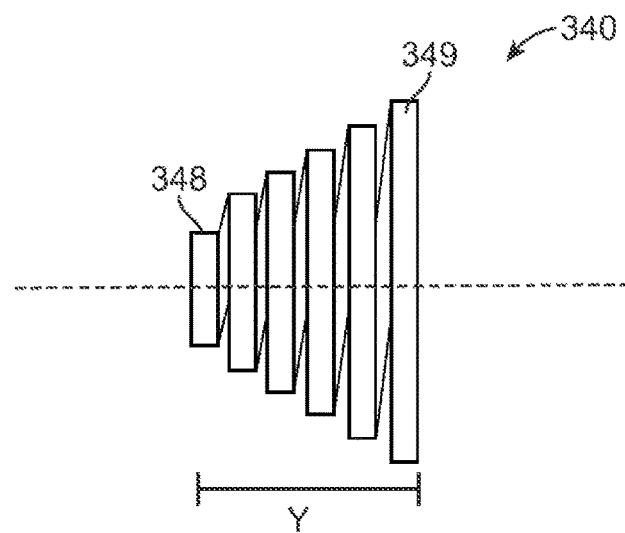
FIG. 38 shows a side view of a variation of a conductive coil.

The conductive coil as described in any of the embodiments herein may take on a variety of shapes or configurations. For example, the conductive coil may be substantially planar. The spiral conductive coil 300 shown in FIGS. 32-34 is substantially planar. Optionally, referring to FIGS. 38-39, the conductive coil 340 may be substantially conical in configuration or shape. In a conical configuration, as shown in FIG. 38, the center of the conductive coil, starting with inner turn 348, is positioned a distance Y from the outer turn 349, along the longitudinal axis of the coil (shown as dashed line). Each successive turn may extend beyond the perimeter or circumference of the adjacent larger turn along the longitudinal axis. The conical coil may optionally also have a material, e.g., non-electrically conductive material attached to its surface or wrapped around the coil as described above.

Figure 39:
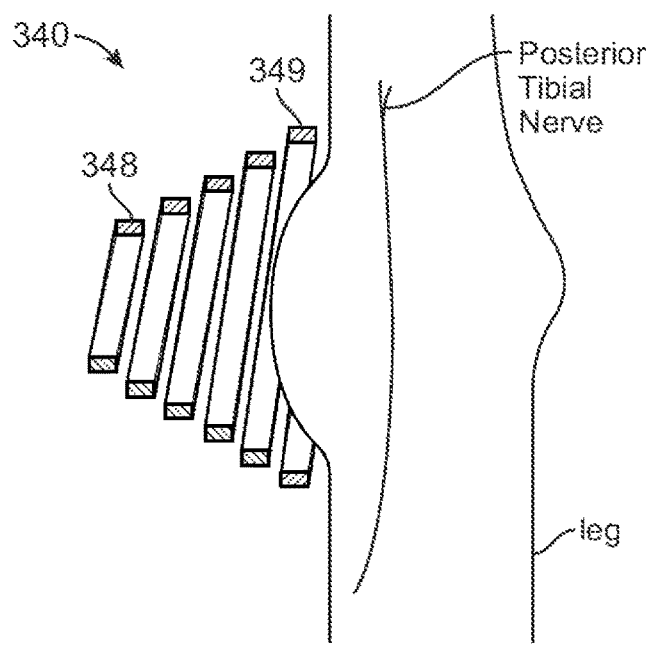
FIG. 39 shows a cross sectional of the conductive coil of FIG. 38 positioned over a malleolus.
Figure 40:
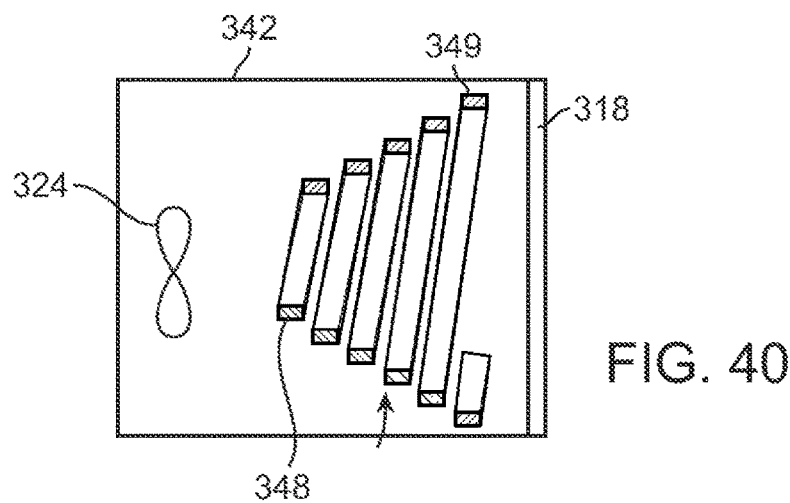
FIG. 40 shows a cross sectional side view of an energy emitting system including the conductive coil of FIG. 38.

FIG. 39 shows a cross sectional side view of an embodiment of a conductive coil 340, having a conical configuration. In use, the conductive coil 340 may be positioned against a patient's leg, over at least a portion of a patient's malleolus or ankle, in proximity to the underlying target nerve, e.g., tibial nerve. Optionally, as shown in FIG. 40, the conical coil 340 may be positioned within a housing 342, and incorporate any of the cooling mechanisms described above, for example, using cooling device 324 to pull or push air or other fluid around, over, and/or through the conductive coil 340.

Figure 41:
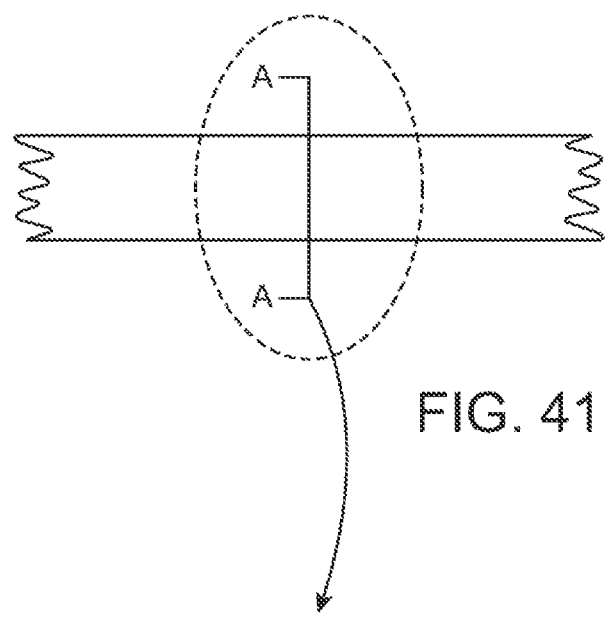
FIG. 41 shows a top view of a portion of a coil turn.
Figure 42:
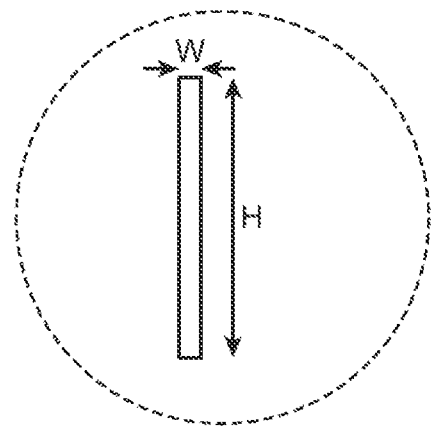
FIG. 42 shows a cross section of the coil turn of FIG. 41.

In any of the embodiments described herein, the coil may take on a variety of configurations. For example, a cross-sectional area of the coil may be substantially rectangular, square, or circular in shape. In certain embodiments, as shown in FIGS. 41 and 42, the coil may take on a ribbon-like configuration. FIG. 41 shows a top view of a section of a coil turn. The surface of the coil turn is substantially flat. FIG. 42 shows a cross section of the coil turn, where the height of the cross section is greater than its width, e.g., 25 to 60 times greater in height relative to its width. An end of the coil turn could have similar dimensions. This allows the coil to be tightly rolled or packed into a spiral configuration, suitable for conducting electrical current and generating an electromagnetic or magnetic field and/or cooling. The coil can be made from a variety of conductive materials, e.g., copper or other materials having similar properties.

Figure 43:
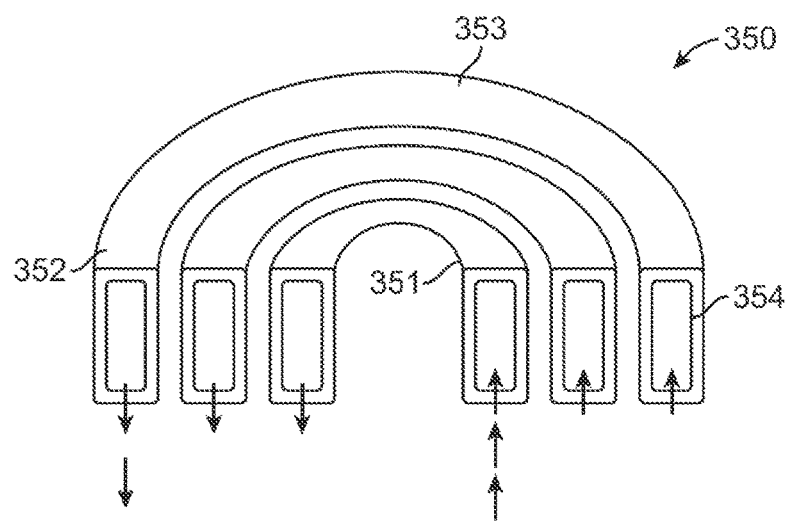
FIG. 43 is a cross sectional view of a variation of a conductive coil.

In another embodiment, an energy emitting system for providing a medical therapy can include a conductive coil 350 (a cross section of which is shown in FIG. 43) configured to generate a magnetic field focused on a target nerve. The conductive coil 350 can have a first end 351 and a second end 352 with a coil body 353 positioned between the first end and second end. A lumen 354 can extend through the coil body 353, from a first end to a second end. The lumen 354 provides a passage extending from the first end 351 to the second end 352 of the coil, which permits the passage of fluid between the first end and the second end for cooling the conductive coil 350. For example, air or a non-electrically conductive cooling liquid (indicated by the arrows) could be passed through the lumen 354 of the coil, thereby cooling the coil as it passes from one end to the other. The fluid can be cooled and recycled or a continuous stream of fresh fluid can be passed through the coil. Optionally, the conductive coil can be partially or completely coated with a material, e.g., a non-electrically conductive material (not shown) to ensure that the conductive surface of the coil turns making up the coil do not come into contact with each other.

Figures 44A, 44B:
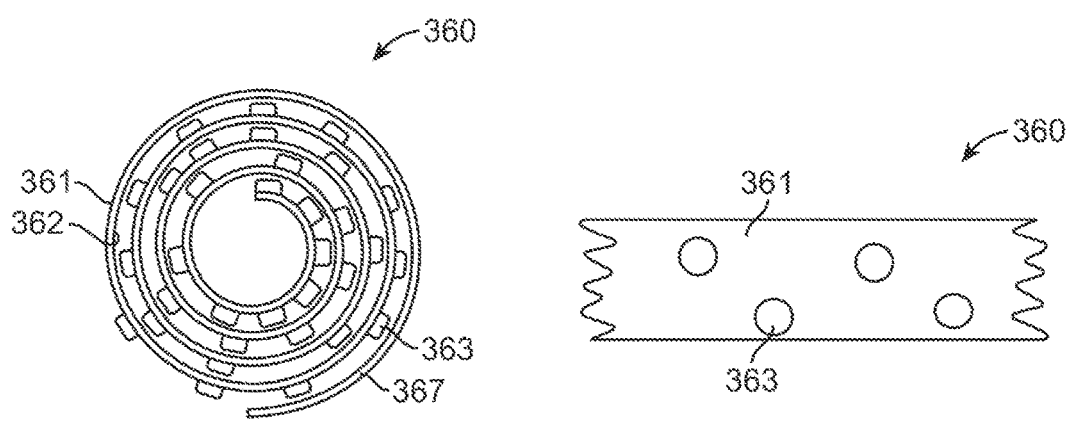

In another embodiment, an energy emitting system for providing a medical therapy can include a conductive coil 360 configured to generate a magnetic field focused on a target nerve. (FIGS. 44a and 44b) shows a top view of a portion of a coil turn making up the conductive coil 360). The conductive coil may have at least a first turn 307 and a second turn 307 or a series of turns. The second turn may have a radius of curvature that is greater than the radius of curvature of the first turn, such that the radius of each successive turn from the center of the coil to its outer perimeter increases. Each turn 307 has a top surface 361 and a bottom surface 362 and the top and/or bottom surface of the turns 307 may have one or more raised protrusions 363 extending therefrom. The protrusions 363 separate successive turns 367 from one another, forming a gap that allows for the passage of air or other fluid for cooling, e.g., by convection. Additionally, the protrusions 363 help ensure that the conductive surfaces 361, 362 of the turns 367 making up the coil do not come into contact with each other. The raised protrusion 363 may be made from various materials, e.g., ceramic or other materials having similar properties, and may be configured in a variety of shapes, e.g., circular, oval, rectangular, spherical, etc. The protrusions may be adhered, attached or otherwise affixed to the surface of the coil by any suitable manner known in the art.

Figure 45:
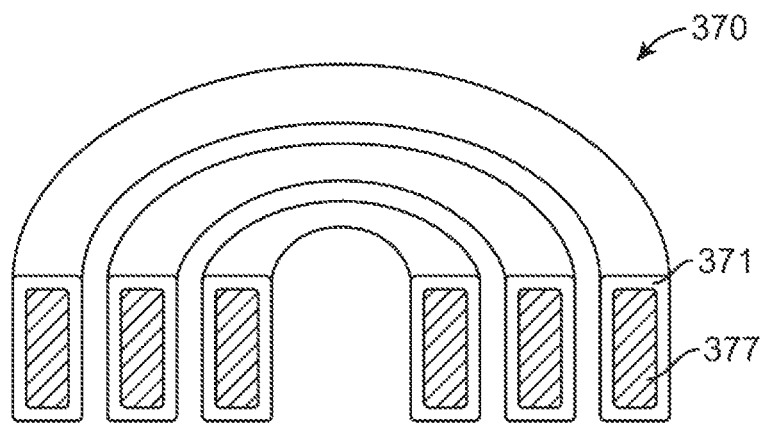
FIG. 45 is a cross sectional view of a variation of a conductive coil.

In another embodiment, (a cross section of which is shown in FIG. 45), at least a portion of a conductive coil 370, e.g., a surface of a turn 377 or the entire turn, may be coated or otherwise covered with a material 371, e.g., a non-electrically conductive or phase changing material. Material 371 can separate the turns 377 from one another and allow for cooling by conduction. The heat from the coil can be absorbed by the material 371 which acts as a heat sink. Various non-electrically conductive or phase changing materials may be used, e.g., wax or other materials having similar properties.

In use, the wax or other material absorbs the heat generated from the conductive coil. The wax may melt and change phases as it provides a heat sink. A cooling device (not shown), e.g., a fan, blower, etc., may also be implemented in the system where the cooling device is configured to cool and thereby harden the melted wax after or during the cooling process. Optionally, the coated conductive coil turns 377 can be surrounded by a casing (not shown) that holds the wax or other material in place such that it may be resolidified on the conductive coil 370 when cooled.

The non-electrically conductive or phase changing material can by applied or coated on the coil surface by a variety of techniques known to persons of skill in the art, e.g., by spraying, vapor, or dip. The coating can be reused or a fresh coating can be reapplied after each use. For example, wax can be melted and removed. Or the conductive coil can be replaced after use, once the wax or other coating is melted. The coating of the material may be applied such that it has a thickness on the coil's surface suitable to adequately cool a particular coil depending on the coils size, configuration, load, and/or power. The thickness may vary. For example, the material may have a thickness from about 0.25 inch to 1 inch or about 0.5 inch to 0.75 inch.

Optionally, in various embodiments, each turn of a conductive coil can be individually encased or coated within a material, e.g., a non-electrically conductive or phase changing material, such that the conductive coil turns are separated from one another or the entire coil body is insulated or covered. In other embodiments, one or more surfaces of the coil may be coated and not every coil turn may be coated.

Figure 46A:
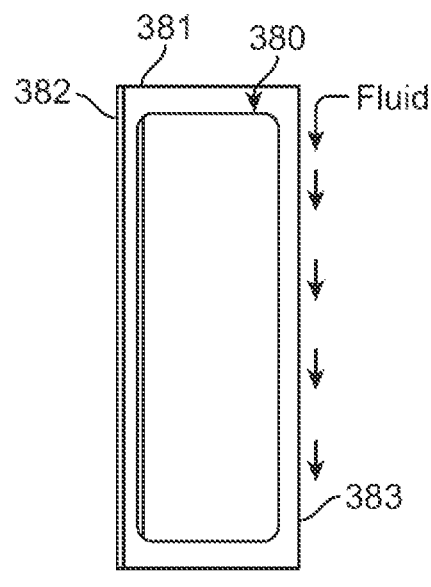
FIG. 46a shows a side view of an energy emitting system including a variation of a conductive coil.

FIG. 46a shows a side view of an embodiment of a conductive coil 380 which may be potted, covered or encased in a material 381, e.g., a non-electrically conductive or non-thermally conductive or thermally conductive material, e.g., a thermally conductive plastic, epoxy, or materials made by Cool Polymers® or other materials having similar properties or a combination of such properties. A cross section of the material 381 surrounding the conductive coil is shown in FIG. 46. The potting or casing material 381 may include a patient interface plate 382, separating the patient from the conductive coil as described above which is non-electrically conductive and/or non-thermally conductive or otherwise thermally or electrically insulated to protect the patient. A fluid may be passed over the back face 383 of the potting or casing, thereby cooling the conductive coil 380.

Figure 46B:
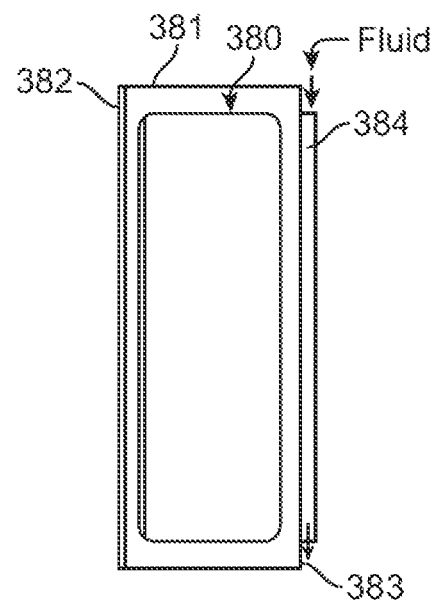

Optionally, as shown in FIG. 46b, one or more heat fins 384 can extend from the back face 383 of the potting or casing, providing channels for passing fluid over the conductive coil 380, thereby cooling the coil. The heat fins 384 may be attached to the casing or potting or be an extension thereof. The fluid may be supplied with a cooling device, e.g., fan, blower, refrigerator device. A pump or other system could be used for supplying the fluid over the potting or casing. The fluid could optionally be recycled for reuse, or cooled using a cooling device before initial or recycled use. Ambient air, or water or other fluid may optionally be used.

Figure 47:
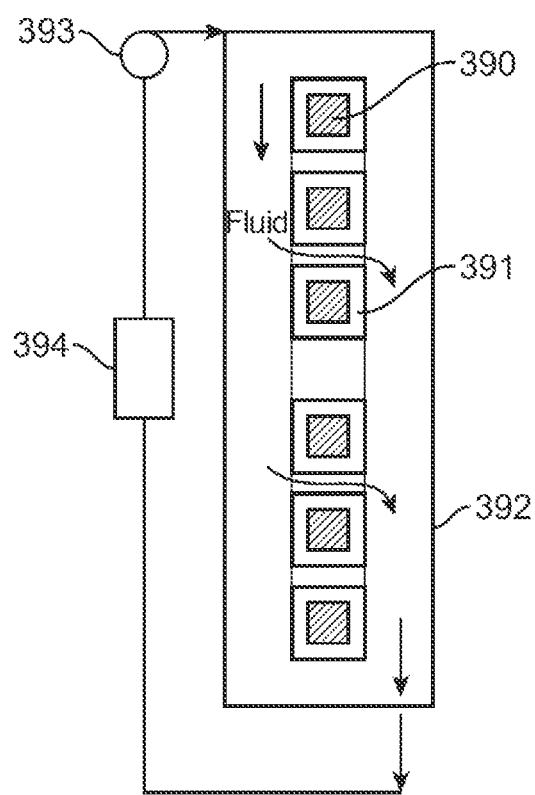
FIG. 47 is a cross sectional view of a variation of a conductive coil positioned within a cooling system.

In another embodiment, (a cross section of which is shown in FIG. 47), a conductive coil 390 may be encased or covered in a material, e.g., a non-electrically conductive material 391 such as a ceramic. The conductive coil 390 can then be placed in an additional casing or housing 392 which may hold fluid to be passed over and around the coil to cool the coil creating a cooling system. A pump 393 or other system could be implemented for moving the fluid over or around the coil and in between the coil turns. A cooling device 394 for cooling warmed or heated fluid that has passed through the system or for cooling fluid about to pass through the system may also be implemented. In certain embodiments, water may be the fluid used to cool the conductive coil.

In any of the conductive coil embodiments described herein, the first turn of a conductive coil may optionally surround a central aperture which is sized to receive a first portion of a patient's body such that the conductive coil is positioned in proximity to the underlying target nerve. The central aperture also aids in the cooling process as air or other fluid can pass through the aperture, over and around the conductive coil surface. Optionally, the central aperture may be sized to surround at least a portion of a malleolus, such that the conductive coil is positioned in proximity to the tibial nerve. As described supra, the conductive coils may be in the form of a spiral that is substantially planar, substantially conical or other configurations best suited for a particular device or patient.

Coils used in any of the embodiments described above and illustrated in the corresponding figures may take on a variety of shapes, sizes, and configurations. For example, a coil may be shaped as a spiral (as shown) or have a simple helical pattern or be a figure eight coil, a four leaf clover coil, a Helmholtz coil, a modified Helmholtz coil, or may be shaped as a combination of the aforementioned coil patterns. Additionally, other coil designs beyond those mentioned hereinabove might be utilized as long as a magnetic field is developed that will encompass a target nerve.

Optionally, any of the conductive coils described herein can be coated or otherwise covered with a material, e.g., a non-electrically conductive material, to ensure that the conductive surface of the turns making up the coil do not come into contact with each other.

The conductive coils described herein may have a variety of dimensions, shapes, and sizes. For example, in certain embodiments, a turn or end or cross section of a turn may have a height ranging from about 1 to 5 cm or from about 10 mm to 51 mm (about 0.3 inches to 2 inches) or about 25 mm to 40 mm (about 1 inch to 1.5 inches) or about 12 mm to 40 mm (about 0.5 inch to 1.5 inch) or about 0.5 inch to 2 inch. The turn or end or cross section of the turn may have a width ranging from about 0.5 mm to about 5 mm (about 0.019 inch to 0.19 inch) or from about 1 mm to about 2 mm (about 0.03 inch to 0.07 inch) or about 0.2 mm to about 1.6 mm (about 0.01 inch to 0.06 inch). The dimensions may allow the coil turns to be tightly packed or rolled while still maintaining gaps or spaces in between adjacent turns, allowing for conduction and/or cooling. The conductive coil may have a diameter ranging from about 4.5 inches to about 5 inches. In certain embodiments, the number of turns of a conductive coil can vary, e.g., a coil may include from about 14 to 20 turns, where a gap separates all or many of the turns from an adjacent turn.

In any of the above embodiments, the system may optionally include a sensor, e.g., a laser Doppler or ultrasound Doppler. The sensor may be used to detect (e.g., through the openings or spaces in the coil) the positioning of the tibial artery which runs along the tibial nerve, to help ensure proper placement of the patient's body relative to the conductive coil in order to conduct magnetic induction therapy.

It is also contemplated that any of the energy emitting systems or devices described herein can be used with or without a sensor for detecting conduction of a stimulated nerve or muscle stimulation resulting from the magnetic field generated by the conductive coil and delivered to a patient or an electrical stimulus delivered to a patient. Also, in any of the above embodiments, a controller may optionally be connected, coupled, integral to or otherwise in communication with the conductive coils and/or the sensor. Optionally, the sensor may be connected, coupled, integral to or otherwise in communication with the conductive coil.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. An energy emitting system for providing a medical therapy comprising:
   a conductive coil, wherein the conductive coil is configured to generate a magnetic field focused on a target nerve, the conductive coil comprising a coil body, and the conductive coil having a central aperture, and a non-electrically conductive material positioned partially on a surface of the coil body such that remaining portions of the coil body are exposed, wherein the non-electrically conductive material is configured to maintain fluid flow gaps between adjacent turns of the coil body;

a cooling device; and a housing having a patient interface plate wherein the conductive coil is positioned within the housing such that a gap is provided between the conductive coil and patient interface plate, the conductive coil being positioned between the patient interface plate and the cooling device;

wherein the cooling device is positioned within the housing and in proximity to the conductive coil such that the cooling device is positioned adjacent to the conductive coil transverse to a plane defined by the conductive coil, whereby air is forced into a transverse direction relative to the plane of the conductive coil and through the fluid flow gaps between adjacent turns and through the central aperture such that airflow passes through the turns to cool the conductive coil.

2. The system of claim 1, wherein the non-electrically conductive material is selected from the group consisting of epoxy, plastic, non-electrically conductive polymers, and silicone.

3. The system of claim 1, wherein the non-electrically conductive material comprises a tape wrapped around the coil body at a non-zero angle, the tape configured to maintain fluid flow gaps between adjacent turns of the coil body for cooling the conductive coil.

4. The system of claim 3, wherein the tape comprises silicone.

5. The system of claim 1, wherein the gap between the conductive coil and patient interface plate has a width ranging from about 1 mm to 2 mm.

6. The system of claim 1, wherein a distance between the non-electrically conductive material and the patient interface plate is from about 0.2 mm to 0.5 mm.

7. The system of claim 1 wherein the patient interface plate comprises a reflective surface.

8. The system of claim 1, wherein the cooling device comprises a fan which provides an airflow rate of from about 1 liter per second to 2 liters per second.

9. The system of claim 1, wherein the conductive coil is substantially planar, and wherein the conductive coil has a spiral configuration and a substantially flat surface.

10. The system of claim 1, wherein the conductive coil is substantially conical.

11. The system of claim 1, wherein a diameter of the conductive coil is from about 4.5 inches to about 5 inches in length.

12. The system of claim 1, wherein the conductive coil comprises 14 to 20 turns, and each turn is separated by a gap.

13. The system of claim 1, wherein the coil body further comprises a first turn wherein a cross section of the first turn is configured such that its height is greater than its width.

14. The system of claim 13, wherein the height is from about 0.5 inch to about 2 inch and the width is from about 0.01 inch to about 0.06 inch.

15. The system of claim 13, wherein the first turn comprises a first surface, and at least a portion of the first surface is coated with a phase changing material which allows for conduction cooling.

16. The system of claim 15, wherein the phase changing material comprises a wax.

17. The system of claim 15, further comprising a cooling device, wherein the cooling device is configured to cool and thereby solidify the phase changing material.

18. The system of claim 1, wherein the conductive coil has a substantially flat surface.

19. An energy emitting system for providing a medical therapy to a patient comprising:

a conductive coil positioned within a housing, wherein the conductive coil is configured to generate a magnetic field focused on a target nerve, and wherein the conductive coil comprises a coil body having a plurality of turns and wherein the conductive coil has a central aperture such that the conductive coil forms a spiral configuration which is planar with the plurality of turns and the central aperture located within a single plane and where a radius for each successive turn increases from a center of the spiral coil; and a cooling device, wherein the cooling device is positioned relative to the housing and the conductive coil such that the cooling device draws air into the housing, over the coil body, between first and second turns of the plurality of turns such that airflow surrounds the turns, and through the central aperture.

20. The energy emitting system of claim 19, further comprising a non-electrically conductive material positioned on a surface of the coil body, the material configured to maintain air flow gaps between adjacent turns of the coil body and provide an air flow channel for cooling the conductive coil.

21. The energy emitting system of claim 19, wherein the housing comprises a patient interface plate and a venting plate positioned substantially opposite the patient interface plate.

22. The energy emitting system of claim 21, further comprising a sensor positioned in proximity to the venting plate, wherein the sensor monitors temperature of warmed air vented from the venting plate.

23. The energy emitting system of claim 21, further comprising a sensor positioned in proximity to the patient interface plate, wherein the sensor monitors temperature of the patient interface plate.

24. The energy emitting system of claim 19, wherein the system is configured to provide from about 36,000 to 45,000 pulses over about 20 to 40 minutes, while a patient interface plate remains at a temperature of no greater than 42 degrees C.

25. The system of claim 19, further comprising a sensor configured to detect muscle stimulation or electrical conduction in the target nerve; and a controller coupled to the coil and in communication with the sensor.

26. The system of claim 19 wherein a first turn of the plurality of turns comprises a first surface having at least one raised protrusion separating the first turn from a second turn of the plurality of turns which forms a gap that allows for convection cooling.

27. The system of claim 26, wherein the at least one raised protrusion comprises a non-conductive material selected from the group consisting of ceramic or ceramic alloy.

28. The system of claim 26, wherein the second turn has a radius of curvature greater than a radius of curvature of the first turn.

29. The system of claim 19, wherein the conductive coil has a substantially flat surface.

30. An energy emitting system for providing a medical therapy comprising:

a conductive coil configured to generate a magnetic field focused on a target nerve, the conductive coil comprising: a first end and a second end; and a coil body having a plurality of turns which are positioned between the first end and second end, the conductive coil having a lumen, wherein the conductive coil forms a spiral configuration which is planar with the plurality of turns and a central aperture located within a single plane and where a radius for each successive turn increases from a center of the spiral coil, wherein the lumen extends in parallel with a length of the coil from the first end to the second end providing a passage extending through an interior of the conductive coil such that the passage follows the plurality of turns formed by the coil body and an opening at the first end is in fluid communication with an opening at the second end, and wherein the lumen is configured to permit the passage of fluid within the lumen between the first end and the second end for cooling the conductive coil.

31. A method of magnetic induction therapy comprising:
positioning a first portion of a patients body relative to an energy emitting device such that a target nerve within the first portion of the body is in proximity to a conductive coil having a plurality of turns and a central aperture, where the conductive coil is disposed within or along the energy emitting device, wherein the conductive coil forms a spiral configuration which is planar with the plurality of turns and the central aperture located within a single plane and where a radius for each successive turn increases from a center of the spiral coil;

passing a current through the conductive coil to generate a magnetic field focused on the target nerve;

concentrating a magnetic flux near the target nerve; and drawing in air at a flow rate over the conductive coil and in between first and second turns of the plurality of turns of the conductive coil such that the air surrounds the first and second turns, and passes through the central aperture of the conductive coil to cool the conductive coil.

32. The method of magnetic induction therapy according to claim 31, wherein the flow rate comprises a range of flow rates selected from the group consisting of 1 liter per second to about 5 liters per second or 2 liters per second to about 4 liters per second.

33. The method of magnetic induction therapy according to claim 31, wherein the flow rate comprises a range of flow rates selected from the group consisting of 20 CFM to about 100 CFM or from about 25 CFM to about 60 CFM.

34. The method of magnetic induction therapy according to claim 31, wherein the flow produces a range of pressure head selected from the group consisting of from about 0.5 inches of H20 to about 10 inches of H20 or from about 0.5 inches of H20 to about 4 inches of H20.

35. The method of magnetic induction therapy according to claim 31, further comprising venting warmed air away from the first portion of the patient's body.

36. The method of magnetic induction therapy according to claim 35, wherein the warmed air is vented in a direction substantially opposite the first portion of the patient's body.

37. The method of magnetic induction therapy according to claim 35, further comprising detecting a temperature of the warmed air.

38. The method of magnetic induction therapy according to claim 37, wherein the energy emitting device provides from about 36,000 to 45,000 pulses over about 20 to 40 minutes, while maintaining a patient interface plate of the device at a temperature of no greater than 42 degrees C.

39. The method of magnetic induction therapy according to claim 31, wherein the target nerve is the tibial nerve.

40. The method of magnetic induction therapy according to claim 31, further comprising treating a patient exhibiting symptoms associated with urinary incontinence, fecal incontinence, restless leg syndrome or premature ejaculation.

* * * * *